United States Patent
Lunkenheimer et al.

Patent Number: 5,863,933
Date of Patent: Jan. 26, 1999

[54] SUBSTITUTED BENZIMIDAZOLES

[75] Inventors: Winfried Lunkenheimer, Wuppertal; Bernd Baasner, Bergisch Gladbach; Folker Lieb, Leverkusen; Stefan Böhm, Krefeld; Albrecht Marhold, Leverkusen; Ulrich Görgens, Ratingen; Wilhelm Stendel, Wuppertal; Heinz-Wilhelm Dehne, Bonn; Hans-Joachim Santel, Leverkusen, all of Germany

[73] Assignee: Bayer Aktiengesellschaft, Leverkusen, Germany

[21] Appl. No.: 822,565

[22] Filed: Mar. 19, 1997

Related U.S. Application Data

[62] Division of Ser. No. 428,087, filed as PCT/EP93/02946 Oct. 25, 1993, Pat. No. 5,656,649.

[30] Foreign Application Priority Data

Nov. 6, 1992 [DE] Germany .......... 42 37 557.6

[51] Int. Cl.⁶ .......... A01N 43/52; C07D 235/10
[52] U.S. Cl. .......... 514/394; 548/310.1; 548/310.4
[58] Field of Search .......... 548/310.1, 310.4; 514/394

[56] References Cited

U.S. PATENT DOCUMENTS

| | | |
|---|---|---|
| 3,472,865 | 10/1969 | Newbold et al. |
| 3,531,495 | 9/1970 | Burton et al. |
| 5,306,692 | 4/1994 | Barton et al. |

FOREIGN PATENT DOCUMENTS 1213796 11/1970 United Kingdom.

*Primary Examiner*—Patricia L. Morris
*Attorney, Agent, or Firm*—Sprung Kramer Schaefer & Briscoe

[57] ABSTRACT

The invention relates to new substituted benzimidazole of the general formula (I)

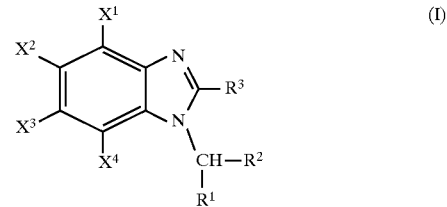

in which
$R^1$ represents hydrogen, alkyl, alkoxy or optionally substituted aryl,
$R^2$ represents hydroxyl, cyano or in each case optionally substituted alkyl, alkenyl, alkinyl, alkoxy, alkenyloxy, alkinyloxy, alkylthio, amino, aminocarbonyl, alkylcarbonyl, alkoxycarbonyl, alkoxycarbonyloxy, dialkoxyphosphonyl, (hetero)aryl, (hetero)arylcarbonyl, (hetero)aryloxycarbonyl, (hetero)arylcarbonyloxy or (hetero)arylaminocarbonylaminocarbonyloxy, and
$R^3$ represents fluoroalkyl,
$X^1$, $X^2$, $X^3$ and $X^4$ independently of one another in each case represent hydrogen, halogen, cyano, nitro, in each case optionally substituted alkyl, alkoxy, alkylthio, alkylsulphinyl, alkylsulphonyl or cycloalkyl, optionally substituted, fused dioxyalkylene, or represent hydroxycarbonyl, alkylcarbonyl, alkoxycarbonyl or cycloalkyloxycarbonyl, in each case optionally substituted amino or aminocarbonyl or in each case optionally substituted aryl, aryloxy, arylthio, arylsulphinyl, arylsulphonyl, arylsulphonyloxy, arylcarbonyl, aryloxycarbonyl, arylazo or arylthiomethylsulphonyl, but where at least one of the substituents $X^1$, $X^2$, $X^3$ or $X^4$ represents halogenoalkyl, with the exception of the chloromethyl radical, halogenoalkoxy, halogenoalkylthio, halogenoalkylsulphinyl, halogenoalkylsulphonyl or alkylsulphonyl, optionally substituted, fused dioxyalkylene, or represent hydroxycarbonyl, alkylcarbonyl, alkoxycarbonyl or cycloalkyloxycarbonyl, in each case optionally substituted amino or aminocarbonyl, or in each case optionally substituted aryl, arylthio, arylsulphinyl, arylsulphonyl, arylsulphonyloxy, arylcarbonyl, aryloxycarbonyl, arylazo or arylthiomethylsulphonyl, their preparation and use as pesticides, and intermediates for their preparation.

3 Claims, No Drawings

SUBSTITUTED BENZIMIDAZOLES

This is a division of Application Ser. No. 081428,087, filed on May 25, 1995, U.S. Pat. No. 5,656,649 now which is a 371 of PCT/EP93/02946 filed on Oct. 25, 1993.

It has been disclosed that certain phosphoric esters or carbamates, such as, for example, the compound O,S-dimethyl-thiolo-phosphoramide or the compound O-(2-isopropoxyphenyl) N-methyl-carbamate, have insecticidal properties (cf., for example, DE 1,210,835 or DE 1,108, 202).

However, the level, or duration, of action of these previously known compounds is not entirely satisfactory in all fields of application, in particular in the case of certain insects or when low concentrations are applied.

New substituted benzimidazole of the general formula (I)

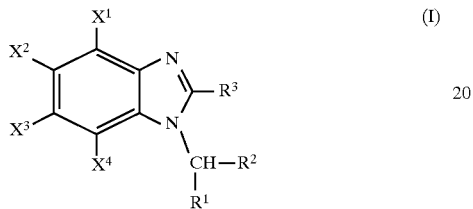

in which
- $R^1$ represents hydrogen, allyl, alkoxy or optionally substituted aryl,
- $R^2$ represents hydroxyl, cyano or in each case optionally substituted alkyl, alkenyl, alkinyl, alkoxy, alkenyloxy, alkinyloxy, alkylthio, amino, aminocarbonyl(—$CONH_2$), alkylcarbonyl, alkoxycarbonyl, alkylcarbonyloxy, dialkoxyphosphonyl, (hetero)aryl, (hetero)arylcarbonyl, (hetero,)aryloxycarbonyl, (hetero)arylcarbonyloxy or (hetero)arylaminocarbonylaminocarbonyloxy,
- $R^3$ represents fluoroalkyl,
- $X^1$, $X^2$, $X^3$ and $X^4$ independently of one another in each case represent hydrogen, halogen, cyano, nitro, in each case optionally substituted alkyl, alkoxy, alkylthio, alkylsulphinyl, alkylsulphonyl or cycloalkyl, optionally substituted, fused dioxyalkylene, or represent hydroxycarbonyl, alkylcarbonyl, alkoxycarbonyl or cycloalkyloxycarbonyl, in each case optionally substituted amino or aminocarbonyl or in each case optionally substituted aryl, aryloxy, arylthio, arylsulphinyl, arylsulphonyl, arylsulphonyloxy, arylcarbonyl, aryloxycarbonyl, arylazo or arylthiomethylsulphonyl, but where at least one of the substituents $X^1$, $X^2$, $X^3$ or $X^4$ represents halogenoalkyl, with the exception of the chloromethyl radical, halogenoalkoxy, halogenoalkylthio, halogenoalkylsulphinyl, halogenoalkylsulphonyl or alkylsulphonyl, optionally substituted, fused dioxyalkylene, or represent hydroxycarbonyl, alkylcarbonyl, alkoxycarbonyl or cycloalkyloxycarbonyl, in each case optionally substituted amino or aminocarbonyl, or in each case optionally substituted aryl, arylthio, arylsulphinyl, arylsulphonyl, arylsulphonyloxy, arylcarbonyl, aryloxycarbonyl, arylazo or arylthiomethylsulphonyl, have been found.

The compounds of the formula (I) may optionally be present in the form of geometric and/or optical isomers or regioisomers or their isomer mixtures in varying composition, depending on the nature and number of the substituents. The invention claims the pure isomers and the isomer mixtures.

Furthermore, it has been found that the new substituted benzimidazoles of the general formula (I)

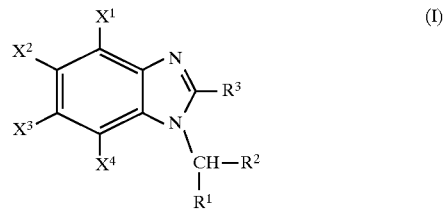

in which
- $R^1$ represents hydrogen, alkyl, alkoxy or optionally substituted aryl,
- $R^2$ represents hydroxyl, cyano or in each case optionally substituted alkyl, alkenyl, alkinyl, alkoxy, alkenyloxy, alkinyloxy, alkylthio, amino, aminocarbonyl, alkycarbonyl, alkoxycarbonyl, alkylcabonyloxy, dialkoxyphosphonyl, (hetero)aryl, (hetero) arylcarbonyl, (hetero)aryloxycarbonyl, (hetero) arylcarbonyloxy or (hetero)arylaminocarbonylamiocarbonyloxy,
- $R^3$ represents fluoroalkyl,
- $X^1$, $X^2$, $X^3$ and $X^4$ independently of one another in each case represent hydrogen, halogen, cyano, nitro, in each case optionally substituted alkyl, alkoxy, alkylthio, alkylsulphinyl, alkylsulphonyl or cycloalkyl, optionally substituted, fused dioxyalkylene, or represent hydroxycarbonyl, alkylcabonyl, alkoxycarbonyl or cycloalkyloxycarbonyl, in each case optionally substituted amino or aminocarbonyl or in each case optionally substituted aryl, aryloxy, arylthio, arylsulphinyl, arylsulphonyl, arylsulphonyloxy, arylcarbonyl, aryloxycarbonyl, arylazo or arylthiomethylsulphonyl, but where at least one of the substituents $X^1$, $X^2$, $X^3$ or $X^4$ represents halogenoalkyl, with the exception of the chloromethyl radical, halogenoalkoxy, halogenoalkylthio, halogenoalkylsulphinyl, halogenoalkylsulphonyl or alkylsulphonyl, optionally substituted, fused dioxyalkylene, or represent hydroxycarbonyl, alkylcarbonyl, alkoxycarbonyl or cycloalkyloxycarbonyl, in each case optionally substituted amino or aminocarbonyl, or in each case optionally substituted aryl, arylthio, arylsulphinyl, arylsulphonyl, arylsulphonyloxy, arylcarbonyl, aryloxycarbonyl, arylazo or arylthiomethylsulphonyl, are obtained when a) 1H-benzimidazoles of the formula (II),

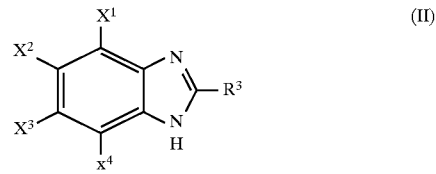

in which
$R^3$, $X^1$, $X^2$, $X^3$ and $X^4$ have the abovementioned meaning, are reacted with compounds of the formula (III),

in which
A represents a suitable leaving group,
$R^1$ has the abovementioned meaning and
$R^2$ has the abovementioned meaning,
if appropriate in the presence of a diluent and, if appropriate, in the presence of a reaction auxiliary.

Finally, it has been found that the new substituted benzimidazoles of the general formula (I) have a good activity against pests.

Surprisingly, the substituted benzimidazoles of the general formula (I) according to the invention show a considerably better insecticidal activity compared with the phosphoric esters or carbamates known from the prior art, such as, for example, the compound O,S-dimethyl-thiolophosphoramide or the compound O-(2-isopropoxyphenyl) N-methyl carbamate, which are compounds with a similar action.

Formula (I) provides a general definition of the substituted benzimidazoles according to the invention. Preferred compounds of the formula (I) are those in which $R^1$ represents hydrogen, in each case straight-chain or branched alkyl or alkoxy, each of which has 1 to 8 carbon atoms, or phenyl which is optionally monosubstituted or polysubstituted by identical or different substituents, suitable substituents being:

halogen, cyano, nitro, in each case straight-chain or branched alkyl alkoxy, alkylthio, alkylsulphinyl or alkylsulphonyl, each of which has 1 to 6 carbon atoms, in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms, in each case straight-chain or branched alkoxyalkyl, alkoxyalkoxy, alkanoyl, alkoxycarbonyl or alkoximinoalkyl, each of which has 1 to 6 carbon atoms in the individual alkyl moieties, divalent dioxyalkylene having 1 to 5 carbon atoms which is optionally monosubstituted or polysubstituted by identical or different substituents from the series consisting of halogen and/or straight-chain or branched alkyl having 1 to 6 carbon atoms and/or straight-chain or branched halogenoalkyl having 1 to 6 carbon atoms and 1 to 13 identical or different halogen atoms, or phenyl which is optionally monosubstituted or polysubstituted by identical or different substituents from the series consisting of halogen and/or straight-chain or branched alkyl having 1 to 6 carbon atoms and/or straight-chain or branched halogenoalkyl having 1 to 6 carbon atoms and 1 to 13 identical or different halogen atoms, $R^2$ represents hydroxyl, cyano, or represents alkyl, alkenyl, alkinyl, alkoxy, alkenyloxy, alkinyloxy, alkylthio, alkylcarbonyl, alkoxycarbonyl, alkylcarbonyloxy or dialkoxyphosphonyl, each of which has up to 8 carbon atoms in the individual alkyl, alkenyl or alkinyl moieties and each of which is optionally monosubstituted or polysubstituted by identical or different substituents, suitable substituents in each case being: halogen, straight-chain or branched alkoxy having 1 to 8 carbon atoms, or aryl having 6 to 10 carbon atoms or heteroaryl having 2 to 9 carbon atoms and 1 to 5 hetero atoms—in particular nitrogen, oxygen and/or sulphur—each of these aryl or heteroaryl substituents optionally being monosubstituted or polysubstituted by identical or different substituents, suitable aryl or heteroaryl substituents being those mentioned in the case of $R^1$, $R^2$ furthermore represents amino or aminocarbonyl, each of which is optionally monosubstituted or disubstituted by identical or different substituents, suitable substituents in each case being:

formyl, straight chain or branched alkyl having 1 to 8 carbon atoms, straight-chain or branched alkenyl having 2 to 8 carbon atoms, straight-chain or branched alkylsulphonyl having 1 to 8 carbon atoms, carbamoyl, thiocarbamoyl or sulphamoyl, each of which is optionally monosubstituted or disubstituted by identical or different straight-chain or branched alkyl substituents having 1 to 8 carbon atoms, or cycloalkyl, cycloalkylcarbonyl or cycloalkyloxycarbonyl, each of which has 3 to 8 carbon atoms in the cycloalkyl moiety, alkylcarbonyl, alkenylcarbonyl, alkoxycarbonyl, alkenyloxycarbonyl, alkylthio-carbonyl, alkoxy-thiocarbonyl or alkylthio-thiocarbonyl, each of which has 1 to 8 carbon atoms in the individual straight-chain or branched alkyl moieties, in each case divalent and cyclized alkanediylcarbonyl or alkanediyloxycarbonyl, each of which has 2 to 6 carbon atoms in the alkanediyl moiety, or arylalkyl, arylalkylcarbonyl or arylalkyloxycarbonyl, each of which has 6 to 10 carbon atoms in the aryl moiety and 1 to 8 carbon atoms in the straight-chain or branched alkyl moiety and each of which is optionally monosubstituted or polysubstituted in the aryl moiety by identical or different substituents, or aryl, arylcarbonyl or aryloxycarbonyl, each of which has 6 to 10 carbon atoms in the aryl moiety and each of which is optionally monosubstituted or polysubstituted in the aryl moiety, by identical or different substituents, suitable aryl substituents in each case being those mentioned in the case of $R^1$, $R^2$ furthermore represents aryl, arylcarbonyl, aryloxycarbonyl, arylcarbonyloxy or arylaminocarbonylaminocarbonyloxy, each of which has 6 to 10 carbon atoms in the aryl moiety and each of which is optionally monosubstituted or polysubstituted by identical or different substituents, suitable aryl substituents in each case being those mentioned in the case of $R^1$, $R^2$ furthermore represents heteroaryl, heteroarylcarbonyl, heteroaryloxycarbonyl, heteroarylcarbonyloxy or heteroarylaminocarbonylaminocarbonyloxy, each of which has 2 to 9 carbon atoms and 1 to 5 identical or different hetero atoms—in particular nitrogen, oxygen and/or sulphur—in the heteroaryl moiety and each of which is optionally monosubstituted or polysubstituted by identical or different substituents, suitable heteroaryl substituents in each case being the aryl substituents mentioned in the case of $R^1$, and $R^3$ represents perfluoroalkyl or partially fluorinated alkyl having 1 to 25 C atoms and up to 50 F atoms, $X^1$, $X^2$, $X^3$ and $X^4$ independently of one another in each case represent hydrogen, fluorine, chlorine, bromine, iodine, cyano, nitro, in each case straight-chain or branched alkyl, alkoxy, alkylthio, alkylsulphinyl or alkylsulphonyl, each of which has 1 to 8 carbon atoms, cycloalkyl having 3 to 8 carbon atoms, in each case straight-chain or branched halogenoalkyl, halogenoalkoxy, halogenoalkylthio, halogenoalkylsulphinyl, halogenoalkylsulphonyl, each of which has 1 to 6 carbon atoms and 1 to 13 identical or different halogen atoms, or divalent dioxyalkylene having 1 to 5 carbon atoms which is optionally monosubstituted or polysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms, furthermore represent hydroxycarbonyl, in each case straight-chain or branched alkylcarbonyl or alkoxycarbonyl, each of which has 1 to 6 carbon atoms in the alkyl moiety, cycloalkyloxycarbonyl having 3 to 8 carbon atoms in the cycloalkyl moiety, or amino or aminocarbonyl, each of which is optionally monosubstituted or polysubstituted by identical or different substituents, suitable amino substituents in each case being:

in each case straight-chain or branched alkyl having 1 to 6 carbon atoms, halogenoalkyl having 1 to 6 carbon atoms and 1 to 13 halogen atoms, alkoxyalkyl or alkylcarbonyl, each of which has 1 to 6 carbon atoms in the individual alkyl moieties, or arylcarbonyl, arylsulphonyl, arylaminocarbonyl or arylmethylsulphonyl, each of which has 6 to 10 carbon atoms in the aryl moiety and each of which is optionally monosubstituted or polysubstituted in the aryl moiety by identical or different substituents, suitable aryl substituents in each case being those mentioned in the case of $R^1$;

furthermore represent aryl, aryloxy, arylthio, arylsulphinyl, arylsulphonyl, arylsulphonyloxy, arylcarbonyl, aryloxycarbonyl, arylthiomethylsulphonyl or arylazo, each of which has 6 to 10 carbon atoms in the aryl moiety and each of which is optionally monosubstituted or polysubstituted in the aryl moiety by identical or different substituents, suitable suitable aryl substituents in each case being those mentioned in the case of $R^1$, where at least one of the substituents $X^1$, $X^2$, $X^3$ or $X^4$ represents in each case straight-chain or branched halogenoalkyl (with the exception of the chloromethyl radical), halogenoalkoxy, halogenoalkylthio, halogenoalkylsulphinyl or halogenoalkylsulphonyl, each of which has 1 to 6 carbon atoms and 1 to 13 identical or different halogen atoms, straight-chain or branched alkylsulphonyl having 1 to 6 carbon atoms or divalent dioxyalkylene having 1 to 5 carbon atoms which is optionally monosubstituted or polysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms, furthermore represents hydroxycarbonyl, in each case straight-chain or branched alkylcarbonyl or alkoxycarbonyl, each of which has 1 to 6 carbon atoms in the alkyl moiety, cycloalkyloxycarbonyl having 3 to 8 carbon atoms in the cycloalkyl moiety, or amino or aminocarbonyl, each of which is optionally monosubstituted or polysubstituted by identical or different substituents, suitable amino substituents in each case being:

in each case straight-chain or branched alkyl having 1 to 6 carbon atoms, halogenoalkyl having 1 to 6 carbon atoms and 1 to 13 halogen atoms, alkoxyalkyl or alkylcarbonyl, each of which has 1 to 6 carbon atoms in the individual alkyl moieties, or arylcarbonyl, arylsulphonyl, arylaminocarbonyl or arylmethylsulphonyl, each of which has 6 to 10 carbon atoms in the aryl moiety and each of which is optionally monosubstituted or polysubstituted in the aryl moiety by identical or different substituents, suitable aryl substituents in each case being those mentioned in the case of $R^1$;

furthermore represents aryl, arylthio, arylsulphinyl, arylsulphonyl, arylsulphonyloxy, arylcarbonyl, aryloxycarbonyl, arylthiomethylsulphonyl or arylazo, each of which has 6 to 10 carbon atoms in the aryl moiety and each of which is optionally monosubstituted or polysubstituted in the aryl moiety by identical or different substituents, suitable aryl substituents in each case being those mentioned in the case of $R^1$.

Particularly preferred compounds of the formula (I) are those in which $R^1$ represents hydrogen, in each case straight-chain or branched alkyl or alkoxy, each of which has 1 to 6 carbon atoms, or phenyl which is optionally monosubstituted to trisubstituted by identical or different substituents, suitable substituents being:

halogen, cyano, nitro, in each case straight-chain or branched alkyl, alkoxy, alkylthio, alkylsulphinyl or alkylsulphonyl, each of which has 1 to 4 carbon atoms, in each case straight-chain or branched halogenoalkyl, halogenoalkoxy, halogenoalkylthio, halogenoalkylsulphinyl or halogenoalkylsulphonyl, each of which has 1 to 4 carbon atoms and 1 to 9 identical or different halogen atoms, in each case straight-chain or branched alkoxyalkyl, alkoxyalkoxy, alkanoyl, alkoxycarbonyl or alkoximinoalkyl, each of which has 1 to 4 carbon atoms in the individual alkyl moieties, divalent dioxyalkylene having 1 to 4 carbon atoms which is optionally monosubstituted to hexasubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms, or phenyl which is optionally monosubstituted to pentasubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms, $R^2$ represents hydroxyl or cyano, or alkyl, alkenyl, alkinyl, alkoxy, alkenyloxy, alkinyloxy, alkylthio, alkylcarbonyl, alkoxycarbonyl, alkylcarbonyloxy or dialkoxyphosphonyl, each of which has up to 6 carbon atoms in the individual alkyl, alkenyl or alkinyl moieties and each of which is optionally monosubstituted to pentasubstituted by identical or different halogen substituents, or alkyl, alkenyl, alkinyl, alkoxy, alkenyloxy, alkinyloxy, alkylthio, alkylcarbonyl, alkoxycarbonyl, alkylcarbonyloxy or dialkoxyphosphonyl, each of which has up to 6 carbon atoms in the individual alkyl, alkenyl or alkinyl moieties and each of which is optionally monosubstituted to trisubstituted by identical or different substituents, suitable substituents in each case being:

straight-chain or branched alkoxy having 1 to 6 carbon atoms, or aryl having 6 or 10 carbon atoms or heteroaryl having 2 to 9 carbon atoms and 1 to 4 hetero atoms—in particular nitrogen, oxygen and/or sulphur—each of which is optionally monosubstituted to trisubstituted by identical or different substituents, suitable aryl or heteroaryl substituents being those mentioned in the case of $R^1$, $R^2$ furthermore represents amino or aminocarbonyl, each of which is optionally monosubstituted or disubstituted by identical or different substituents, suitable substituents in each case being:

formyl, straight-chain or branched alkyl having 1 to 6 carbon atoms, straight-chain or branched alkenyl having 2 to 6 carbon atoms, straight-chain or branched alkylsulphonyl having 1 to 6 carbon atoms, carbamoyl, thiocarbamoyl or sulphamoyl, each of which is optionally monosubstituted or disubstituted by identical or different straight-chain or branched alkyl, substituents having 1 to 6 carbon atoms, or cycloalkyl, cycloalkylcarbonyl or cycloalkyloxycarbonyl, each of which has 3 to 7 carbon atoms in the cycloalkyl moiety, alkylcarbonyl, alkenylcarbonyl, alkoxycarbonyl, alkenyloxycarbonyl, alkylthio carbonyl, alkoxythiocarbonyl or alkylthio-thiocarbonyl, each of which has 1 to 6 carbon atoms in the individual straight-chain or branched alkyl moieties, in each case divalent and cyclized alkanediylcarbonyl or alkanediyloxycarbonyl, each of which has 2 to 5 carbon atoms in the alkanediyl moiety, or arylalkyl, arylalkylcarbonyl or arylalkyloxycarbonyl, each of which has 6 or 10 carbon atoms in the aryl moiety and 1 to 6 carbon atoms in the straight-chain or branched alkyl moiety and each of which is optionally monosubstituted to trisubstituted in the aryl moiety by identical or different substituents, or aryl, arylcarbonyl or aryloxycarbonyl, each of which has 6 or 10 carbon atoms in the aryl moiety and each of which is optionally monosubstituted to trisubstituted in the aryl moiety by identical or different substituents, suitable aryl substituents in each case being those mentioned in the case of $R^1$, $R^2$ furthermore represents aryl, arylcarbonyl, aryloxycarbonyl, arylcarbonyloxy or arylaminocarbonylaminocarbonyloxy, each of which has 6 or 10 carbon atoms in the aryl moiety and each of which is optionally monosubstituted to pentasubstituted by identical or different substituents, suitable aryl substituents in each case being those mentioned in the case of $R^1$, $R^2$ furthermore represents heteroaryl, heteroarylcarbonyl, heteroaryloxycarbonyl, heteroarylcarbonyloxy or heteroarylaminocarbonylaminocarbonyloxy, each of which has 2 to 9 carbon atoms and 1 to 4 identical or different hetero atoms—in particular nitrogen, oxygen and/or sulphur—in the heteroaryl moiety and each of which is optionally monosubstituted to pentasubstituted by identical or different substituents, suitable heteroaryl substituents in each case being the aryl substituents mentioned in the case of $R^1$, and $R^3$ represents $CF_3$, $C_2F_5$ or $C_7F_{15}$, $X^1$, $X^2$, $X^3$ and $X^4$ independently of one another in each case represent hydrogen, fluorine, chlorine, bromine, cyano, nitro, in each case straight-chain or branched allyl, alkoxy, alkylthio, alkylsulphinyl or alkylsulphonyl, each of which has 1 to 6 carbon atoms, cycloalkyl having 3 to 7 carbon atoms, in each case straight-chain or branched halogenoalkyl, halogenoalkoxy, halogenoalkylthio, halogenoalkylsulphinyl, halogenoalkylsulphonyl, each of which has 1 to 4 carbon atoms and 1 to 9 identical or different halogen atoms, or divalent dioxyalkylene having 1 to 4 carbon atoms which is optionally monosubstituted to hexasubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms, furthermore represent hydroxycarbonyl, in each case straight-chain or branched alkylcarbonyl or alkoxycarbonyl, each or which has 1 to 4 carbon atoms in the alkyl moiety, cycloalkyloxycarbonyl having 3 to 7 carbon atoms in the cycloalkyl moiety, or amino or aminocarbonyl, each of which is optionally monosubstituted or disubstituted by identical or different substituents, suitable amino substituents in each case being:

in each case straight-chain or branched alkyl having 1 to 4 carbon atoms, halogenoalkyl having 1 to 4 carbon atoms and 1 to 9 halogen atoms, alkoxyalkyl or alkylcarbonyl, each of which has 1 to 4 carbon atoms in the individual alkyl moieties, or arylcarbonyl, arylsulphonyl, arylaminocarbonyl or arylmethylsulphonyl, each of which has 6 or 10 carbon atoms in the aryl moiety and each of which is optionally monosubstituted to pentasubstituted in the aryl moiety by identical or different substituents, suitable aryl substituents in each case being those mentioned in the case of $R^1$;

furthermore represent aryl, aryloxy, arylthio, arylsulphinyl, arylsulphonyl, arylsulphonyloxy, arylcarbonyl, aryloxycarbonyl, arylthiomethylsulphonyl or arylazo, each of which has 6 or 10 carbon atoms in the aryl moiety and each of which is optionally monosubstituted to pentasubstituted in the aryl moiety by identical or different substituents, suitable suitable aryl substituents in each case being those mentioned in the case of $R^1$;

where at least one of the substituents $X^1$, $X^2$, $X^3$ or $X^4$ represents in each case straight-chain or branched halogenoalkyl (with the exception of the chloromethyl radical), halogenoalkoxy, halogenoalkylthio, halogenoalkylsulphinyl or halogenoalkylsulphonyl, each of which has 1 to 4 carbon atoms and 1 to 9 identical or different halogen atoms, straight-chain or branched alkylsulphonyl having 1 to 4 carbon atoms or divalent dioxyalkylene having 1 to 4 carbon atoms which is optionally monosubstituted to hexasubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms, furthermore represents hydroxycarbonyl, in each case straight-chain or branched alkylcarbonyl or alkoxycarbonyl, each of which has 1 to 4 carbon atoms in the alkyl moiety, cycloalkyloxycarbonyl having 3 to 7 carbon atoms in the cycloalkyl moiety, or amino or aminocarbonyl, each of which is optionally monosubstituted or disubstituted by identical or different substituents, suitable amino substituents in each case being:

in each case straight-chain or branched alkyl having 1 to 4 carbon atoms, halogenoalkyl having 1 to 4 carbon atoms and 1 to 9 halogen atoms, alkoxyalkyl or alkylcarbonyl, each of which has 1 to 4 carbon atoms in the individual alkyl moieties, or arylcarbonyl, arylsulphonyl, arylaminocarbonyl or arylmethylsulphonyl, each of which has 6 or 10 carbon atoms in the aryl moiety and each of which is optionallt monosubstituted to pentasubstituted in the aryl moiety by identical or different substituents, suitable aryl substituents in each case being those mentioned in the case of $R^1$;

furthermore represents aryl, arylthio, arylsulphinyl, arylsulphonyl, arylsulphonyloxy, arylcarbonyl, aryloxycarbonyl, arylthiomethylsulphonyl or arylazo, each of which has 6 or 10 carbon atoms in the aryl moiety, such as phenyl or naphthyl, and each of which is optionally monosubstituted to pentasubstituted in the aryl moiety by identical or different substituents, suitable suitable aryl substituents in each case being those mentioned in the case of $R^1$.

Very particularly preferred compounds of the formula (I) are those in which $R^1$ represents hydrogen, in each case straight-chain or branched alkyl or alkoxy, each of which has 1 to 4 carbon atoms, or phenyl which is optionally monosubstituted or disubstituted by identical or different substituents, suitable substituents being:

halogen, cyano, nitro, in each case straight-chain or branched alkyl, alkoxy, alkylthio, alkylsulphinyl or alkylsulphonyl, each of which has 1 to 3 carbon atoms, in each case straight-chain or branched halogenoalkyl, halogenoalkoxy, halogenoalkylthio, halogenoalkylsulphinyl or halogenoalkylsulphonyl, each of which has 1 to 3 carbon atoms and 1 to 7 identical or different halogen atoms, in each case straight-chain or branched alkoxyalkyl, alkoxyalkoxy, alkanoyl, alkoxycarbonyl or alkoximinoalkyl, each of which has 1 to 3 carbon atoms in the individual alkyl moieties, divalent dioxyalkylene having 1 to 3 carbon atoms which is optionally monosubstituted to tetrasubstituted by identical or different substituents from the series consisting of halogen and/or straight-chain or branched alkyl having 1 to 3 carbon atoms and/or straight-chain or branched halogenoalkyl having 1 to 3 carbon atoms and 1 to 7 identical or different halogen atoms, or phenyl which is optionally monosubstituted to trisubstituted by identical or different substituents from the series consisting of halogen and/or straight-chain or branched alkyl having 1 to 3 carbon atoms and/or straight-chain or branched halogenoalkyl having 1 to 3 carbon atoms and 1 to 7 identical or different halogen atoms, $R^2$ represents hydroxyl or cyano, or alkyl, alkenyl, alkinyl, alkoxy, alkenyloxy, alkinyloxy, alkylthio, alkylcarbonyl, alkoxycarbonyl, alkylcarbonyloxy or dialkoxyphosphonyl, each of which has up to 4 carbon atoms in the individual alkyl, alkenyl or alkinyl moieties and each of which is optionally monosubstituted to trisubstituted by identical or different halogen substituents—in particular fluorine, chlorine and/or bromine substituents—or alkyl, alkenyl, alkinyl, alkoxy, alkenyloxy, alkinyloxy, alkylthio, alkylcarbonyl, alkoxycarbonyl, alkylcarbonyloxy or dialkoxyphosphoryl, each of which has up to 4 carbon atoms in the individual alkyl, alkenyl or alkinyl moieties and each of which is optionally monosubstituted or disubstituted by identical or different substituents, suitable substituents, in each case being:

straight-chain or branched alkoxy having 1 to 3 carbon atoms or phenyl which is optionally monosubstituted or disubstituted by identical or different substituents, suitable phenyl substituents being those mentioned in the case of $R^1$, $R^2$ furthermore represents amino or aminocarbonyl, each of which is optionally monosubstituted or disubstituted by identical or different substituents, suitable substituents in each case being:

formyl, straight-chain or branched alkyl having 1 to 4 carbon atoms, straight-chain or branched alkenyl having 2 to 4 carbon atoms, straight-chain or branched alkylsulphonyl having 1 to 4 carbon atoms, carbamoyl, thiocarbamoyl or sulphamoyl, each of which is optionally monosubstituted or disubstituted by identical or different straight-chain or branched alkyl substituents having 1 to 4 carbon atoms, or cycloalkyl, cycloalkylcarbonyl or cycloalkyloxycarbonyl, each of which has 3 to 6 carbon atoms in the cycloalkyl moiety, alkylcarbonyl, alkenylcarbonyl, alkoxycarbonyl, alkenyloxycarbonyl, alkylthio-carbonyl, alkoxythiocarbonyl or alkoxycarbonylthiocarbonyl, each of which has 1 to 4 carbon atoms in the individual straight-chain or branched alkyl moieties, in each case divalent and cyclized alkanediylcarbonyl or alkanediyloxycarbonyl, each of which has 2 to 4 carbon atoms in the alkanediyl moiety, phenylalkyl, phenylalkylcarbonyl or phenylalkyloxycarbonyl, each of which has 1 to 4 carbon atoms in the straight-chain or branched alkyl moiety and each of which is monosubstituted or disubstituted in the phenyl moiety by identical or different substituents, or phenyl, phenylcarbonyl or phenyloxycarbonyl, each of which is optionally monosubstituted or disubstituted in the phenyl moiety by identical or different substituents, suitable phenyl substituents in each case being those mentioned in the case of $R^1$, $R^2$ furthermore represents phenyl, phenylcarbonyl, phenyloxycarbonyl, phenylcarbonyloxy or phenylaminocarbonylaminocarbonyloxy, each of which is optionally monosubstituted to trisubstituted by identical or different substituents, suitable phenyl substituents in each case being those mentioned in the case of $R^1$, $R^2$ furthermore represents heteroaryl, heteroarylcarbonyl, heteroaryloxycarbonyl, heteroarylcarbonyloxy, or heteroarylaminocarbonylaminocarbonyloxy, each of which has 2 to 9 carbon atoms and 1 to 3 identical or different hetero atoms—in particular nitrogen, oxygen and/or sulphur—in the heteroaryl moiety and each of which is optionally monosubstituted to trisubstituted by identical or different substituents, suitable heteroarl substituents in each case being the phenyl substituents mentioned in the case of $R^1$. Heteroaryl radicals which may be mentioned are pyridyl, furanyl, thiophenyl, piperidinyl or pyrrolyl, and $R^3$ represents $CF_3$, $X^1$, $X^2$, $X^3$ and $X^4$ independently of one another in each case represent hydrogen, chlorine, bromine, cyano, nitro, in each case straight-chain or branched alkyl, alkoxy, alkylthio, alkylsulphinyl or alkylsulphonyl, each of which has 1 to 4 carbon atoms, cycloalkyl having 3, 5 or 6 carbon atoms, in each case straight-chain or branched halogenoalkyl, halogenoalkoxy, halogenoalkylthio, halogenoalkylsulphinyl, halogenoalkylsulphonyl, each of which has 1 to 3 carbon atoms and 1 to 7 identical or different halogen atoms, or divalent dioxyalkylene having 1 to 3 carbon atoms which is optionally monosubstituted to tetrasubstituted by identical or different substituents from the series consisting of halogen and/or straight-chain or branched alkyl having 1 to 3 carbon atoms and/or straight-chain or branched halogenoalkyl having 1 to 3 carbon atoms and 1 to 7 identical or different halogen atoms, furthermore represent hydroxycarbonyl, in each case straight-chain or branched alkylcarbonyl or alkoxycarbonyl, each of which has 1 to 3 carbon atoms in the alkyl moiety, cycloalkyloxycarbonyl having 3, 5 or 6 carbon atoms in the cycloalkyl moiety, or amino or aminocarbonyl, each of which is optionally monosubstituted 1 or disubstituted by identical or different substituents, suitable amino substituents in each case being:

in each case straight-chain or branched alkyl having 1 to 3 carbon atoms, halogenoalkyl having 1 to 3 carbon atoms and 1 to 7 halogen atoms, alkoxyalkyl or alkylcarbonyl, each of which has 1 to 3 carbon atoms in the individual alkyl moieties, or phenylcarbonyl, phenylsulphonyl, phenylaminoncarbonyl or phenylmethylsulphonyl, each of which is optionally monosubstituted to trisubstituted in the phenyl moiety by identical or different substituents, suitable phenyl substituents in each case being those mentioned in the case of $R^1$;

furthermore represent phenyl, phenyloxy, phenylthio, phenylsulphinyl, phenylsulphonyl, phenylsulphonyloxy, phenylcarbonyl, phenyloxycarbonyl, phenylthiomethylsulphonyl or phenylazo, each of which is optionally monosubstituted to trisubstituted in the phenyl moiety by identical or different substituents, suitable suitable phenyl substituents in each case being those mentioned in the case of $R^1$, where at least one of the substituents $X^1$, $X^2$, $X^3$ or $X^4$ represents in each case straight-chain or branched halogenoalkyl (with the exception of the chloromethyl radical), halogenoalkoxy, halogenoalkylthio, halogenoalkylsulphinyl or halogenoalkylsulphonyl, each of which has 1 to 3 carbon atoms and 1 to 7 identical or different halogen atoms, straight-chain or branched alkylsulphonyl having 1 to 3 carbon atoms or divalent dioxyalkylene having 1 to 3 carbon atoms which is optionally monosubstituted to tetrasubstituted by identical or different substituents from the series consisting of halogen and/or straight-chain or branched alkyl having 1 to 3 carbon atoms and/or straight-chain or branched halogenoalkyl having 1 to 3 carbon atoms and 1 to 7 identical or different halogen atoms, furthermore represents hydroxycarbonyl, in each case straight-chain or branched alkylcarbonyl or alkoxycarbonyl, each of which has 1 to 3 carbon atoms in the alkyl moiety, cycloalkyloxycarbonyl having 3, 5 or 6 carbon atoms in the cycloalkyl moiety, or amino or aminocarbonyl, each of which is optionally monosubstituted or disubstituted by identical or different substituents, suitable amino substituents in each case being:

in each case straight-chain or branched alkyl having 1 to 3 carbon atoms, halogenoalkyl having 1 to 3 carbon atoms and 1 to 7 halogen atoms, alkoxyalkyl or alkylcarbonyl, each of which has 1 to 3 carbon atoms in the individual alkyl moieties, or phenylcarbonyl, phenylsulphonyl, phenylaminoncarbonyl or phenylmethylsulphonyl, each of which is optionally monosubstituted to trisubstituted in the phenyl moiety by identical or different substituents, suitable phenyl substituents being in each case those mentioned in the case of $R^1$;

furthermore represent phenyl, phenylthio, phenylsulphinyl, phenylsulphonyl, phenylsulphonyloxy, phenylcarbonyl, phenyloxycarbonyl, phenylthiomethylsulphonyl or phenylazo, each of which is optionally monosubstituted to trisubstituted in the phenyl moiety by identical or different substituents, suitable phenyl substituents in each case being those mentioned in the case of $R^1$.

The following substituted benzimidizoles of the general formula (I) may be mentioned individually in addition to the compounds mentioned in the preparation examples:

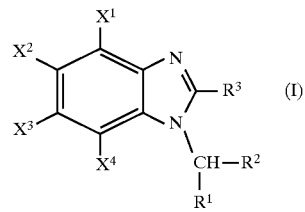

(I)

| $X^1$ | $X^2$ | $X^3$ | $X^4$ | $R^1$ | $R^2$ |
|---|---|---|---|---|---|
| Br | H | $Cl-CH_2-SO_2-$ | H | H | $\begin{array}{c} C_2H_5 \\ | \\ N \\ \diagdown COOC_2H_5 \end{array}$ |
| Br | H | $C_6H_5-S-CH_2-SO_2-$ | H | H | $\begin{array}{c} C_2H_5 \\ | \\ N \\ \diagdown COOC_2H_5 \end{array}$ |

-continued

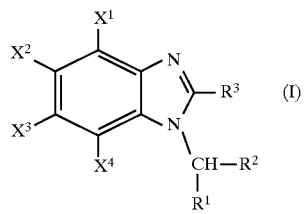

| X¹ | X² | X³ | X⁴ | R¹ | R² |
|---|---|---|---|---|---|
| H | p-CH₃—C₆H₄—SO₂—O— | p-CH₃—C₆H₄—SO₂—O— | H | H | —N(C₂H₅)(COOC₂H₅) |
| Br | H | C₆H₅—O—CO— | H | H | —N(C₂H₅)(COOC₂H₅) |
| Br | H | cyclohexyl-O—C(=O)— | H | H | —N(C₂H₅)(COOC₂H₅) |
| Br | H | n-C₆H₁₃—O—CO— | H | H | —N(C₂H₅)(COOC₂H₅) |
| Br | H | C₆H₅—CO— | H | H | —N(C₂H₅)(COOC₂H₅) |
| Br | H | F₃C—S— | H | H | —N(C₂H₅)(COOC₂H₅) |
| Cl | H | F₃C—S— | H | H | —N(C₂H₅)(COOC₂H₅) |
| COO—C₆H₅ | H | F₃C—O— | H | H | —O—C₂H₅ |
| cyclohexyl-O—C(=O)— | H | CF₃ | H | H | —N(C₂H₅)(COOC₂H₅) |
| cyclohexyl-O—C(=O)— | H | F₃C—O— | H | H | —N(C₂H₅)(COOC₂H₅) |
| Br | H | ClFCH—CF₂—S— | H | H | —N(C₂H₅)(COOC₂H₅) |
| Br | H | ClFCH—CF₂—S— | H | H | —O—C₂H₅ |
| Br | H | F₃C—CHF—CF₂—S— | H | H | —N(C₂H₅)(COOC₂H₅) |
| Br | H | F₃C—CHF—CF₂—S— | H | H | —O—C₂H₅ |
| CF₃ | H | CF₃ | H | H | —N(C₂H₅)(COOC₂H₅) |
| CF₃ | H | CF₃ | H | H | —O—C₂H₅ |

-continued

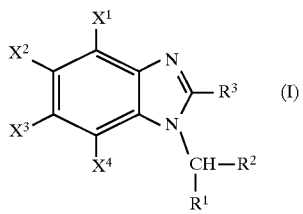

| $X^1$ | $X^2$ | $X^3$ | $X^4$ | $R^1$ | $R^2$ |
|---|---|---|---|---|---|
| COO-n-$C_3H_7$ | H | $CF_3$ | H | H | $-N(C_2H_5)(COOC_2H_5)$ |
| COO-i-$C_3H_7$ | H | $CF_3$ | H | H | $-N(C_2H_5)(COOC_2H_5)$ |
| COO-n-$C_4H_9$ | H | $CF_3$ | H | H | $-N(C_2H_5)(COOC_2H_5)$ |
| COO-s-$C_4H_9$ | H | $CF_3$ | H | H | $-N(C_2H_5)(COOC_2H_5)$ |
| COO—$C_6H_5$ | H | $CF_3$ | H | H | $-N(C_2H_5)(COOC_2H_5)$ |
| COO-s-$C_4H_9$ |   | $F_3C-O-$ | H | H | $-O-C_2H_5$ |
| COO-n-$C_3H_7$ | H | $CF_3$ | H | H | $-O-C_2H_5$ |
| COO-i-$C_3H_7$ | H | $CF_3$ | H | H | $-O-C_2H_5$ |
| COO-n-$C_4H_9$ | H | $CF_3$ | H | H | $-O-C_2H_5$ |
| COO-s-$C_4H_9$ | H | $CF_3$ | H | H | $-O-C_2H_5$ |
| COO—$C_6H_5$ | H | $CF_3$ | H | H | $-O-C_2H_5$ |
| COO-n-$C_3H_7$ | H | $F_3C-O-$ | H | H | $-N(C_2H_5)(COOC_2H_5)$ |
| COO-i-$C_3H_7$ | H | $F_3C-O-$ | H | H | $-N(C_2H_5)(COOC_2H_5)$ |
| COO-n-$C_4H_9$ | H | $F_3C-O-$ | H | H | $-N(C_2H_5)(COOC_2H_5)$ |
| COO-s-$C_4H_9$ | H | $F_3C-O-$ | H | H | $-N(C_2H_5)(COOC_2H_5)$ |
| COO—$C_6H_5$ | H | $F_3C-O-$ | H | H | $-N(C_2H_5)(COOC_2H_5)$ |
| COO-n-$C_3H_7$ | H | $F_3C-O-$ | H | H | $-O-C_2H_5$ |
| COO-i-$C_3H_7$ | H | $F_3C-O-$ | H | H | $-O-C_2H_5$ |
| COO-n-$C_4H_9$ | H | $F_3C-O-$ | H | H | $-O-C_2H_5$ |

The 1H-benzimidazoles of the formula (II) mentioned in the preparation of the substituted benzimidazoles of the formula (I) can also be employed as pesticides, just like the compounds of the formula (I). 1H-Benzimidazoles of the formula (II) which are preferably mentioned are those in which the substituents have the preferred and particularly preferred meanings mentioned in the case of the compounds of the formula (I). The following compounds of the formula (II) are mentioned individually:

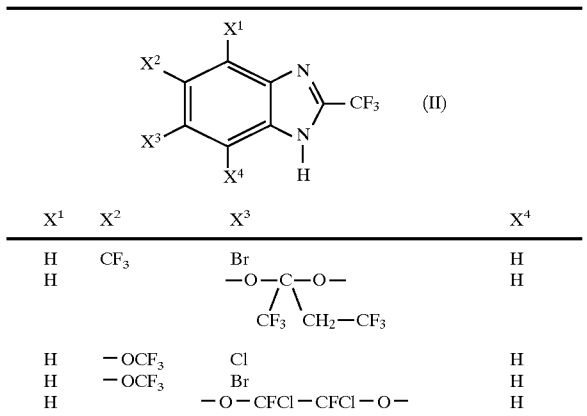

| $X^1$ | $X^2$ | $X^3$ | $X^4$ |
|---|---|---|---|
| H | $CF_3$ | Br | H |
| H | | $-O-C-O-$ / \ $CF_3$ $CH_2-CF_3$ | H |
| H | $-OCF_3$ | Cl | H |
| H | $-OCF_3$ | Br | H |
| H | | $-O-CFCl-CFCl-O-$ | H |

If, for example, 5(6)-phenyl-2-trifluoromethyl-benzimidazole and chloromethyl ethyl ether are used as starting compounds, the course of the reaction of the process according to the invention can be represented by the following equation:

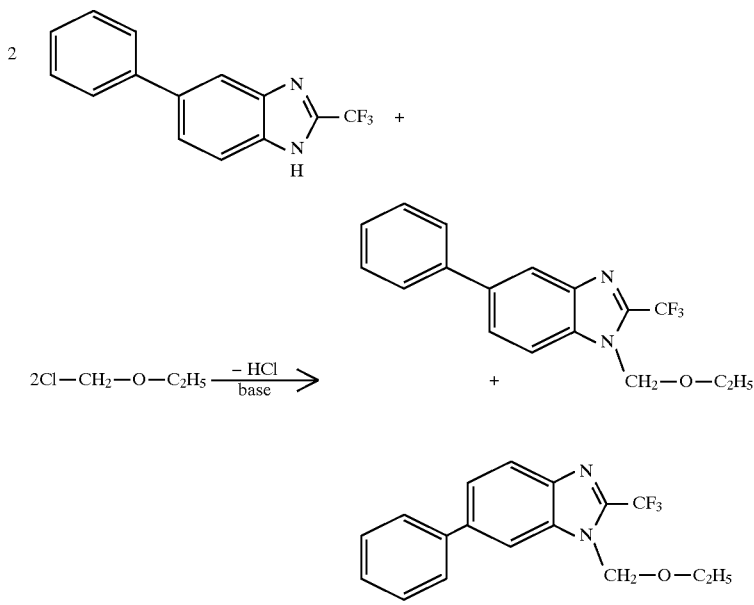

Formula (II) provides a general definition of the 1H-benzimidazoles required as starting substances for carrying out the process according to the invention. In this formula (II), $R^3$, $X^1$, $X^2$, $X^3$ and $X^4$ preferably represent those radicals which have already been mentioned in connection with the description of the compounds of the formula (I) according to the invention as being preferred for these substituents.

The 1H-benzimidazoles of the formula (II) are known or can be obtained in analogy to known processes (cf., for example, J. Amer. Chem. Soc. 75, 1292 [1953]; U.S. Pat. No. 3,576,818).

Formula (III) provides a general definition of the compounds furthermore required as starting materials for carrying out the process according to the invention.

In this formula (III), $R^1$ and $R^2$ preferably represent those radicals which have already been mentioned in connection with the description of the substances of the formula (I) according to the invention as being preferred for these substituents.

A preferably represents a leaving radical customary in alkylating agents, preferably halogen, in particular chlorine, bromine or iodine, or in each case optionally substituted alkylsulphonyloxy, alkoxysulphonyloxy or arylsulphonyloxy, such as, in particular, methanesulphonyloxy, trifluoromethanesulphonyloxy, methoxysulphonyloxy, ethoxysulphonyloxy or p-toluenesulphonyloxy.

A furthermore also represents an alcohol, alkanoyloxy or alkoxy group, such as, for example, a hydroxyl, acetoxy or methoxy group.

The compounds of the formula (III) are known or can be obtained in analogy to known processes (cf., for example, DE 2,040,175; DE 2,119,518; Synthesis 1273, 703).

Suitable diluents for carrying out the process according to the invention are inert organic solvents. These include, in particular, aliphatic, alicyclic or aromatic, optionally halogenated hydrocarbons, such as, for example, benzine, benzene toluene, xylene, chlorobenzene, dichlorobenzene, petroleum ether, hexane cyclohexane, dichloromethane, chloroform or carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitrites, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, or bases, such as pyridine, or organic acids, such as formic acid or acetic acid.

The process according to the invention is preferably carried out in the presence of a suitable reaction auxiliary. Suitable reaction auxiliaries are all customary inorganic or organic bases. These include, for example, the hydrides, hydroxides, amides, alcoholates, acetates, carbonates or hydrogencarbonates of alkaline earth metals or alkali metals, such as, for example, sodium hydride, sodium amide, lithium diethylamide, sodium methylate, sodium ethylate, potassium tert.-butylate, sodium hydroxide, potassium hydroxide, ammonium hydroxide, sodium acetate, potassium acetate, calcium acetate, ammonium acetate, sodium carbonate, potassium carbonate, potassium hydrogencarbonate, sodium hydrogencarbonate or ammonium carbonate, organolithium compounds, such as n-butyllithium, and also tertiary amines, such as trimethylamine, triethylamine, tributylamine, di-isopropylethylamine, tetramethylguanidine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

In those cases where A in formula (III) represents an alcohol, alkanoyloxy or alkoxy group, other suitable reaction auxiliaries are organic or inorganic acids, such as, for example sulphuric acid, hydrochloric acid, p-toluenesulphonic acid, perfluorobutanesulphonic acid or strongly acidic ion exchangers.

If appropriate, the process according to the invention can also be carried out in a two-phase system, such as, for example, water/toluene or water/dichloromethane, if appropriate in the presence of a suitable phase-transfer catalyst Examples of such catalysts which may be mentioned are: tetrabutylammonium iodide, tetrabutylammonium bromide, tetrabutylammonium chloride, tributyl-methyl-phosphonium bromide, trimethyl-$C_{13}$/$C_{15}$-alkylammonium chloride, trimethyl-$C_{13}$/$C_{15}$-alkylammonium bromide, dibenzyl-dimethyl-ammonium methylsulphate, dimethyl-$C_{12}$/$C_{14}$alkylbenzylammonium chloride, dimethyl-$C_{12}$/$C_{14}$-alkyl-benzylammonium bromide, tetrabutyl ammonium hydroxide, triethylbenzylammonium chloride, methyltrioctylammonium chloride, trimethylbenzylammonium chloride, 15-crown-5, 18-crown-6 or tris-[2-(2-methoxyethoxy)-ethyl]-amine.

When carrying out the process according to the invention, the reaction, temperatures can be varied within a substantial range. In general, the process is carried out at temperatures between −70° C. and +200° C., preferably at temperatures between 0° C. and 130° C.

The process according to the invention is conventionally carried out under atmospheric pressure. However, it can also be carried out under increased or reduced pressure.

To carry out the process according to the invention, 1.0 to 5.0 mol, preferably 1.0 to 2.5 mol, of compound of the formula (III) and, if appropriate, 0.01 to 5.0 mol, preferably 1.0 to 3.0 mol, of reaction auxiliary are generally employed per mole of 1H-benzimidazole of the formula (II).

In a particular embodiment, it is also possible to first silylate the 1H-benzimidazoles of the formula (II) in a preceding reaction step with the aid of conventional silylation processes, for example using hexamethyldisilazane or trimethylsilyl chloride, if appropriate in the presence of a suitable catalyst, such as, for example, sulphuric acid, trifluoroacetic acid, ammonium sulphate, imidazole or saccharin, at temperate between −20° C. and +50° C., and to react the 1-trimethylsilylbenzimidazoles thus obtainable in a subsequent second step with alkylating agents of the formula (II) using the process according to the invention. In this case, it is advantageous to add tin tetrachloride to the alkylation reaction to act as a catalyst (cf., for example, Chem. Heterocycl. Comp. USSR 24, 514 [1988])

The reaction is carried out and the reaction product is worked up and isolated by known processes (cf. in this context also the preparation examples).

The end products of the formula (I) are purified with the aid of conventional processes, for example by column chromatography or by recrystallization.

They are characterized with the aid of the melting point or, in the case of compounds which do not form crystals —in particular in the case of regioisomer mixtures—, with the aid of proton nuclear resonance spectroscopy ($^1$H-NMR).

The active compounds are suitable for combating animal pests, preferably arthropods and nematodes, in particular insects and arachnids encountered in agriculture, in forests, in the protection of stored products and materials, and in the hygiene sector. They are active against normally sensitive and resistant species and against all or some stages of development.

The abovementioned pests include:

From the order of the Isopoda, for example, *Oniscus asellus, Armadillidium vulgare* and *Porcellio scaber;* from the order of the Diplopoda, for example, *Blaniulus guttulatus;* from the order of the Chilopoda, for example, *Geophilus carpophagus* and *Scutigera spec;* from the order of the Symphyla, for example, *Scutigerella immalata;* from the order of the Thysanura, for example, *Lepismna saccharina;* from the order of the Collembola, for example, *Onychiumis armatus;* from the order of the Orthoptera, for example, *Blatta orientalis, Periplaneta americana, Leucophaea maderae, Blattella germanica, Acheta domesticus, Gryllotalpa spp., Locusta migratoria* migratorioides, *Melanoplus differentialis* and *Schistocerca gregaria;* from the order of the Dermaptera, for example, *Forficula auricularia;* from the order of the Isoptera, for example, *Reticulitermes spp.;* from the order of the Anoplura, for example, *Phylloxera vastatix, Pemphigus spp.,* Pediculus humanus corporis, *Haematopinus spp.* and *Linognaius spp.;* from the order of the Mallophaga, for example, *Trichodectes spp.* and *Damalinea spp.;* from the order of the Thysanoptera, for example, *Hercinothrips femoralis* and *Thrips tabaci;* from the order of the Heteroptera, for example, *Eurigaster spp., Dysdercus intermedius, Piesma quadrata, Cimex lectularius, Rhodnius prolixus* and *Triatoma spp.;* from the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi, Emrpasca spp., Euscelis bilobatus, Nephotettix cincticeps, Leanium comi, Saissetia oleae, Laodelphax striatellus, Nilaparvata lugens, Aonidiella auranti, Aspidiotus hederae, Pseudococcus spp.* and *Psylla spp.;* from the order of the Lepidoptera, for example, *Pectinophora gossypiella, Bupalus piniarius, Cheimatobia brumata Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia. spp., Earias insulana, Heliothis spp., Laphygma exigua, Mamestra brassicae, Panolis flammea, Prodena litura, Spodoptera spp., Trichoplusia ni, Carpocapsa pomonella, Pieris spp., Chilo spp.,*

*Pyrausta nubilalis, Ephestia kuehniella, Galleria mellonella, Tineola bisselliella, Tinea pellionella, Hofmannophila pseudospretella, Cacoecia podana, Capua reticulana, Choristoneura filiferana, Clysia ambiguella, Homona magnanamia* and *Tortix viridana;* from the order of the Coleoptera, for example, *Anobium punctaturn, Rhizopertha dominica, Bruchidius obtectus, Acanthoscelides obtectus, Hylotrupes bajulus, Agelastica alni, Leptinotarsa decemlineaa, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica;* from the order of the Hymenoptera, for example, *Diprion spp., Hoplocampa spp., Lasius spp., Monomorium pharaonis* and *Vespa spp.;* from the order of the Diptera, for example, *Aedes spp., Anopheles spp., Culex spp., Drosophila melanogaster, Musca spp., Fannia spp., Calliphora erytrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa;* from the order of the Siphonaptera, for example, *Xenopsylla cheopis. Ceratophyllus spp.;* from the order of the Arachnidf for example, *Scorpio maurus* and *Latrodectus mactans;* from the order of the Acarina, for example, *Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa,. Panonychus spp.* and *Tetranychus spp.*

The plant-parasitic nematodes include *Pratylenchus spp., Radopholus similis, Ditylenchus dipsaci, Tylenchulus semipenetrans, Heterodera spp., Meloidogyne spp., Aphelenchoides spp., Longidorus spp., Xiphinema spp., Trichodorus spp.*

The active compounds according to the invention are not only active against plant, hygiene and stored product pests, but also, in the veterinary medicine sector, against animal parasites (ectoparasites and endoparasites) such as scaly ticks, Argasidae, scab mites, Trombidae, flies (stinging and sucking), parasitic fly larvae, lice, hair lice, bird lice, fleas and endoparasitic worms.

They are active against normally-sensitive and resistant species and strains and against all parasitic and non-parasitic development stages of the ecto- and endoparasites.

The active compounds according to the invention are distinguished by a powerful insecticidal activity.

They can be employed particularly successfully for combating plant-injurious insects, such as, for exarnple, against the larvae of the mustard beetle (*Phaedon cochleariae*) or against the caterpillars of the cabbage moth (*Plutella maculipennis*) or against other Plutella species, such as, for example, *Plutella xylostella*, or against the tobacco bud worm (*Heliothis virescens*) and for combating plant-injurious mites, such as, for example, against the greenhouse red spider mite (*Tetranychus urticae*), or for combating plant-injurious nematodes, such as, for example, against the nematode species *Globodera rostochiensis.*

In addition, the active compounds according to the invention can also be employed for combating hygiene and stored product pests, such as, for example, against the house fly (*Musca domestica*) or against the grain weevil (*Sitophilus granarius*) or against cockroach species, such as, for example; *Blattella germmnica* or *Periplaneta americana.*

Moreover, the active compounds according to the invention can be employed particularly successfully for combating parasitic pests of warm-blooded species, such as, for example, against scab mites (*Psoroptes ovis*).

In addition, the active compounds according to the invention also have a powerful fungicidal activity and can be employed in practice for combating undesired microorganisms. The active compounds are also suitable for use as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubense;*

Plasmopara species, such as, for example, *Plasmopara viticola;*

Peronospora species, such as, for example, *Peronospora pisi* or *Peronospora brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaealis;*

Pyrenophora species, such as, for example, *Pyrenophora teres* or *Pyrenophora gramnmea* (conidia form: Drechslera, synonym: Helminthosporium);

Cochliobolus species, such as, for example, *Cochliobolus sativus* (conidia form: Drechslera, synonym: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particular success for combating cereal diseases such as, for example, against the causative organism of powdery mildew of cereals (*Erysiphe graminis*) or for combating diseases in fruit and vegetable growing such as, for example, against the causative organism of tomato blight (*Phytophthora infestans*) or against the causative organism of downy mildew of grapevine (*Plasmopara viticola*), or for combating rice diseases such as, for example, against the causative organism of rice blast disease (*Pyricularia oryzae*).

Moreover, if used at appropriate application rates, the active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, icaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanurn, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisurn, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicur, Saccharum Ananas, Asparagus and Alliur.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be employed with particular success here for combating monocotyledon and dicotyledon weeds in monocotyledon and dicotyledon cultures, such as, for example, maize, wheat or soya.

Depending on their particular physical and/or chemical properties, the active compounds can be converted into the customary formulations, such as solutions, emulsions, suspensions, powders, foams, pastes, granules, aerosols, natral and synthetic materials impregnated with active compound, very fine capsules in polymeric substances and in coating compositions for seed, furthermore in formulations used with burning equipment, such as fumigating cartridges, fumigating cans and fumigating coils and the like, as well as ULV cold- and warm-mist formulations.

These formulations are produced in a known manner, for example by mixing the active compounds with extenders, that is liquid solvents, liquefied gases under pressure and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobezenes, chloroethylenes or methylene chloride, alithatic hydrocarbons, such as cyclohexane or paraffins, for example petroleum fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl suLphoxide, as well as water; by liquefied gaseous extenders or carriers there are meant liquids which are gaseous at normal temperature and under atmospheric pressure, for example aerosol propellants, such as halogenohydrocarbons as well as butane, propane, nitrogen and carbon dioxide; as solid carriers there are suitable: for example ground natral minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable, for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty lcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and tin.

The formulations in general contain between 0.1 and 95 percent by weight of active compound, preferably between 0.5 and 90%.

The active compounds according to the invention can be present in their commercially available formulations and the use forms prepared with these formulations as a miture with other active comnpounds, such as insecticides, attractants, sterilants, acaricides, nematicides, fimgicides, growth-regulating substances or herbicides. The insecticides include, for exarmple, phosphates, carbamates, carboxylates, chlorinated hydrocarbons, phenylureas and substances, produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95 percent by weight of active compound, preferably between 0.0001 and 1 percent by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds which can be used according to the invention are also suitable for combating insects, mites, ticks etc. in the sector of animal keeping and cattle breeding, better results, for example higher milk production, greater weight, more attractive animal pelt, longer life etc., can be achieved by combating the pests.

The application of the active compounds which can be used according to the invention occurs in this sector in a known fashion, for example, by oral application in the form of, tablets, capsules, potions or granules, by means of deamal or external application in the form of, for example, dipping, spraying, pouring-on, spotting-on and dusting, as well as by means of parenteral application in the form of, for example, injection, and, furthermore, by means of the feed-through process. In addition, application as moulded articles (collar, ear tag) is also possible.

When used as fungicides, the active compounds according to the invention can also be present in the formulations as a mixture with other known active compounds, such as fungicides, insecticides, acaricides and herbicides, and in mixtures with fertilizers and growth regulators.

When used as fungicides, the active compounds can be used as such, in the form of their formulations, or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

When used as fungicides in the treatment of parts of plants, the active compound concentrations in the use forms can be varied within a substantial range. They are, in general, between 1 and 0.0001% by weight, preferably between 0.5 and 0.001% by weight.

When used as fungicides in the treatment of seed, amounts of active compound of 0.001 to 50 g per kilogram of seed, preferably 0.01 to 10 g, are generally required.

When used as fungicides in the tretment of soil, active compound concentrations of 0.00001 to 0.1% by weight, preferably 0.0001 to 0.02% by weight, are required at the place of action.

When used as herbicides, the active compounds according to the invention, as such or in the form of their formulations, can also be used as a mixture with known herbicides for combating weeds, finished formulations or tank mixes being possible. Suitable herbicides for the mixtures are known herbicides, for example anilides such as, for example, diflufenican and propanil; arylcarboxylic acids such as, for example, dichloropicolinic acid, dicamba or picloram; aryloxyalkanoic acids such as, for example, 2,4-D, 2,4DB, 2,4DP, fluroxypyr, MCPA, MCPP and triclopyr, aryloxy-phenoxy-alkanoic esters such as, for example, diclofop-methyl, fenoxaprop-ethyl, fluazifop-butyl, haloxyfop-methyl and quizalofopethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trfiuralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydirn and tralkoxydim; imidazolinones such as, for example, imazethapyr, imazamethabenz, imazapyr and imazaquin nitriles such as, for example, bromoxynil, dichlobenil and ioxynil; oxyacetamides such as, for example, mefenacet; sulphonylureas such as, for example, amidosufibron, bensulfuron-methyl, chlorimuron-thyl, chlorsuliron, cinosuluron, metsulfuron-metiyl, nicosultfuron, primiulfiron, pyrazosulfinethyl, thifensulfuron-methyl, triasulfuron and tribeuron-methyl; thiocarbamates such as, for example, butylate, cycloate, di-allate, EPTC, esprocarb, molinate, prosulfocarb, thiobencarb and tri-allate; triazines such as, for example, atrzine, cyanine, simazine, simetryn, terbutyn and terbutylazine; triazinones such as, for example, hexazinone, metarnitron and metribuzin; others such as, for example aminotriazole, benfuiresate, bentazone, cinmethylin, clomazone, clopyralid, difenzoquat, dithiopyr, ethofiimesate, fluorochloridone, glufosinate, glyphosate, isoxabe pynidate, quinchlorac, quirnmerac, sulphosate and tridiphane.

When used as herbicides, a mixtue with other known active compounds, such as fungicides, insecticides, acaricides, nematocides, bird repellants, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

When used as herbicides, the active compounds according to the invention can be applied either before or after emergence of the plants. They can also be incorporated into the soil before sowing.

When used as herbicides, the amount of active compound used can vary within a substantial range. It depends essentially on the nature of the desired effect. In general, the amounts used are between 0.001 and 10 kg of active compound per hectare of soil surface, preferably between 0.005 and 5 kg per hecare.

The preparation and use of the active compounds according to the invention can be seen from the following Examples.

PREPERATION EXAMPLES

Example 1

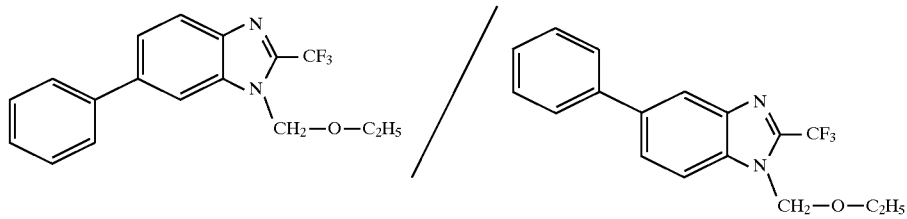

7.9 g (0.03 mol) of 5(6)phenyl-2-trifiuoromethyl-1H-benziniidazole and 8.2 g (0.06 mol) of pulveriz potassium carbonate are refluxed for 15 minutes in 70 ml of ethyl acetate, and the mixture is subsequently treated with 3.9 g (0.04 mol) of (chloromethyl ethyl ether 20 ml of ethyl acetate and refluxed for a further 4 hours, with stiring. For working up, the cooled reaction mixture is washed twice using in each case 40 ml of water, dried over sodium sulphate, and concentrated in vacuo, and the residue is purified by chromatography over silica gel (eluent: dichlorometane).

6.9 g (71% of theory) of 1-ethoxymethyl-5(6)phenyl-2-tifiuoromethyl-benzimidazole are obtained as a regioisomer mixture in a ratio of 1:1.

$^1$H-NMR (DMSO$_6$/tetrarethysitane):d=5.84 (s, 2H); 5.89 (s, 2H) ppm [in each case N-CH$_2$—O—].

The following substituted benzimidazoles of the general formula (I) are obtained in a corresponding manner and following the general preparation instructions:

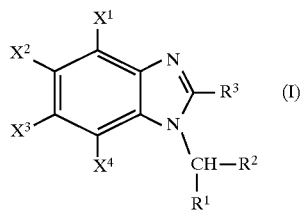

| Ex. No. | X$^1$ | X$^2$ | X$^3$ | X$^4$ | R$^1$ | R$^2$ | Physical Properties |
|---|---|---|---|---|---|---|---|
| 2 | Br | H | CF$_3$ | H | H | —N(CH$_3$)—C(=O)—OCH$_3$ | m.p. 90–90° C. |
| 3 | Br | H | CF$_3$ | H | H | —N(C$_2$H$_5$)—C(=O)—OCH$_3$ | m.p. 70–74° C. |
| 4 | Br | H | CF$_3$ | H | H | —N(n-C$_3$H$_7$)—C(=O)—OCH$_3$ | m.p. 75–79° C. |
| 5 | Br (H) | H (CF$_3$) | CF$_3$ (H) | H (Br) | H | —CH=CH$_2$ | m.p. 53–56° C. (82:18) |
| 6 | Br | H | CF$_3$ | H | H | —CO—C(CH$_3$)$_3$ | m.p. 120–123° C. |
| 7 | Br | H | CF$_3$ | H | H | —CH$_2$—C$_6$H$_5$ | m.p. 80–84° C. |
| 8 | Br | H | CF$_3$ | H | H | —CO—C$_6$H$_5$ | m.p. 163–166° C. |
| 9 | Br (H) | H (CF$_3$) | CF$_3$ (H) | H (Br) | H | —CH=CH—CH$_3$ | m.p. 80–83° C. (93:7) |

-continued

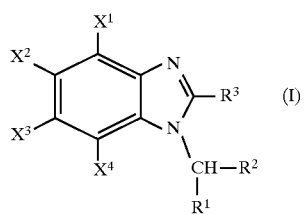

| Ex. No. | X¹ | X² | X³ | X⁴ | R¹ | R² | Physical Properties |
|---|---|---|---|---|---|---|---|
| 10 | Br | H | CF₃ | H | H | ~CH=C(Cl)(CH₃) | m.p. 60–63° C. (E/Z = 64:36) |
| 11 | H | (CH₃)₂N—CO— (H) | H ((CH₃)₂N—CO—) | H | H | —O—C₂H₅ | ¹H-NMR*): 5.59; 5.60; 7.54–8.62 |
| 12 | H | F₂CH—CF₂—O— (H) | H (F₂CH—CF₂—O—) | H | H | —O—C₂H₅ | |
| 13 | Br (H) | H (CF₃) | CF₃ (H) | H (Br) | H | —O-i-C₃H₇ | ¹H-NMR*): 5.94; 6.00 (63:37) |
| 14 | Br (H) | H (CF₃) | CF₃ (H) | H (Br) | H | —O-n-C₃H₇ | m.p. 70–73° C. (76:24) |
| 15 | Br (H) | H (CF₃) | CF₃ (H) | H (Br) | H | —O—(CH₂)₃—C₆H₅ | ¹H-NMR*): 5.94; 6.00 (64:36) |
| 16 | Br | H | CF₃ | H | H | —O—CH₂—C≡CH | m.p. 71–73° C. |
| 17 | Br | H | CF₃ | H | H | —O—C(=O)—NH—C(=O)—NH—C₆H₄—Cl | m.p. 195–200° C. |
| 18 | Br | H | CF₃ | H | H | —O—CO—C(CH₃)₃ | m.p. 98–101° C. |
| 19 | Br (H) | H (CF₃) | CF₃ (H) | H (Br) | H | —O—CH₂—C₆H₄—Cl (m-) | ¹H-NMR*): 6.08; .14 (70:30) |
| 20 | Br (H) | H (CF₃) | CF₃ (H) | H (Br) | H | —O—C₂H₅ | m.p. 82–85° C. (87:13) |
| 21 | Br | H | CF₃ | H | H | —N(CH₃)—C(=O)—OC₂H₅ | m.p. 128–130° C. |
| 22 | Br | H | CF₃ | H | H | CN | m.p. 147–151° C. |
| 23 | H | C₆H₅—CO— (H) | H (C₆H₅—CO—) | H | H | —O—C₂H₅ | ¹H-NMR*): 5.89 (1:1) |
| 24 | H | C₆H₅—CO— (H) | H (C₆H₅—CO—) | H | H | —N(CH₃)—C(=O)—OCH₃ | m.p. 105–109° C. (1:1) |

-continued

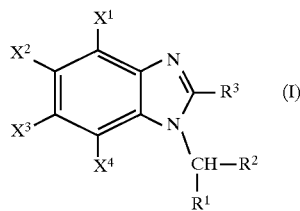
(I)

| Ex. No. | X¹ | X² | X³ | X⁴ | R¹ | R² | Physical Properties |
|---|---|---|---|---|---|---|---|
| 25 | H | C₆H₅—CO— (H) | H (C₆H₅—CO—) | H | H | CN | m.p. 102–105° C. (1:1) |
| 26 | H | C₆H₅ (H) | H (C₆H₅) | H | H | —N(CH₃)—C(O)—OCH₃ | ¹H-NMR*): 6,02; 5,98 (40:60) |
| 27 | Br (H) | H (CF₃) | CF₃ (H) | H (Br) | H | —O—CH₂—CH₂—O—CH₃ | ¹H-NMR*): 5.94; 6.03 |
| 28 | Br | H | CF₃ | H | H | —N(C₂H₅)—C(O)—OC₂H₅ | m.p. 103–106° C. |
| 29 | Br | H | CF₃ | H | H | —N(n-C₃H₇)—C(O)—OC₂H₅ | m.p. 92–94° C. |
| 30 | Br | H | CF₃ | H | H | —N(i-C₃H₇)—C(O)—OC₂H₅ | m.p. 70–73° C. |
| 31 | Br | H | CF₃ | H | H | —N(CH₂—C₆H₅)—C(O)—OC₂H₅ | m.p. 70–74° C. |
| 32 | Br | H | CF₃ | H | H | —N(C₂H₅)—C(O)—O-i-C₄H₉ | m.p. 70–73° C. |
| 33 | H | —O—(CH₂)₃—O— | | H | H | —O—C₂H₅ | m.p. 70–74° C. |
| 34 | Br | H | CF₃ | H | H | —N(CH₃)₂ | (x HCl) |
| 35 | H | —O—(CH₂)₃—O— | | H | H | —N(CH₃)—C(O)—OCH₃ | m.p. 105–108° C. |
| 36 | Br | H | CF₃ | H | H | —N(c-C₆H₁₁)—C(O)—OC₂H₅ | m.p. 80–83° C. |

-continued
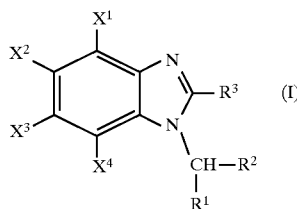
| Ex. No. | X¹ | X² | X³ | X⁴ | R¹ | R² | Physical Properties |
|---|---|---|---|---|---|---|---|
| 37 | Br | H | CF₃ | H | H | −N(C₆H₅)−C(=S)−OC₂H₅ | m.p. 135–136° C. |
| 38 | Br | H | CF₃ | H | H | −N(CH₂−CH=CH₂)−C(=O)−OC₂H₅ | m.p. 76–78° C. |
| 39 | Br | H | CF₃ | H | H | −N(C₆H₅)−C(=S)−OC₂H₅ | m.p. 174–176° C. |
| 40 | Br | H | CF₃ | H | H | −N(CH₂−CH(CH₃)₂)−C(=O)−OC₂H₅ | m.p. 109–112° C. |
| 41 | Br (H) | H (CF₃) | CF₃ (H) | H (Br) | H | −S−CH₃ | m.p. 56–60° C. (1:1) |
| 42 | H | CF₃ (Cl) | Cl (CF₃) | H | H | −COOC₂H₅ | |
| 43 | H | CF₃ | Cl | H | H | 2-Cl-C₆H₄ | |
| 44 | H | Cl | CF₃ | H | H | 2-Cl-C₆H₄ | |
| 45 | H | CF₃ | Cl | H | H | 2,4-Cl₂-C₆H₃ | |
| 46 | H | Cl | CF₃ | H | H | 2,4-Cl₂-C₆H₃ | |

-continued

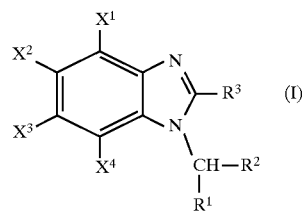

| Ex. No. | X¹ | X² | X³ | X⁴ | R¹ | R² | Physical Properties |
|---|---|---|---|---|---|---|---|
| 47 | H | CF₃ (Cl) | Cl (CF₃) | H | H | 4-NO₂-C₆H₄- | |
| 48 | H | CF₃ (Cl) | Cl (CF₃) | H | H | -P(=O)(OC₂H₅)(OC₂H₅) | |
| 49 | H | CF₃ (Cl) | Cl (CF₃) | H | H | 3-CF₃-C₆H₄- | |
| 50 | H | CF₃ (Cl) | Cl (CF₃) | H | -O-C₂H₅ | -O-C₂H₅ | m.p. 90–92° C. |
| 51 | H | CF₃ (Cl) | Cl (CF₃) | H | H | -CO-C(CH₃)₃ | |
| 52 | H | Cl | CF₃ | H | H | CN | |
| 53 | H | CF₃ | Cl | H | H | CN | |
| 54 | H | CF₃ (Cl) | Cl (CF₃) | H | H | -CO-NH₂ | |
| 55 | H | CF₃ (Cl) | Cl (CF₃) | H | H | -CO-C₆H₅ | |
| 56 | H | CF₃ (Cl) | Cl (CF₃) | H | H | -OCH(CH₃)₂ | ¹H-NMR*): A: 5.66; 7.83; 8.23 B: 5.71; 8.00; 8.06 |
| 57 | H | CF₃ (Cl) | Cl (CF₃) | H | H | -CO-(4-F-C₆H₄) | ¹H-NMR*): A: 5.67; 7.43; 8.33 B: 5.73; 7.63; 8.10 |
| 58 | H | CF₃ (Cl) | Cl (CF₃) | H | H | -CO-(4-C₆H₅-C₆H₄) | ¹H-NMR*): A: 5.75; 7.45; 8.30 B: 5.78; 7.75; 7.97 |
| 59 | H | CF₃ (Cl) | Cl (CF₃) | H | H | -CO-(2-CH₃-4-Cl-5-CH₃-C₆H₂) | ¹H-NMR*): A: 5.60; 7.41; 8.28 B: 5.63; 7.63; 8.06 |
| 60 | H | CF₃ (Cl) | Cl (CF₃) | H | H | -CO-(2-Cl-4-Cl-C₆H₃) | ¹H-NMR*): A: 5.71; 7.42; 8.28 B: 5.75; 7.66; 8.06 |

-continued

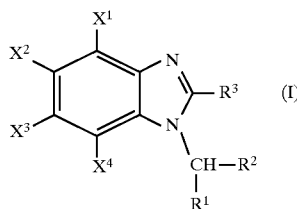

| Ex. No. | $X^1$ | $X^2$ | $X^3$ | $X^4$ | $R^1$ | $R^2$ | Physical Properties |
|---|---|---|---|---|---|---|---|
| 61 | H | CF₃ (Cl) | Cl (CF₃) | H | H | 3,5-dichlorobenzoyl | $^1$H-NMR*): A: 5.67; 7.39; 8.29 B: 5.73; 7.60 and 8.05 |
| 62 | H | CF₃ (Cl) | Cl (CF₃) | H | H | 4-bromobenzoyl | $^1$H-NMR*): A: 5.83; 7.68; 8.25 B: 5.90; 7.75; 8.03 |
| 63 | H | CF₃ (Cl) | Cl (CF₃) | H | H | 4-chloro-2-methylbenzoyl | $^1$H-NMR*): A: 5.60; 7.38; 8.26 B: 5.64; 7.62 and 8.04 |
| 64 | H | CF₃ (Cl) | Cl (CF₃) | H | H | (2,3-dichlorophenyl)acetyl | $^1$H-NMR*): A: 5.30; 7.54; 8.22 B: 5.35; 7.75; 8.02 |
| 65 | H | CF₃ (Cl) | Cl (CF₃) | H | H | (3,4-dichlorophenyl)acetyl | $^1$H-NMR*): A: 5.11; 7.15; 8.23 B: 5.15; 7.40; 8.02 |
| 66 | H | CF₃ (Cl) | Cl (CF₃) | H | CH₃ | CN | $^1$H-NMR*): A; 5.60; 7.80; 8.34 B: 5.65; 7.96; 8.13 |
| 67 | H | CF₃ (Cl) | Cl (CF₃) | H | H | N(C₂H₅)C(O)OCH₃ | $^1$H-NMR*): A: 5.86; 7.98; 8.33 B: 5.90; 8.03; 8.21 |
| 68 | H | CF₃ (Cl) | Cl (CF₃) | H | H | N(n-C₄H₉)C(O)OC₂H₅ | $^1$H-NMR*): A: 5.85; 7.99; 8.32 B: 5.90; 8.02; 8.22 |
| 69 | H | CF₃ (Cl) | Cl (CF₃) | H | H | N(CH₃)C(O)OCH₃ | $^1$H-NMR*): A: 5.87; 7.98; 8.34 B: 5.91; 8.05; 8.22 |

-continued

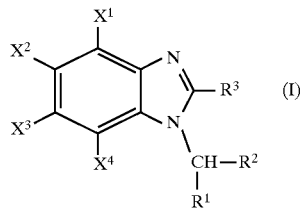

| Ex. No. | X¹ | X² | X³ | X⁴ | R¹ | R² | Physical Properties |
|---|---|---|---|---|---|---|---|
| 70 | H | | —O—CF$_2$—CF$_2$—O— | | H | H | —O—CH(CH$_3$)$_2$ | ¹H-NMR*): 5.61; 7.45; 7.65 |
| 71 | H | | —O—CF$_2$—CF$_2$—O— | | H | H | —CO—C$_6$H$_5$ | m.p. 141–143° C. |
| 72 | H | | —O—CF$_2$—CF$_2$—O— | | H | H | CN | m.p. 132–134° C. |
| 73 | H | | —O—CF$_2$—O— | | H | H | —O—CH(CH$_3$)$_2$ | m.p. 76–78° C. |
| 74 | H | | —O—CF$_2$—O— | | H | H | —CO—C$_6$H$_5$ | m.p. 188–189° C. |
| 75 | H | | —O—CF$_2$—O— | | H | H | CN | m.p. 145–147° C. |
| 76 | H | CF$_3$ (Br) | Br (CF$_3$) | H | H | —O—CH(CH$_3$)$_2$ | ¹H-NMR*): A: 5.65; 8.03; 8.23 B: 5.69; 8.05; 8.20 |
| 77 | H | CF$_3$ (Br) | Br (CF$_3$) | H | H | 2,4-dichlorophenyl | ¹H-NMR*): A: 5.56; 7.59; 8.29 B: 5.59; 7.61; 8.26 |
| 78 | H | CF$_3$ (H) | H (CF$_3$) | H | H | —O—C$_2$H$_5$ | ¹H-NMR*): A: 5.38; 7.18–7.94; B: 5.40 |
| 79 | H | CF$_3$ (H) | H (CF$_3$) | H | H | OH | ¹H-NMR*): 2.2; 7.76; 8.1 |
| 80 | H | CF$_3$ (Br) | Br (CF$_3$) | H | H | —O—C$_2$H$_5$ | ¹H-NMR*): A: 5.64; 8.03; 8.21 B: 5.72; 8.06; 8.18 |
| 81 | H | CF$_3$ | Br | H | H | —O—C$_2$H$_5$ | m.p. 66° C. |
| 82 | H | Br | CF$_3$ | H | H | —O—C$_2$H$_5$ | ¹H-NMR*): B: 5.72; 8.05; 8.17 |
| 83 | H | CF$_3$ (Br) | Br (CF$_3$) | H | H | —O-n-C$_3$H$_7$ | ¹H-NMR*): A: 6.67; 8.08; 8.27 B: 5.69; 8.11; 8.25 |
| 84 | H | CF$_3$ (Br) | Br (CF$_3$) | H | H | —O—CH$_2$—C≡CH | ¹H-NMR*): A: 5.51; 7.89; 8.17 B: 5.71; 7.93; 8.21 |
| 85 | H | CF$_3$ (Cl) | Cl (CF$_3$) | H | H | —O—C$_2$H$_5$ | ¹H-NMR*): A: 5.69; 7.82; 8.23 B: 5.71; 8.00; 8.03 |
| 86 | H | CF$_3$ | Cl | H | H | —O—C$_2$H$_5$ | m.p. 73° C. |
| 87 | H | Cl | CF$_3$ | H | H | —O—C$_2$H$_5$ | ¹H-NMR*): B: 5.71; 8.00; 8.03 |
| 88 | H | CF$_3$ (Cl) | Cl (CF$_3$) | H | H | —O—CH(CH$_2$F)$_2$ | ¹H-NMR*): A: 5.83; 7.78; 8.03 B: 5.89; 8.01; 8.26 |
| 89 | H | CF$_3$ (Cl) | Cl (CF$_3$) | H | H | —O-n-C$_3$H$_7$ | ¹H-NMR*): A: 5.70; 7.80; 8.06 B: 5.73; 7.99; 8.21 |

-continued

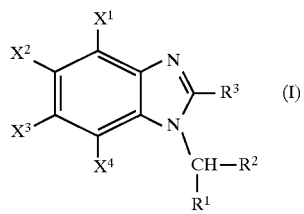

| Ex. No. | X¹ | X² | X³ | X⁴ | R¹ | R² | Physical Properties |
|---|---|---|---|---|---|---|---|
| 90 | H | CF$_3$ (Cl) | Cl (CF$_3$) | H | H | —O—CH$_2$—C≡CH | $^1$H-NMR*): A: 5.73; 7.81; 8.04 B: 5.77; 8.00; 8.02 |
| 91 | H | CF$_3$ (Cl) | Cl (CF$_3$) | H | H | —N(CH$_3$)—C(=O)—OC$_2$H$_5$ | $^1$H-NMR*): A: 5.90; 8.00; 8.21 B: 5.93; 8.03; 8.31 |
| 92 | H | CF$_3$ (Cl) | Cl (CF$_3$) | H | H | —N(C$_2$H$_5$)—C(=O)—OC$_2$H$_5$ | $^1$H-NMR*): A: 5.89; 8.00; 8.21 B: 5.95; 8.03; 8.33 |
| 93 | H | CF$_3$ (Cl) | Cl (CF$_3$) | H | H | —N(n-C$_3$H$_7$)—C(=O)—OC$_2$H$_5$ | $^1$H-NMR*): A: 5.89; 8.00; 8.22 B: 5.91; 8.04; 8.32 |
| 94 | H | CF$_3$ (Cl) | Cl (CF$_3$) | H | H | —CO—OC$_2$H$_5$ | m.p. 73° C. |
| 95 | H | CF$_3$ (Cl) | Cl (CF$_3$) | H | CH$_3$ | —CO—OC$_2$H$_5$ | $^1$H-NMR*): A: 1.91; 5.34; 7.57; 8.12 |
| 96 | H | | —O—CF$_2$—O— | H | H | —O—C$_2$H$_5$ | m.p. 92° C. |
| 97 | H | | —O—CF$_2$—O— | H | H | —O—CH(CH$_2$F$_2$) | m.p. 64° C. |
| 98 | H | | —O—CF$_2$—O— | H | H | —O-n-C$_3$H$_7$ | m.p. 41° C. |
| 99 | H | | —O—CF$_2$—O— | H | H | —O—CH$_2$—C≡CH | m.p. 87° C. |
| 100 | H | | —O—CF$_2$—O— | H | H | —N(CH$_3$)—C(=O)—OC$_2$H$_5$ | m.p. 93° C. |
| 101 | H | | —O—CF$_2$—O— | H | H | —N(C$_2$H$_5$)—C(=O)—OC$_2$H$_5$ | m.p. 67° C. |
| 102 | H | | —O—CF$_2$—O— | H | H | —N(n-C$_3$H$_7$)—C(=O)—OC$_2$H$_5$ | $^1$H-NMR*): 5.89; 7.51 |
| 103 | H | | —O—CF$_2$—CF$_2$—O— | H | H | —O—C$_2$H$_5$ | $^1$H-NMR*): 5.63; 7.52; 7.63 |

-continued

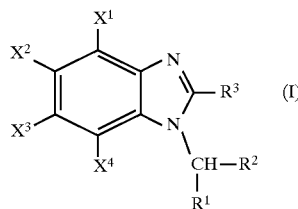

| Ex. No. | X¹ | X² | X³ | X⁴ | R¹ | R² | Physical Properties |
|---|---|---|---|---|---|---|---|
| 104 | H | | $-O-CF_2-CF_2-O-$ | H | H | $-O-CH(CH_2F)_2$ | $^1$H-NMR*): 5.82; 7.42; 7.68 |
| 105 | H | | $-O-CF_2-CF_2-O-$ | H | H | $-N(CH_3)-C(=O)-OC_2H_5$ | m.p. 118° C. |
| 106 | H | | $-O-CF_2-CF_2-O-$ | H | H | $-N(C_2H_5)-C(=O)-OC_2H_5$ | m.p. 85° C. |
| 107 | H | | $-O-CF_2-CF_2-O-$ | H | H | $-N(n\text{-}C_3H_7)-C(=O)-OC_2H_5$ | m.p. 103° C. |
| 108 | H | | $-O-CF_2-CF_2-O-$ | H | H | $-O\text{-}n\text{-}C_3H_7$ | $^1$H-NMR*): 5.75; 7.48; 7.54 |
| 109 | H | | $-O-CF_2-CF_2-O-$ | H | H | $-O-CH_2-C\equiv CH$ | $^1$H-NMR*): 5.81; 7.49; 7.68 |
| 110 | H | | $-O-CF_2-CF_2-O-$ | H | H | $-CO-OC_2H_5$ | m.p. 90° C. |
| 111 | H | | $-O-CF_2-CF_2-O-$ | H | $CH_3$ | $-CO-OC_2H_5$ | $^1$H-NMR*): 5.84; 5.34; 7.65 |
| 112 | H | | $-O-CF_2-CHF-O-$ ($-O-CHF-CF_2-O-$) | H | H | $-O-C_2H_5$ | $^1$H-NMR*): 5.84; 7.64; 7.71 |
| 113 | H | | $-O-CF_2-CHF-O-$ ($-O-CHF-CF_2-O-$) | H | H | $-O-CH(CH_2F)_2$ | $^1$H-NMR*): 5.81; 6.01; 7.35; 7.61 |
| 114 | H | | $-O-CF_2-CHF-O-$ ($-O-CHF-CF_2-O-$) | H | H | $-O\text{-}n\text{-}C_3H_7$ | $^1$H-NMR*): 5.70; 6.03; 7.50; 7.60 |
| 115 | H | | $-O-CF_2-CHF-O-$ ($-O-CHF-CF_2-O-$) | H | H | $-O-CH_2-C\equiv CH$ | $^1$H-NMR*): 5.56; 6.00; 7.46; 7.54 |
| 116 | H | | $-O-CF_2-CHF-O-$ ($-O-CHF-CF_2-O-$) | H | H | $-N(CH_3)-C(=O)-OC_2H_5$ | $^1$H-NMR*): 5.78; 6.01; 7.43; 7.57 |
| 117 | H | | $-O-CF_2-CHF-O-$ ($-O-CHF-CF_2-O-$) | H | H | $-N(C_2H_5)-C(=O)-OC_2H_5$ | $^1$H-NMR*): 5.80; 6.00; 7.45; 7.48 |
| 118 | H | | $-O-CF_2-CHF-O-$ ($-O-CHF-CF_2-O-$) | H | H | $-N(n\text{-}C_3H_7)-C(=O)-OC_2H_5$ | $^1$H-NMR*): 5.85; 6.05; 7.53; 7.68 |

-continued

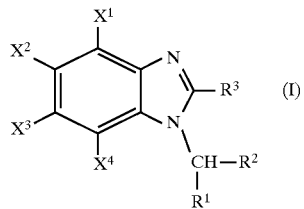

| Ex. No. | X¹ | X² | X³ | X⁴ | R¹ | R² | Physical Properties |
|---|---|---|---|---|---|---|---|
| 119 | H | —O—CF$_2$—CHF—O— (—O—CHF—CF$_2$—O—) | | H | H | —CO—OC$_2$H$_5$ | $^1$H-NMR*): 4.98; 6.03; 7.09; 7.63 |
| 120 | H | —O—CF$_2$—CHF—O— (—O—CHF—CF$_2$—O—) | | H | CH$_3$ | —CO—OC$_2$H$_5$ | $^1$H-NMR*): 1.86; 6.01; 7.19; 7.62 |
| 121 | H | —O—CF$_2$—CClF—O— (—O—CClF—CF$_2$—O—) | | H | H | —O—C$_2$H$_5$ | $^1$H-NMR*): 2.35; 7.15–7.98 |
| 122 | H | —O—CF$_2$—CClF—O— (—O—CClF—CF$_2$—O—) | | H | H | —O-n-C$_3$H$_7$ | |
| 123 | H | —O—CF$_2$—CClF—O— (—O—CClF—CF$_2$—O—) | | H | H | —O—CH$_2$—C≡CH | |
| 124 | H | —O—C(CF$_3$)(CH$_2$—CF$_3$)—O— | | H | H | —O—C$_2$H$_5$ | $^1$H-NMR*): 5.62; 7.28; 7.32 |
| 125 | H | —O—C(CF$_3$)(CH$_2$—CF$_3$)—O— | | H | H | —N(CH$_3$)—C(O)—OC$_2$H$_5$ | $^1$H-NMR*): A: 5.78; 7.32; 7.44 B: 5.80; 7.32; 7.44 |
| 126 | H | —O—C(CF$_3$)(CH$_2$—CF$_3$)—O— | | H | H | —N(C$_2$H$_5$)—C(O)—OC$_2$H$_5$ | $^1$H-NMR*): A: 5.76; 7.30; 7.42 B: 5.78; 7.30; 7.42 |
| 127 | H | —O—C(CF$_3$)(CH$_2$—CF$_3$)—O— | | H | H | —N(n-C$_3$H$_7$)—C(O)—OC$_2$H$_5$ | $^1$H-NMR*): A: 5.76; 7.32; 7.42 B: 5.78; 7.32; 7.42 |
| 128 | H | CF$_3$O (H) | H (CF$_3$O) | H | H | —O—C$_2$H$_5$ | |
| 129 | H | CF$_3$O | CF$_3$O | H | H | —O—C$_2$H$_5$ | $^1$H-NMR*): 5.50; 7.78; 7.82 |
| 130 | H | CF$_3$O | CF$_3$O | H | H | —O-n-C$_3$H$_7$ | $^1$H-NMR*): 5.51; 7.75; 7.79 |
| 131 | H | CF$_3$O | CF$_3$O | H | H | —O—CH$_2$—C≡CH | $^1$H-NMR*): 5.48; 7.76; 7.80 |
| 132 | H | CF$_3$O | CF$_3$O | H | H | —O—CH(CH$_2$F)$_2$ | $^1$H-NMR*): 5.80; 7.78; 7.84 |
| 133 | H | CH$_3$—SO$_2$— (CF$_3$)(H) | H (CH$_3$—SO$_2$—) | CF$_3$ (H) | H | —O—C$_2$H$_5$ | $^1$H-NMR*): 5.80; 8.25; 8.56 |
| 134 | H | CF$_3$ (CH$_3$O) | (CH$_3$O) CF$_3$ | H | H | —O—C$_2$H$_5$ | $^1$H-NMR*): A: 5.49; 7.05; 7.70 B: 5.50; 7.10; 7.73 |
| 135 | H | (C$_2$H$_5$)$_2$N—CO— (H) | H ((C$_2$H$_5$)$_2$N—CO—) | H | H | —O—C$_2$H$_5$ | $^1$H-NMR*): 5.73; 5.74; 7.29–8.63 |
| 136 | H | C$_2$H$_5$O—CO— (H) | H (C$_2$H$_5$O—CO—) | H | H | —O—C$_2$H$_5$ | $^1$H-NMR*): 5.72; 5.74; 7.65–8.59 |
| 137 | H | C$_6$H$_5$—CO—NH— (H) | H (C$_6$H$_5$—CO—NH—) | H | H | —O—C$_2$H$_5$ | $^1$H-NMR*): 5.70; 7.21–8.48; |

-continued

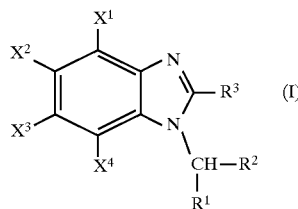

| Ex. No. | X¹ | X² | X³ | X⁴ | R¹ | R² | Physical Properties |
|---|---|---|---|---|---|---|---|
| 138 | H | CH₃O—CO— (H) | H (CH₃O—CO—) | H | H | —O—C₂H₅ | 7.98 ¹H-NMR*): 5.72; 5.74; 7.68–8.59 |

The following substituted benzimidazoles of the general formula (Ia) are additionally obtained in a corresponding manner:

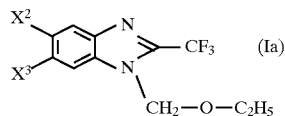

| Ex. No. | X² | X³ | Physical Properties |
|---|---|---|---|
| 139 | Cl—C₆H₄—CH₂—SO₂—N(CH₂—OC₂H₅)— (H) | H (Cl—C₆H₄—CH₂—SO₂—N(CH₂—OC₂H₅)—) | ¹H-NMR*): 5.69; 5.70; 7.03–8.05 |
| 140 | C₆H₅—CH₂—SO₂—NH— (H) | H (C₆H₅—CH₂—SO₂—NH—) | ¹H-NMR*): 5.65; 5.67; 6.71–8.03 |
| 141 | C₆H₅—SO₂—NH— (H) | H (C₆H₅—SO₂—NH—) | |
| 142 | 2-Cl-C₆H₄—SO₂—NH— (H) | H (2-Cl-C₆H₄—SO₂—NH—) | ¹H-NMR*): 5.32; 5.63; 7.15–8.46 |
| 143 | 2-CF₃-C₆H₄—SO₂—NH— (H) | H (2-CF₃-C₆H₄—SO₂—NH—) | ¹H-NMR*): 5.18; 5.63; 6.95–8.40 |
| 144 | (CH₃)₃C—CH₂—O—C(O)— (H) | H ((CH₃)₃C—CH₂—O—C(O)—) | ¹H-NMR*): 5.81; 5.82; 7.65–8.62 |
| 145 | 2,4-Cl₂-C₆H₃—NH—C(O)—NH— (H) | H (2,4-Cl₂-C₆H₃—NH—C(O)—NH—) | ¹H-NMR*): 5.58; 5.62; 6.78–8.15 |

-continued

| Ex. No. | X² | X³ | Physical Properties |
|---|---|---|---|
| 146 | F₃C—CH₂—C(CF₃)—O—[phenyl]—NH—C(O)—NH— (H) | (F₃C—CH₂—C(CF₃)—O—[phenyl]—NH—C(O)—NH—) H | ¹H-NMR*): 5.53; 6.45–8.07 |
| 147 | C₂H₅O—(CH₂)₂—O—[Cl-phenyl]—NH—C(O)—NH— (H) | (C₂H₅O—(CH₂)₂—O—[Cl-phenyl]—NH—C(O)—NH—) H | ¹H-NMR*): 5.51; 5.54; 6.71–8.01 |
| 148 | n-C₃H₇O—(CH₂)₂—[Cl-phenyl]—NH—C(O)—NH— (H) | (n-C₃H₇O—(CH₂)₂—[Cl-phenyl]—NH—C(O)—NH—) H | |
| 149 | C₂H₅O—(CH₂)₂—O—[phenyl]—NH—C(O)—NH— (H) | (C₂H₅O—(CH₂)₂—O—[phenyl]—NH—C(O)—NH—) H | ¹H-NMR*): 5.54; 5.58; 6.72–8.08 |
| 150 | i-C₃H₇O—(CH₂)₂—O—[phenyl]—NH—C(O)—NH— (H) | (i-C₃H₇O—(CH₂)₂—O—[phenyl]—NH—C(O)—NH—) H | ¹H-NMR*): 5.49; 5.53; 6.61–8.11 |

*)The ¹H-NMR specta were recorded in deuterochloroform (CDCl₃) or hexadeutero-dimethyl sulphoxide (DMSO-d₆) with tetramethylsilane (TMS) as the internal standard. The data given are the chemical shift as δ value in ppm.

Preparation of the Starting Compound

Example II-1

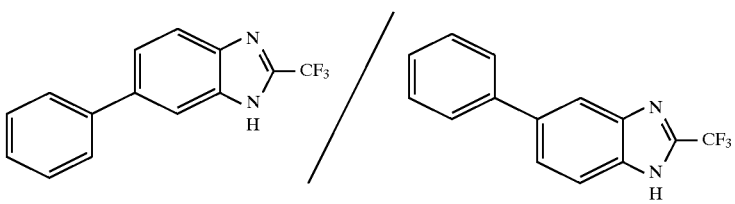

18.4 g (0.092 mol) of 3,4-diaminobiphenyl and 150 ml of trifluoroacetic acid are refluxed for 5 hours. Excess trifluoroacetic acid is subsequently distilled off, the residue is partitioned between 200 ml of ethyl acetate and 70 ml of water, the organic phase is separated off, washed with in each case 70 ml of saturated aqueous sodium hydrogen carbonate solution and water, dried over sodium sulphate and concentrated in vacuo, and the residue is purified by chromatography over silica gel (eluent: cyclohexane/ethyl acetate 2:1).

18.3 g(76% of theory) of 5(6-phenyl-2-trifluoromethyl-1H-benzimidazole as a 1:1 regioisomer mixture of melting point 177°–182° C. are obtained.

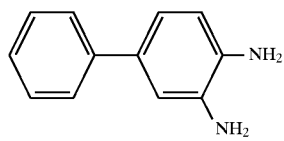

88 g (0.4 mol) of 4-amino3-nitro-biphenyl (92 percent) are hydrogenated with molecular hydrogen in 3000 ml of methanol in the presence of 10 g of Raney nickel at 60° C. and a pressure of 5 bar. For working up, the Raney nickel is filtered off and the filtrate is concentrated in vacuo.

69.2 g (86% of theory) of 3,4-diaminobiphenyl of melting point 96°–99° C. are obtained (purity according to HPLC 92%).

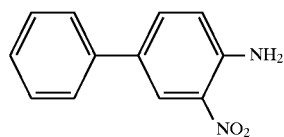

43 g (0.15 mol) of 4-acetamido-3-nitro-biphenyl (90 percent) and 1.6 g (0.03 mol) of sodium methylate are refluxed for 2 hours in 500 ml of methanol. For working up, the cooled reaction mixture is poured into 1300 ml of ice-water and stirred for 10 minutes, and the precipitate which has separated out is then filtered off with suction and dried.

33 g (94% of theory) of 4-amino-3-nitro-biphenyl of melting point 163°–165° C. are obtained (purity according to HPLC 92%).

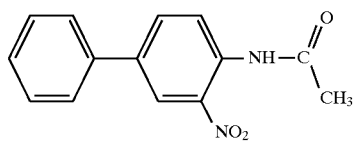

A mixture of 50.4 ml (1.2 mol) of 98 percent strength nitric acid and 60 ml of glacial acetic acid is added dropwise with stirring at 70° C. to a suspension of 84.4 g (0.4 mol) of 4-acetamido-biphenyl (compare, for example, Beilstein Volume 12, 4th Supplement, p. 3248) in 340 ml of glacial acetic acid, and, when the addition has ended, the mixture is stirred for a further hour at 70° C. For working up, the cooled reaction mixture is poured into 1.00 ml of ice-water and stirred for 10 minutes, and the precipitate which has separated out is filtered off with suction, washed with 200 ml of water and dried.

100 g (88% of theory) of 4-acetamido-3-nitrobiphenyl of melting point 128°–131° C. are obtained (purity according to HPLC 90%).

The following 1H-benzimidazoles of the formula

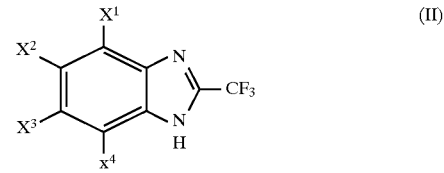

(II)

are obtained in a corresponding manner.

| Ex. No. | $X^1$ | $X^2$ | $X^3$ | $X^4$ | Physical Properties |
|---|---|---|---|---|---|
| II-2 | Br (H) | H ($CF_3$) | $CF_3$ (H) | H (Br) | m.p. 149–151° C. |
| II-3 | H | H ($C_6H_5-CO-$) | $C_6H_5-CO-$ (H) | H | m.p. 120–122° C. |
| II-4 | H | $CH_3-CO-$ (H) | H ($CH_3-CO-$) | H | m.p. 145–149° C. |
| II-5 | H | $Cl-CH_2-SO_2-$ (H) | H ($Cl-CH_2-SO_2-$) | H | m.p. 197–200° C. |
| II-6 | H | | $-O-CH_2-CH_2-CH_2-O-$ | H | m.p. >230° C. |
| II-7 | H | $H_3C-SO_2-$ (H) | H ($H_3C-SO_2-$) | H | |
| II-8 | Br (H) | H ($Cl-CH_2-SO_2-$) | $Cl-CH_2-SO_2-$ (H) | H (Br) | m.p. 180–187° C. |
| II-9 | H | $CF_3$ (Br) | Br ($CF_3$) | H | m.p. 209° C. |
| II-10 | H | | $-O-CF_2-O-$ | H | m.p. 242° C. |
| II-11 | H | | $-O-CF_2-CF_2-O-$ | H | m.p. 235–237° C. |
| II-12 | H | | $-O-CF_2-CHF-O-$ ($-O-CHF-CF_2-O-$) | H | m.p. 217° C. |
| II-13 | H | | $-O-CFCl-CFCl-O-$ | H | m.p. 185° C. |
| II-14 | H | $CF_3O$ (Cl) | Cl ($CF_3O$) | H | m.p. 144° C. |
| II-15 | H | | $-O-C(CF_3)(CH_2-CF_3)-O-$ | H | m.p. 209° C. |
| II-16 | H | $CF_3O$ (H) | H ($CF_3O$) | H | m.p. 168° C. |
| II-17 | H | $CF_3O$ | $CF_3O$ | H | m.p. 158° C. |
| II-18 | H ($CF_3$) | $CH_3-SO_2-$ (H) | H ($CH_3-SO_2-$) | $CF_3$ (H) | m.p. 105° C. |
| II-19 | H | $CF_3$ ($CH_3O$) | $CH_3O$ ($CF_3$) | H | m.p. 60° C. |
| II-20 | H | $(C_2H_5)N-CO-$ (H) | H ($(C_2H_5)N-CO-$) | H | m.p. 125° C. |
| II-21 | H | $C_2H_5O-CO-$ (H) | H ($C_2H_5O-CO-$) | H | m.p. 140° C. |

-continued
| Ex. No. | X¹ | X² | X³ | X⁴ | Physical Properties |
|---|---|---|---|---|---|
| II-22 | H | C₆H₅—CO—NH— (H) | H (C₆H₅—CO—NH—) | H | m.p. 202° C. |
| II-23 | H | CH₃O—CO— (H) | H (CH₃O—CO—) | H | m.p. 157° C. |
| II-24 | H | (CH₃)₂N—CO— (H) | H ((CH₃)₂N—CO—) | H | m.p. 226–227° C. |
| II-25 | H | F₂CH—CF₂—O— (H) | H (F₂CH—CF₂—O—) | H | m.p. 181° C. |
| II-26 | H | C₆H₅—SO₂—NH— (H) | H (C₆H₅—SO₂—NH—) | H | m.p. 70° C. |
| II-27 | H | 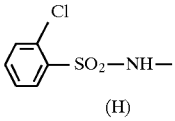 | 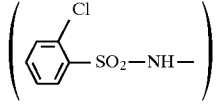 | H | m.p. 67° C. |
| II-28 | H | 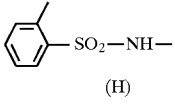 | 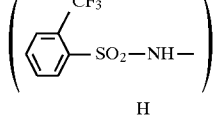 | H | m.p. 79° C. |
| II-29 | H | 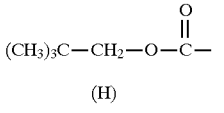 | 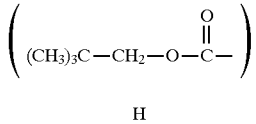 | H | m.p. 214–215° C. |
| II-30 | H | 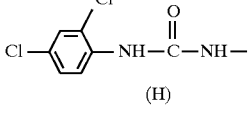 | 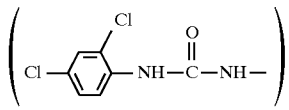 | H | m.p. 254–255° C. |
| II-31 | H | 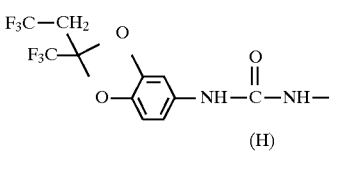 | 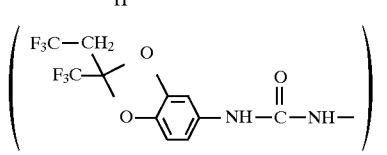 | H | m.p. 103° C. |
| II-32 | H | 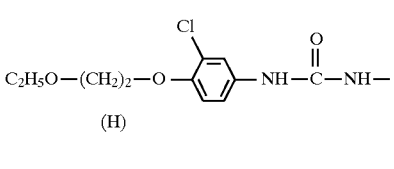 | 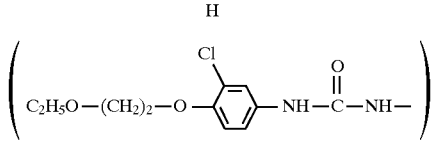 | H | m.p. 186° C. |
| II-33 | H | 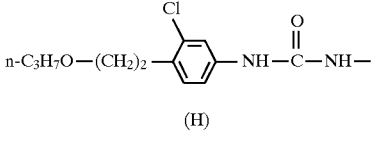 | 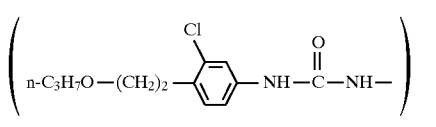 | H | m.p. 144° C. |
| II-34 | H | 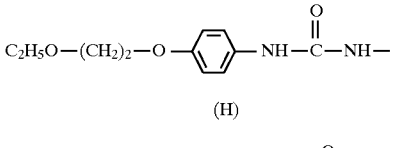 | 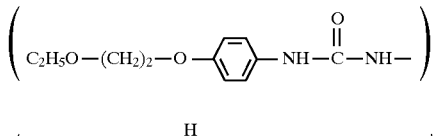 | H | m.p. 207° C. |
| II-35 | H | 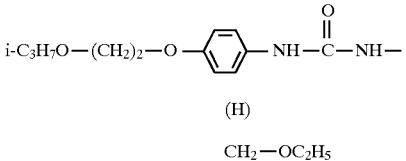 | 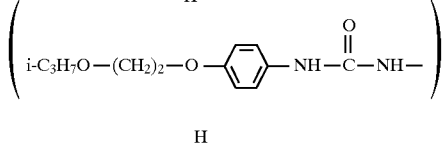 | H | m.p. 201° C. |
| II-36 | H | 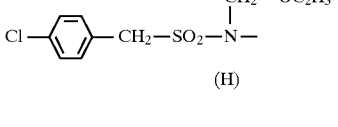 | 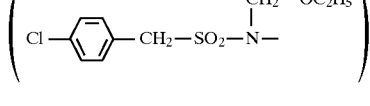 | H | m.p. 80° C. |

-continued

| Ex. No. | X¹ | X² | X³ | X⁴ | Physical Properties |
|---|---|---|---|---|---|
| II-37 | H | (CF₃)₂N— (H) | H ((CF₃)₂N—) | H | |
| II-38 | H | PhCH₂—SO₂—NH— (H) | H (PhCH₂—SO₂—NH—) | H | m.p. 68° C. |
| II-39 | H | CF₃S (H) | H (CF₃S) | H | m.p. 174° C. |
| II-40 | H | FClCH—CF₂—O— (H) | H (FClCH—CF₂—O—) | H | m.p. 57° C. |
| II-41 | H | 2,4-Cl₂-C₆H₃—NH—C(O)—NH— (H) | H (2,4-Cl₂-C₆H₃—NH—C(O)—NH—) | H | m.p. 176° C. |
| II-42 | H | CH₃—SO₂—NH—C₆H₄—SO₂—NH— (H) | H (CH₃—SO₂—NH—C₆H₄—SO₂—NH—) | H | |
| II-43 | H | Ph—NH—C(O)—NH— (H) | H (Ph—NH—C(O)—NH—) | H | m.p. 190° C. |
| II-44 | H | CH₃O—(CH₂)₂—O—C₆H₄—NH—C(O)—NH— (H) | H (CH₃O—(CH₂)₂—O—C₆H₄—NH—C(O)—NH—) | H | m.p. 208° C. |
| II-45 | H | (CH₃)₃C—O—CO— (H) | H ((CH₃)₃C—O—CO—) | H | m.p. 162° C. |
| II-46 | H | 2-(COOCH₃)-C₆H₄—SO₂—NH— (H) | H (2-(COOCH₃)-C₆H₄—SO₂—NH—) | H | m.p. 70° C. |
| II-47 | H | 2-Cl-C₆H₄—NH—C(O)—NH— (H) | H (2-Cl-C₆H₄—NH—C(O)—NH—) | H | |
| II-48 | H | 4-O₂N-C₆H₄—C(O)—NH— (H) | H (4-O₂N-C₆H₄—C(O)—NH—) | H | m.p. 61° C. |
| II-49 | H | 2-Cl-C₆H₄—C(O)—NH— (H) | H (2-Cl-C₆H₄—C(O)—NH—) | H | m.p. 76° C. |
| II-50 | H | CH₃O—CO—N(CH₃)—SO₂—NH— (H) | H (CH₃O—CO—N(CH₃)—SO₂—NH—) | H | |

-continued

| Ex. No. | $X^1$ | $X^2$ | $X^3$ | $X^4$ | Physical Properties |
|---|---|---|---|---|---|
| II-51 | H | COOH (H) | H (COOH) | H | m.p. 250° C. |
| II-52 | H | $(CH_3)_3C-NH-CO-$ (H) | H $((CH_3)_3C-NH-CO-)$ | H | m.p. 79° C. |
| II-53 | H | $F_3C-\underset{\underset{CH_3}{\mid}}{\overset{\overset{CH_3}{\mid}}{C}}-NH-\overset{O}{\overset{\parallel}{C}}-$ (H) | H $\left(F_3C-\underset{\underset{CH_3}{\mid}}{\overset{\overset{CH_3}{\mid}}{C}}-NH-\overset{O}{\overset{\parallel}{C}}-\right)$ | H | m.p. 39° C. |
| II-54 | H | $NC-CH_2-$ (H) | H $(NC-CH_2-)$ | H | |
| II-55 | H | $NH_2$ (H) | H $(NH_2)$ | H | |
| II-56 | H | $HOOC-CH_2-$ (H) | H $(HOOC-CH_2-)$ | H | |
| II-57 | H | $F_3C-SO_2-$ (H) | H $(F_3C-SO_2-)$ | H | |

*)The $^1$H-NMR spectra were recorded in deuterochloroform (CDCl$_3$) or hexadeuterodimethyl sulphoxide (DMSO-d$_6$) with tetramethylsilane (TMS) as the internal standard. The data given are the chemical shift as δ value in ppm.

Chloro-(2-halogen-1-fluoromethyl-ethoxy)-methanes of the formula

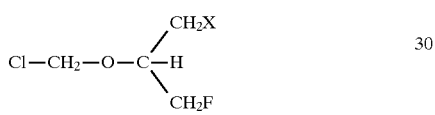

in which
X represents fluorine or chlorine
[Specifically, these are chloro-(2-fluoro-1-fluoromethyl-ethoxy)-methane (formula (I), X=fluorine) and chloro-(2-chloro-1-fluoromethyl-ethoxy-methane (formula (I), X=chlorine).]
can be obtained by reacting halogenated isopropanols of the formula

in which
X represents fluorine or chlorine,
with formaldehyde and hydrogen chloride at −20° to +20° C.

They can be used for the preparation of substituted benzimidazoles of the formula

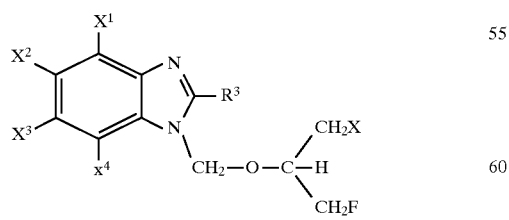

in which
X represent fluorine or chlorine and
$X^1$, $X^2$, $X^3$ and $X^4$ independently of one another in each case represent hydrogen, halogen, cyano, nitro, in each case optionally substituted alkyl, alkoxy, alkylthio, alkylsulphinyl, alkylsulphonyl or cycloalkyl, optionally substituted, fused dioxyalkylene, or hydroxycarbonyl, alkylcarbonyl, alkoxycarbonyl, cycloalkyloxycarbonyl, in each case optionally substituted amino or aminocarbonyl or in each case optionally substituted aryl, aryloxy, arylthio, arylsulfinyl, arylsulphonyl, arylsulphonyloxy, arylcarbonyl, aryloxycarbonyl, arylazo or arylthiomethylsulphonyl, but where at least one of the substituents $X^1$, $X^2$, $X^3$ or $X^4$ represents halogenoalkyl with the exception of the chloromethyl radical, halogenoalkoxy, halogenoalkylthio, halogenoalkylsulphinyl, halogenoalkylsulphonyl, alkylsulphonyl, optionally substituted, fused dioxyalkylene, or hydroxycarbonyl, alkylcarbonyl, alkoxycarbonyl, cycloalkyloxycarbonyl, in each case optionally substituted amino or aminocarbonyl, or in each case optionally substituted aryl, arylthio, arylsulphinyl, arylsulphonyl, arylsulphonyloxy, arylcarbonyl, aryloxycarbonyl, arylazo or arylthiomethylsulphonyl, from benzimidazoles of the formula

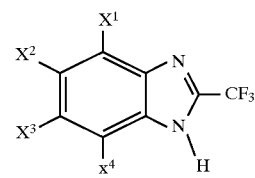

EXAMPLE 192 g of 1,3difluoro-2-propanol were treated with 66 g of paraformaidehyde (finely powdered). At −10° C., a vigorous stream of hydrogen chloride gas was then passed in, with stirring, until a clear 2-phase mixture had formed. The organic phase was subsequently separated off, dried using calcium chloride and subjected to fracional distillation in vacuo. With a boiling point of 50° to 54° C. at 20 mbar, 183 g (60% of theory) of chloro-2-fluoro-1-fluoromethyl-ethoxy)-methane were obtained. The characteristic absorptions in the NMR spectra were as follows:

$^1$H-NMR: 5.6 ppm and 4.55 ppm.

$^{19}$F-NMR: –233 ppm.

Fluorinated 1,3-benzo-dioxoles of the formula

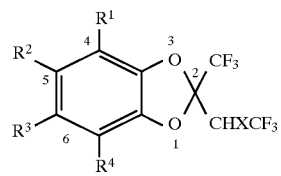

in which

X represents hydrogen, fluorine, chlorine or bromine and $R^1$ and $R^4$ can be identical or different from each other and in each case denote hydrogen, halogen $C_1$–$C_6$-alkyl, $C_1$–$C_6$-alkoxy, halogen-$C_1$–$C_6$-alkyl, $C_6$–$C_{10}$-aryl, COOH, CN, NCO, COO-$C_1$–$C_6$-alkyl, NH-$C_1$–$C_6$-alkyl or N($C_1$–$C_6$-alkyl)$_2$, and $R^2$ and $R^3$ represent $NO_2$ or $NH_2$, can be obtained by reacting 1,2-dihydroxybenzenes

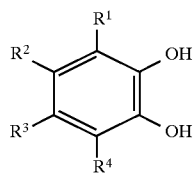

in which $R^1$ to $R^4$ have the abovementioned meaning, with hexafluorobutene of the formula

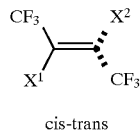

cis-trans in which $X^1$ represents hydrogen or halogen and $X^2$ represents halogen, in the presence of a base and of a diluent at –20° to +200° C., or by first reacting 1,2-dihydroxybenzenes which have a protective group, of the formula

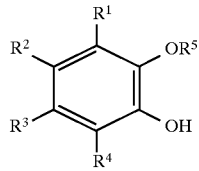

in which $R^1$ to $R^4$ have the abovementioned meaning and $R^5$ represents a protective group or $R^5$ together with $R^1$ represents a —C(CH$_3$)$_2$—O— radical with a hexafluorobutene of the formula

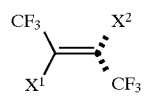

cis-trans in which $X^1$ represents hydrogen or halogen and $X^2$ represents halogen, thus resulting in an intermediate of the formula

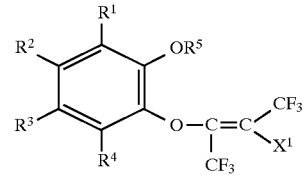

in which $R^1$ to $R^4$, $R^5$ and $X^1$ have the abovementioned meaning, eliminating the protective group $R^5$ from the intermediate of the above formula, and reacting the resulting OH compound with a base, thus obtaining 1,3-benzo-dioxoles of the above formula. 1,3-Benzo-dioxoles which have two adjacent amino groups can be converted with trifluoroacetic acid to give the corresponding benzimidazole, for example of the following formula

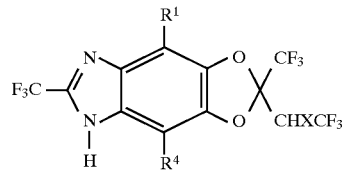

in which $R^1$, $R^4$ and X have the abovementioned meaning.

By alkylation, benzimidazole derivatives can be obtained from these which are substituted on the nitrogen atom by a

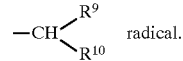

radical.

EXAMPLES

Example 1a 2-2,2,2-Trifluoroethyl)-2-trifluoromethyl-1,3benzodioxole 11 g of pyrocatechol were dissolved in 200 ml of dimethylformamide and the solution was treated with 18 g of 45% strength by weight aqueous sodium hydroxide solution. The mixture was treated dropwise at 75° C. with 20 g of 2-chloro-1,1,1,4,4,4-hexafluoro-2-butene. Stirring was continued for 30 minutes at 75° C. The batch was subsequently poured into 500 ml of ice-water and extracted using diethyl ether. The organic phase was washed with water, dried with magnesium sulphate and concentrated. Finally, the product was distilled under a high vacuum. The yield was 15 g (=56%), and the boiling point 60° C. at 10 mbar. The NMR spectra showed the following characteristic absorptions: $^{19}$F-NMR: –59.0 and –84.6 ppm $^1$H-NMR: 3.02 ppm.

Example 2a 2-(1-Chloro-2,2,2-trifluoroethyl)-2-trifluoromethyl-1,3-benzodioxole 110 g of pyrocatechol were dissolved in 1500 ml of acetonitrile, and the solution was treated with 200 g of triethylamine. The mixture was treated dropwise at 75° C. with 235 g of 2,3-dichloro-1,1,1,4,4,4-hexafluoro-2-butene. Stirring was continued for 2 hours at 75° C. 1200 ml of the solvent were subsequently distilled off in vacuo, and the residue was taken up in 1500 ml of water. The product was extracted using diethyl ether, and the organic phase was washed twice using 10% strength by weight aqueous sodium hydroxide solution and once with water. After drying with magnesium sulphate, the organic phase was concentrated and subjected to fractional distillation in vacuo. The yield was 258 g (=84% of theory). The boiling point was 63° C. at 12 mbar. The NMR spectra showed the following characteristic absorptions: $^{19}$F-NMR: −66.8 and −79.7 ppm $^1$H-NMR: 4.71 ppm.

Examples 3a 2-1,1,1,4,4,4-Hexafluoro-2-butenoxy)-methoxybenzene 260 g of 2-methoxyphenol were dissolved in 1 l of dimethylformamide (technical grade) and the solution was treated with 220 g of 45% strength sodium hydroxide solution. 400 g of 2-chloro-1,1,1,4,4,4-hexafluoro-2-butene were then added dropwise with stirring at 22° C. Stirring was continued for 2 hours up to 22° C. The mixture was then treated with 1.5 l of icewater and extracted with methylene chloride.

The combined organic phases were washed twice using 10% strength sodium hydroxide solution and once using saturated NaCl solution, dried using MgSO$_4$ and distilled. The yield was 329 g (58% of theory), and the boiling point was 68°–70° C. at 12 mbar. The NMR spectra showed the following characteristic absorptions: $^{19}$F-NMR: −57.6 and −67.9 ppm. $^1$H-NMR: 5.92 ppm.

Example 4a 2-(1,1,1,4,4,4-Hexafluoro-2-butenoxy)-phenol 286.1 g of 2-(1,1,1,4,4,4-hexafluoro-2-butenoxy)-methoxybenzene of Example 3a were dissolved in a mixture of 500 ml of glacial acetic acid and 500 ml of 48% strength hydrobromic acid, and the mixture was treated with 5 g of triethylbenzylammonium chloride. The mixture was stirred at a bath temperature of 150° C. until a gas-chromatographic check showed that the reaction was complete. The mixture was then allowed to cool and treated with 2 kg of ice-water. The aqueous phase was extracted thoroughly using CH$_2$Cl$_2$. After drying with MgSO$_4$, the solvent was stripped off and the residue distilled in vacuo. The yield was 200 g (50% of theory), and the boiling point was 80° C. at 16 mbar. The NMR spectra showed the following characteristic absorptions: $^{19}$F-NMR: −59.6 and −69.6 ppm. $^1$H-NMR: 6.1 ppm.

Example 5a 2-(2,2,2-Trifluoroethyl)-2-trifluoromethyl-1,3-benzodioxole 200 g of 2-(1,1,1,4,4,4,-Hexafluoro-2-butenoxy)-phenol of Example 4a were dissolved in 400 ml of acetonitrile and the solution was treated with 5 g of triethylamine. The mixture was stirred for 4 h at 70° C. It was then distilled in vacuo. The yield was 162 g (81% of theory), and the boiling point was 60° C. at 10 mbar. The NMR spectra showed the following characteristic absorptions: $^{19}$F-NMR: −59.0 and −84.6 ppm. $^1$H-NMR: 3.02 ppm.

Example 6a 2-(2-Chloro-1,1,1,4,4,4-hexafluoro-2-butenoxy)-1-benzyloxybenzene 20 g of 2-benzyloxyphenol were dissolved in 100 ml of dimethylformamide and the solution was treated with 9 g of 45% strength sodium hydroxide solution. 23 g of 2,3-dichloro-1,1,1,4,4,4-hexafluoro-2-butene were then added dropwise at room temperature. After the exothermic reaction had subsided, stirring was continued for 1 hour at room temperature. and the mixture was poured into water and extracted using tert.-butyl methyl ether. After drying with MgSO$_4$, the solvent was stripped off. The yield was 29 g (74% of theory). The NMR spectra showed the following characteristic absorptions: $^{19}$F-NMR: −59.5; −60.5; −61.7 and −62.8 ppm.

Example 7a 2-(2-Chloro-1,1,1,4,4,4-hexafluoro-2-butenoxy)-phenol 24.4 g of 2-(2-chloro-1,1,1,4,4,4-hexafluoro-2-butenoxy) -1-benzyloxybenzene of Example 6a were dissolved in 150 ml of tetrahydrofuran and the solution was treated with 3 bar hydrogen for 4 hours at room temperature in the presence of 2 g of Pd/C (10% strength). The mixture was subsequently filtered and the filtrate was concentrated and distilled in vacuo. The yield was 13.2 g (69% of theory), and the boiling point was 56° C. at 0.15 mbar.

Example 8a 2-(1-Chloro-2,2,2-trifluoroethyl)-2-trifluoromethyl-1,3-benzodioxole 11.7 g of 2-(2-chloro-1,1,1,4,4,4-hexafluoro-2-butenoxy) phenol of Example 7a were dissolved in 40 ml of tert.-butyl methyl ether and the solution was treated with 40 ml of 1N sodium hydroxide solution. After the mixture had been stirred for 30 minutes at room temperature, the organic phase was separated off, dried using MgSO$_4$ and distilled. The yield was 10 g (88% of theory), and the boiling point was 63° C. at 12 mbar. The NMR spectra showed the following characteristic absorptions: $^{19}$F-NMR: −66.8 and −79.7 ppm. $^1$H-NMR: 4.71 ppm.

Example 9a 2,2-Dimethyl-4-(1,1,1,4,4,4-hexafluoro-2-butenoxy)-1,3-benzodioxole(Formula V, R$^5$ together with R$^1$=—C(CH$_3$)$_2$ —O— radical)

46 g of 2,2-dimethyl-4-hydroxy-1,3-benzodioxole (Formula IV, R$^5$ together with R$^3$=—C(CH$_3$)$_2$—O— radical) were dissolved in 200 ml of N-methylpyrrolidone and the solution was treated with 31 g of 40% strength by weight aqueous sodium hydroxide solution. 54.8 g of 2-chloro-1,1,1,4,4,4-hexafluoro-2-butene were subsequently added dropwise at room temperature with stirring. Stirring was continued for 1 hour, and the batch was then poured into water and extracted using tert.-butyl methyl ether. The organic phase was washed using 10% strength by weight aqueous sodium hydroxide solution and dried using magnesium sulphate, and the readily volatile components were removed on a rotary evaporator. This gave 73.8 g (=80% of theory) of a product whose purity was 95% according to gas chromatography. The characteristic absorptions in the NMR spectra were: $^{19}$F-NMR: −58.1 and −68.5 ppm. $^1$H-NMR: 6.73, 6.55, 6.03 and 1.70 ppm.

Example 10a 1,2-Dihydroxy-3-(1,1,1,4,4,4hexafluoro-2-butenoxy)-benzene 65 g of the product of Example 9a and 200 ml of concentrated aqueous hydrochloric acid were refluxed for 4 hours with stirring the batch was subsequently diluted with 300 ml of water and extracted using methylene chloride. After drying with magnesium sulphate, the solvent was stripped off from the organic phase, giving 54 g of a product of 90% purity. Recrystallization from cyclohexane gave colourless crystals having a melting point of 105° C. The characteristic absorptions in the NMR spectra were as follows: $^{19}$F-NMR −57.7 and −67.7 ppm. $^{1}$H-NMR: 6.77, 6.50, 6.21 and 5.42 ppm.

Example 11a
2-(2,2,2-Trifluoroethyl)-2-(trifluoromethyl)-4-hydroxy-1,3-benzodioxole (Formula (I) $R^1$=OH, X=H, A=CH, $R^2$ and $R^3$=H)

43.5 g of the product of Example 10a were dissolved in 300 ml of acetonitrile, and 1.5 g of triethylamine were added at room temperature. After the mixture had been stirred for 2 hours at room temperature, the solvent was stripped off and the residue was distilled in vacuo. The yield was 17 g (=39% of theory), the boiling point was 85° C. at 0.15 mbar, and the melting point was 65° C. The characteristic absorptions in the NMR spectra were as follows: $^{19}$F-NNMR: −59.0 and −84.5 ppm. $^{1}$H-NMR: 6.80, 6.55, 6.2 and 3.01 ppm.

Example 12a
2,2-Dimethyl-4-(3-chloro-1,1,1,4,4,4-hexafluoro-2-butenoxy)-1,3-benzodioxole (Formula (V), $R^1$ and $R^5$ together are —C(CH$_3$)—O—, $X^1$=Cl, $R^2$+$R^3$=H, A=CH)

33.2 g of 2,2-dimethyl-4-hydroxy-1,3-benzodioxole were reacted analogously to Example 9a with 47 g of 2,3-dichloro-1,1,1,4,4,4-hexafluoro-2-butene. The product obtained was distilled in vacuo, and a 1:1 molar mixture of cis/transisomers was obtained. The yield was 51 g (=70% of theory), and the boiling point was 70° C. at 0.15 mbar. The characteristic absorptions in the NMR spectra were as follows: $^{19}$F-NMR: −60.0, −61.6, −62.2 and 63.4 ppm. $^{1}$H-NMR: 6.79, 6.65 to 6.48 and 1.7 ppm.

Example 13a
1,2-Dihydroxy-3-(3-chloro-1,1,1,4,4,4hexafluoro-2-butenoxy)benzene (Formula (V), $R^1$=OH, $R^2$+$R^3$=H, A=CH, $R^5$=H, $X^1$=Cl)

18 g of the product of Example 12a were reacted analogously to Example 10a with 50 ml of concentrated hydrochloric acid. 15.7 g of a product with a purity of 97% were obtained. The product was a 1:1 molar mixture of the cis/trans isomers. The characteristic absorptions in the NMR spectra were as follows: $^{19}$F-NMR: −60.2, −61.3, −62.2 and −63.3 ppm. $^{1}$H-NMR: 6.80, 6.45 and 6.25 ppm.

Example 14a
2-(1-Chloro-2,2,2-trifluoroethyl)-2-trifluoromethyl-4-hydroxy-1,3-benzodioxole 15 g of the product of Example 13a were dissolved in 50 ml of acetonitrile and the solution was treated with 1 ml of triethylamine. The mixture was stirred for 15 minutes, the solvent was then stripped off, and the residue was distilled in vacuo. For purification, the product was taken up in diethyl ether and filtered through silicon dioxide. After the diethyl ether had been stripped off, 10.5 g of the product (=70% of theory) remained. The melting point was 139° to 141° C. The characteristic absorptions in the NMR spectra were as follows: $^{19}$F-NMR: −66.6 and −79.3 ppm. $^{1}$H-NMR: 8.4, 6.76, 6.60, 6.50 and 4.70 ppm.

Example 15a
5-Nitro-2-(2,2,2-trifluoroethyl)-2-trifluoromethyl-1,3-benzodioxole A solution of 54.4 g of 2-(2,2,2-trifluoroethyl)-2-trifluoromethyl-1,3-benzodioxole in 75 ml of methylene chloride was added dropwise at 10° C. to a mixture of 40 ml of 65% strength by weight nitric acid and 40 ml of concentrated sulphuric acid. Stirring was continued for 1 hour at room temperature and the batch was then poured into ice-water, the organic phase was separated off, and the aqueous phase was extracted using methylene chloride. The combined organic phases were washed with water, dried and freed from volatile components. 95 g of the product (=86% of theory), which had a melting point of 87° to 88° C., remained. The NMR spectra showed the following characteristic absorptions: $^{19}$F-NMR: −59.0 and −69.4 ppm. $^{1}$H-NMR: 3.10 ppm.

Example 16a
5-Nitro-2-(1-chloro-2,2,2-trifluoroethyl)-2-trifluoromethyl-1,3-benzodioxole 613 g of 2-(1-chloro-2,2,2-trifluoroethyl)-2-trifluoromethyl-1,3-benzodioxole of Example 2a were dissolved in 1.2 l of methylene chloride and the solution was added dropwise at 0° to 10° C. to a mixture of 400 ml of 65% strength nitric acid and 400 ml of concentrated sulphuric acid. Stiring was continued for 2 hours at room temperature. Then, the mixture was poured carefully into 2 l of ice-water and extracted using methylene chloride. The combined organic phases were washed twice using water, dried and concentrated. The yield was 652 g (93% of theory). The NMR spectra showed the following characteristic absorptions: $^{19}$F-NMR: −66.4 and −79.2 ppm. $^{1}$H-NMR: 4.81 ppm.

Example 17a
5,6-Dinitro-2-(2,2,2-trifluoroethyl)-2-trifluoromethyl-1,3-benzodioxole 317 g of the product of Example 15a were introduced, and a mixture of 250 ml of 100% strength by weight nitric acid and 350 ml of concentrated sulphuric acid were added dropwise, with stirring. The mixture was stirred for 2 hours at 55° C. The batch was then allowed to cool and poured into ice-water. The product was extracted using methylene chloride, and the methylene chloride phase was washed until neutral using sodium hydrogencarbonate solution, dried and freed from readily volatile components on a rotary evaporator. The yield was 339 g (=94% of theory), and the melting point was 101° to 103° C.

The NMR spectra showed the following characteristic absorptions: $^{19}$F-NMR: −60.9 and −86.5 ppm. $^{1}$H-NMR: 3.18 ppm.

Example 18a
5,6-Dinitro-2-(1-chloro-2,2,2-trifluoroethyl)-2-trifluoromethyl-1,3-benzodioxole 352 g of 5-nitro-2-(1-chloro-2,2,2-trifluoroethyl)-2-trifluoromethyl-1,3-benzodioxole of Example 16a were introduced and treated with a mixture of 250 ml of 100% strength by weight nitric acid and 350 ml of concentrated sulphuric acid. The mixture was stirred for 2 hours at 60° C. After cooling, the mixture was poured into ice-water and extracted using methylene chloride. The methylene chloride phase was washed with sodium hydrogencarbonate solution and dried and then evaporated on a rotary evaporator. The yield was 392 g (91% of theory), and the melting point was 125° C. The NMR spectra showed the following characteristic absorptions: $^{19}$F-NMR: −68.5 and −81.0 ppm. $^{1}$H-NMR: 4.86 ppm.

Example 19a
5-Amino-2-(2,2,2-trifluoroethyl)-2-trifluoromethyl-1,3-benzodioxole 57.4 g of the product of Example 15a were dissolved in 400 ml of tetrahydrofuran and hydrogenated with hydrogen for 5 hours at 30° C. at 50 bar in the presence of 4 g of catalyst (palladium on charcoal, 10% strength by weight). The mixture was then subjected to filtration, the solvent was removed and the residue was distilled under a high vacuum. This gave 37 g of product (=63% of theory) having a boiling point of 83° C. at 0.07 mbar. $^{19}$F-NMR: −59.0 and −84.6 ppm. $^{1}$H-NMR: 2.98 ppm.

Example 20a

5-Amino-2-(1-chloro-2,2,2-trifluoroethyl)-2-trifluoromethyl-1,3-benzodioxole 72 g of 5-nitro-2-(1-chloro-2,2,2-trifluoroethyl)-2-trifluoromethyl-1,3-benzodioxole of Example 16a were dissolved in 500 ml of tetrahydrofuran and hydrogenated for 5 hours at room temperature with 15 to 20 bar hydrogen using 5 g of palladium on charcoal (5% strength). The mixture was subsequently filtered and the solvent was stripped off in vacuo. The yield was 60 g (93% of theory), and the boiling point was 80° to 82° C. at 0.1 mbar. The NMR spectra showed the following characteristic absorptions: $^{19}$F-NMR: −66.5 and −79.4 ppm. $^{1}$H-NMR: 4.68 ppm.

Example 21a 5,6-Diamino-2-(2,2,2-trifluoroethyl)-2-trifluoromethyl-1,3-benzodioxole 339 g of the product of Example 17a were dissolved in 2000 ml of tetrahydrofuran and treated with 20 g of catalyst (palladium on charcoal, 5% strength by weight). The mixture was hydrogenated with hydrogen for 13 hours at 25 to 30 bar and at room temperature. The batch was then filtered and the solvent was stripped off in vacuo. A solid remained. The yield was 274 g (=96% of theory). $^{19}$F-NMR: −61.2 and −86.6 ppm. $^{1}$H-NMR: 3.02 ppm.

Example 22a 2-(2,2,2-Trifluoroethyl)-2-trifluoromethyl-1,3-benzodioxole 306.5 g of 2-(1-chloro-2,2,2-trifluoroethyl)-2-trifluoromethyl-1,3-benzodioxole of Example 2a were dissolved in 500 ml of THF and the solution was treated with 101 g of triethylamine and 30 g of palladium on charcoal (5% strength by weight). The mixture was then hydrogenated for 48 hours at 110° C. under 100 bar hydrogen. The mixture was subsequently filtered, the solvent was stripped off, and the residue was subjected to fractionation in vacuo. The yield was 126 g (46% of theory), and the boiling point was 60° C. at 10 mbar. The NMR spectra showed the following characteristic absorptions: $^{19}$F-NMR: −59.0 and −84.6 ppm. $^{1}$H-NMR: 3.02 ppm.

Fluoroalkyl(ene) group-containing o-phenylenediamines of the formula

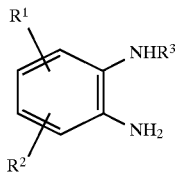

in which
$R^1$ represents $CF_3$, $OCF_3$, $SCF_3$, $SO_2$—$C_1$–$C_6$-alkyl, which can be straight-chain or branched and fully or partially substituted by fluorine, $N(CF_3)_2$, a phenyl or phenoxy radical with $CF_3$ or CN in the 4-position and, if appropriate, other substituents, 1,1,2,3,3,3-hexafluoropropoxy, 1,1,2-trifluoro-2-chloro-ethoxy, 1,1,2,2-tetrafluoroethoxy, 1,1,2-trifluoro-2-chloro-ethylthio or 1,1,2,3,3,3-hexafluoropropylthio, $R^2$ independently of $R^1$ represents F, Cl, Br, CN, $CH_3$, $OCF_3$, $SO_2$—$C_1$–$C_6$-alkyl, which can be straight-chain or branched and fully or partially substituted by fluorine, COO—$C_1$–$C_6$-alkyl, $COOC_6H_5$, 1,1,2,2-tetrafluoroethoxy, 1,1,2,3,3,3-hexafluoropropoxy or 1,1,2-trifluoro-2-chloro-ethoxy and $R^3$ represents hydrogen, $COCH_3$ or $COCF_3$, it being possible for $R^1$ and $R^2$ together to represent a —O—CFCl—CFCl—O-radical, with the exception of the compounds described in EP-A 251,013 and EP-A 487,286, can be obtained by dinitrating a benzene derivative of the formula

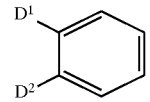

in which
$D^1$ represents $CF_3O$, $CF_3S$, $CHF_2CF_2O$, $CHFCl$—$CF_2O$, $CF_3CHFCF_2O$, $CF_3CF_2O$, $CF_3CF_2CF_2O$, $CF_3CF_2S$ or $CF_3CHFCF_2O$ and $D^2$ represents $CF_3O$, $CF_3S$, $CHF_2CF_2O$, $CHFCl$—$CF_2O$, $CF_3CHF$—$CF_2O$, $CF_3CF_2O$, $CF_3CF_2CF_2O$, $CF_3CF_2S$, $CF_3CHFCF_2O$, fluorine, chlorine, bromine, $C_1$–$C_6$-alkyl or $C_1$–$C_6$-alkoxy, subsequently reducing the nitro groups and thus obtaining compounds in which $R^1$ and $R^2$ are in the 4- and 5-position relative to the amino groups and have the meanings of $D^1$ and $D^2$.

If it is desired to prepare compounds in which $R^1$ has the abovementioned meaning and is in the 4-position relative to the amino groups and $R^2$ represents Cl or Br in the 5-position relative to the amino groups, it is possible, for example, to react a nitrobenzene derivative of the formula

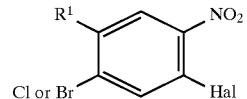

in which
$R^1$ has the abovementioned meaning and

Hal represents fluorine, chlorine or bromine,
with ammonia to exchange the Hal group for an amino group, and to reduce the resulting nitraniline.

If it is desired to prepare compounds in which $R^1$ has the abovementioned meaning and is in the 4-position relative to the amino groups, $R^2$ represents chlorine or bromine in the 6-position relative to the amino groups and $R^3$ denotes hydrogen, it is possible, for example, to react a nitraniline of the formula

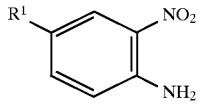

in which
$R^1$ has the abovementioned meaning.
with a chlorinating or brominating agent thus introducing a chlorine or bromine atom into the meta-position relative to the nitro group, and subsequently to reduce the nitro group.

If it is desired to prepare compounds in which $R^1$ denotes a donor group in the 4-position relative to the two amino groups, $R^2$ denotes an acceptor group, for example COO—

$C_1$–$C_6$-alkyl, CN, $CF_3$ or $SO_2$—$C_1$–$C_6$-alkyl and $R_3$ is other than hydrogen, it is possible, for example, to mononitrate a benzene derivative of the formula

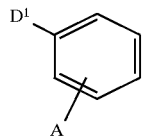

in which $D^1$ has the abovementioned meaning and

A represents $CF_3$, $SO_2$—$C_1$–$C_6$-alkyl, which can be straight-chain or branched and fully or partially substituted by fluorine, or represents COO—$C_1$–$C_6$-alkyl or CN, (the $NO_2$ group enters in the para-position relative to $D^1$), to reduce the $NO_2$ group to the $NH_2$ group, to acrylate the $NH_2$ group, for example with acetic acid or trifluoroacetic acid, to carry out another mononitration reaction (this $NO_2$ group enters in the ortho-position relative to the NHCOR group in which R is, for example, $CH_3$ or $CF_3$), to reduce this $NO_2$ group to the $NH_2$ group and, if appropriate, if it is desired to prepare a compound of the above formula where $R^3$ is hydrogen, to eliminate the acyl group by hydrolysis.

The fluoroalkyl(ene)-group containing phenylenediamines in which $R^3$ denotes hydrogen can be initially reacted with trifluoroacetic acid to give 2-trifluoromethylbenzimidazoles of the formula

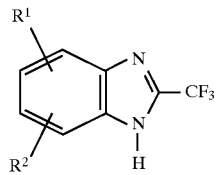

and these can then be reacted further with compounds of the formula

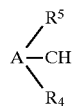

in which $R^1$ and $R^2$ assume the scope of the above meanings, $R^4$ represents hydrogen, alkyl, alkoxy or optionally substituted aryl, $R^5$ represents hydroxyl, cyano or in each case optionally substituted alkyl, alkenyl, alkinyl, alkoxy, alkenyloxy, alkinyloxy, alkylthio, amino, aminocarbonyl, alkylcarbonyl, alkoxycarbonyl, alkylcarbonyloxy, dialkoxyphosphonyl, (hetero)aryl, (hetero)arylcarbonyl, (hetero)aryloxycarbonyl, hetero)arylcarbonyloxy or hetero)arylaminocarbonylaminocarbonyloxy and A denotes a suitable leaving group.

Leaving groups are known to a person skilled in the art, examples being halogen, alkyl(alkoxy, aryl)sulphonyloxy, hydroxyl or alkoxy.

EXAMPLES

Examples 1b to 6b (Dinitration and reduction)

Example 1b 320 g of 1,2-bis-(2-chloro-1,1,2-trifluoroethoxy)-benzene were added dropwise to 500 g of a mixed acid containing 33% strength by weight $HNO_3$ and 67% strength by weight $H_2SO_4$. After one hour at 40° C., 250 ml of 20% strength by weight oleum were added dropwise. The mixture was subsequently heated at 80° C., and stirring was continued for 15 hours. A further 120 ml of 20% strength by weight oleum and 250 g of the abovementioned mixed acid were then added dropwise. After 6 hours at 80° to 82° C., the mixture was cooled and poured onto ice. The organic phase was separated off and washed with water. After azeotropic drying using 1,2-dichloroethane, 350 g of 96% by weight pure 1,2-dinitro-4,5-bis-(2-chloro-1,1,2-trifluoroethoxy)-benzene were obtained (oil, $n_D^{20}$: 1.4832, GC 99. 1%) 350 g of this dinitro compound were added dropwise to a mixture of 1.5 l of ethanol, 50 ml of water, 30 ml of concentrated aqueous hydrochloric acid and 470 g of iron filings, and the mixture was refluxed for a total of 15 hours. When cold, the solution was filtered and concentrated and the residue was recrystallized from cyclohexane. 216 g of 1,2-diamino-4,5-bis-(2-chloro-1,1,2-trifluoroethoxy)-benzene having a melting point of 58° to 60° C. were obtained.

Example 2b

Analogously to Example 1, 1,2-bis-1,1,2,3,3,3-hexafluoropropoxy)-benzene was used to prepare the corresponding 4,5-dinitro compound (oil, $n_D^{20}$: 1.4852) and the corresponding 4,5-diamino compound (oil, 87% by weight pure).

Example 3b

Analogously to Example 1, 1-(1,1,2-trifluoro-2-chloroethoxy)-2-chlorobenzene was used to prepare the corresponding 4,5 dinitro compound (melting point 56° to 57° C.) and the corresponding 4,5-diamino compound (melting point 67° to 68° C.).

Example 4b

Analogously to Example 1, 1-trifluoromethoxy-2-bromobenzene was used to prepare the corresponding 4,5-dinitro compound (melting point 73° to 75° C.) and the corresponding 4,5-diamino compound (oil, purity 98% by weight, $n_D^{20}$: 1.5485).

Example 5b

Analogously to Example 1, 1-trifluoromethoxy-2-chlorobenzene was used to prepare the corresponding 4,5-dinitro compound (melting point 55° to 56° C.) and the corresponding 4,5-amino compound (melting point 56°–57° C.).

Example 6b 1-(1,1,2,3,3,3-Hexafluoropropoxy-2-chloro-benzene was used to prepare the corresponding 4,5-dinitro compound (oil) and the corresponding 4,5-diamino compound (oil).

Examples 7b to 12b

Treatment with ammonia under pressure and reduction

Example 7b 260 g of 3-nitro-2,5-dichlorobenzotrifluoride, 130 ml of water and 10 g of tetraethylammonium chloride were introduced into an autoclave, and 120 ml of liquid ammonia were injected. The mixture was then heated to 130° C. and stirred for 10 hours at this temperature. After cooling, the batch was filtered and the precipitate which had been separated off was washed with water and dried. 194 g of 2-amino-3-nitro-5-chloro-benzotrifluoride with a melting point of 67° C. were obtained.

134 g of the nitraniline obtained as described above were dissolved in 800 ml of ethanol, and 20 ml of water, 10 ml of concentrated aqueous hydrochloric acid and 160 g of iron filings were then added. The mixture was refluxed for 15 hours and then cooled, and subjected to filtration with suction, the filter residue was washed with dichloromethane, and the organic phases were subsequently freed from the solvent under reduced pressure. 171 g of 5-chloro-3-trifluoromethyl-1,2-diaminobenzene with a melting point of 53° C. were obtained.

Example 8b

Analogously to Example 7, 3-nitro4,6-dichloro-difluorochloromethoxybenzene was used to obtain first 3-nitro-4-amino-6-chloro-difluorochloromethoxyberzene (melting point 73° C.) and therefrom 3,4-diamino-chloro-difluorochloromethoxy-benzene (oil).

Example 9b

Analogously to Example 7, 3-bromo-5-nitro-6-chlorobenzotrifluoride was used to prepare first 3-bromo-5-nitro-6-amino-benzotrifluoride (melting point 80° to 82° C.) and therefrom 3-bromo-5,6-diamino-benzotrifluoride (melting point 52° to 54° C.).

Example 10b

Analogously to Example 7, 3-cyano-4-chloro-5-nitro-benzotrifluoride was used to prepare first 3-cyano-4-amino-5-nitro-benzotrifluoride (melting point 99° to 100° C.) and therefrom 3-cyano-4,5-diamino-benzotrifluoride.

Example 11b

Analogously to Example 7, 3,6-dichloro-5-nitro-benzotrifluoride was used to prepare first 3-chloro-5-nitro-6-amino-benzotrifluoride (melting point 53° to 54° C.) and therefrom 3-chloro-5,6-diamino-benzotrifluoride.

Example 12b

2-Bromo-4-fluoro-5-nitro-(1,1,2-trifluoro-2-chloro)-ethoxybenzene was used to prepare first 2-bromo-4-amino-5-nitro-(1,1,2-trifluoro-2-chloro-ethoxy)-benzene (melting point 90° C.) and therefrom 2-bromo4,5-diamino-(1,1,2-trifluoro-2-chloro)-ethoxybenzene.

Example 13

(Halogenation of a nitraniline and reduction)

24 g of finely pulverulent 2-nitro-4-trifluoromethylmercaptoaniline were dissolved in 50 ml of tri-fluoroacetic acid, and 18 g of bromine were metered in at 20° C. Stirring was then continued for 3 hours at 20° C. and for a further 30 minutes at 40° C. The mixture poured into water and the product taken up in dichloromethane. After the solvent had been removed, 31 g of 6-bromo-2-nitro-4-trifluoromethyl-mercapto-aniline were obtained.

155 g of the nitraniline thus prepared were refluxed for 15 hours with 15 ml of water, 10 ml of concentrated aqueous hydrochloric acid and 70 g of iron filings in 700 ml of ethanol, the mixture was then filtered, the filtrate was freed from the solvent under reduced pressure and the solid crude product was recrystallized from cyclohexane. 112 g of 6-bromo-4-trifluoromethyl-mercapto-1,2-diaminobenzene with a melting point of 60° to 61° C. were obtained.

Example 14b

Analogously to Example 13, 27 g of 2-nitro-4-trifluoromethyl-sulphonylaniline in 100 ml of acetic acid were brominated with 18 g of bromine.

After working up, 32 g of 2-nitro-6-bromo-4-trifluoromethylsulphonyl-anialine were obtained. Melting point 147° C.

32 g of the nitramine thus prepared were reduced with iron filings in alcohol and aqueous hydrochloric acid. 24 g of 3-bromo-5-trifluoromethylsulphonyl-phenylene-1,2-diamine were obtained, melting point 155°–157° C.

Example 15b

Analogously to Example 14, 27 g of 2-nitro-4-trifluoromethylsulphonyl-aniline in 100 ml of acetic acid were chlorinated with 10 g of chlorine. 29 g of 2-nitro-4-trifluoromethylsulphonyl-6-chloro-aniline were obtained, melting point: 138°–139° C.

13 g of 3-chloro-5-trifluoromethylsulphonyl-1,2-phenylenediamine (melting point: 143°–145° C.) were obtained by reduction.

Examples 16 to 20

Nitration and reduction in 2 steps)

Example 16

263 g of 4-(2,6-dichloro-4-trifluoromethyl)-phenoxy-acetanilide were dissolved in 1100 ml of dichloromethane and introduced at 10° C. 88 g of 98% strength by weight nitric acid were then added dropwise at this temperature. Stirring was continued for 1 hour at 10° C. and for 2 more hours at 30° C. After 300 ml of water had been added, the phases were separated and the organic phase was freed from dichloromethane under reduced pressure. 253 g of 2-nitro-4-(2,6-dichloro-4-trifluoromethylphenoxy)-acetanilide with a melting point of 138°–140° C. remained.

91 g of the acetanilide thus prepared were dissolved in 800 ml of dioxane, 10 g of Raney nickel were added, and the mixture was hydrogenated at 25° to 45° C. in a hydrogenation apparatus with a maximum hydrogen pressure of 50 bar. After releasing the pressure and filtration, the dioxane was distilled off under a slight vacuum. 65 g of 2-amino-4-(2,6-dichloro-4-trifluoromethyl-phenoxy)acetanilide with a melting point of 222°–223° C. remained.

Example 17

Analogously to Example 16, 3-trifluoromethyl-4-methoxy-acetanilide was used to prepare first 3-trifluoromethyl-4-methoxy-6-nitro-acetanilide (melting point 143°–144° C.) and therefrom 3-trifluoromethyl-4-methoxy-6-amino-acetanilide (melting point 164°–165° C.).

Example 18

Analogously to Example 16, 3-trifluoromethyl-4-fluoro-trifluoromethylacetanilide was used to prepare first 3-trifluoromethyl-4-fluoro-6-nitro-trifluoromethylacetanilide (melting point 78° C.) and therefrom 3-trifluoromethyl-4-fluoro-6-amino-trifluoromethylacetanilide (melting point 92°–93° C.).

Example 19

Analogously to Example 16, 3-trifluoromethyl-4-bromo-trifluoromethylacetanilide was used to prepare first 3-trifluoromethyl-4-bromo-6-nitro-trifluoromethylacetanilide (melting point 110° to 112° C.) and therefrom 3-trifluoromethyl-4-bromo-6-amino-trifluoromethylacetanilide (melting point 63°–65° C.).

Example 20

Analogously to Example 16, 3-trifluoromethylthio-4-chloro-tri-fluoromethylacetanilide was used to prepare first 3-trifluoromethylthio-4-chloro-6-nitro-trifluoromethylacetanilide (melting point 99°–100° C.) and therefrom 3-trifluoromethylthio-4-chloro-6-amino-trifluoromethylacetanilide (melting point 88°–90° C.).

Example 21

0.2 mol of 3-bromo-5-trifluoromethyl-phenylene-diamine and 150 ml of trifluoroacetic acid were refluxed for 3 hours. For working up, excess trifluoroacetic acid was distilled off and the residue was partitioned between 100 ml of water and 300 ml of ethyl acetate. The organic phase was separated off, washed in succession with in each case 100 ml of aqueous sodium hydrogencarbonate solution and water, dried over sodium sulphate and concentrated in vacuo. The residue was purified by chromatography on silica gel (eluent: cyclohexane/ethyl acetate 1:1).

This gave 4-bromo-6-trifluoromethyl-2-trifluoromethyl-1H-benzimidazole of melting point 149°–151° C.

Example 22

0.03 mol of 4-bromo-6-trifluoromethyl-2-trifluoromethyl-1H-benzimidazole and 0.06 mol of pulverulent potassium carbonate were refluxed for 15 minutes in 70 ml of ethyl acetate, 3.9 g (0.04 mol) of chloromethyl methyl thioether in 20 ml of ethyl acetate were then added, and the mixture was refluxed for a further 4 hours, with stirring. For working up, the cooled reaction mixture was washed twice using in each case 40 ml of water, dried over sodium sulphate and concentrated in vacuo, and the residue was purified by chromatography on silica gel (eluent: dichloromethane).

This gave 1-methylthiomethyl-4-bromo-6-trifluoromethyl-2-trifluoromethyl-benzimidazole of melting point 56°–60° C.

Use Examples:

In the Use Examples which follow, the compounds listed below were employed as comparison substances:

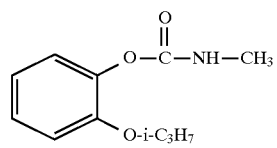
(A)

O-(2-Isopropoxyphenyl) N-methyl-carbamate (compare, for example, DE 1,108,202)

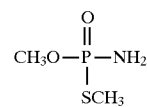
(B)

O,S-Diethyl-thiolo-phosphoramide (compare, for example, DE 1,210,835)

Example A

Phaedon larvae test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), while the leaves are still moist.

After the specified period of time, the destruction in percent is determined. 100% means that all the beetle larvae have been killed; 0% means that none of the beetle larvae have been killed.

In this test, a superior activity compared with the prior art is shown, for example, by the following compounds of the Preparation Examples: 13, 14, 16, 18, 20, 22, 28, 29, 30, 56, 76, 80, 84, 85,.86, 89, 103 and 109.

TABLE A

Phaedon Larvae Test

| Active compounds | | Active compound concentration in % | Degree of destruction in % after 3 days |
|---|---|---|---|
| (structure: O-C(=O)-NH-CH₃ and O-i-C₃H₇ on benzene) (known) | (A) | 0.1 | 100 |
| | | 0.01 | 70 |
| | | 0.001 | 0 |

TABLE A-continued

Phaedon Larvae Test

| Active compounds | Active compound concentration in % | Degree of destruction in % after 3 days |
|---|---|---|
| ![compound] 5-F₃C, 6-Cl, 2-CF₃, N-CH₂—OC₂H₅ benzimidazole + 5-Cl, 6-F₃C, 2-CF₃, N-CH₂—OC₂H₅ benzimidazole | (85) 0.1<br>0.01<br>0.001 | 100<br>100<br>100 |
| 5-F₃C, 6-Cl, 2-CF₃, N-CH₂—OC₂H₅ benzimidazole | (86) 0.1<br>0.01<br>0.001 | 100<br>100<br>100 |
| 5-F₃C, 6-Br, 2-CF₃, N-CH₂—OC₂H₅ benzimidazole + 5-Br, 6-F₃C, 2-CF₃, N-CH₂—OC₂H₅ benzimidazole | (80) 0.1<br>0.01<br>0.001 | 100<br>100<br>100 |
| 5,6-(OCF₂CF₂O), 2-CF₃, N-CH₂—OC₂H₅ benzimidazole | (103) 0.1<br>0.01<br>0.001 | 100<br>100<br>100 |
| 5,6-(OCF₂CF₂O), 2-CF₃, N-CH₂—O—CH₂—C≡CH benzimidazole | (109) 0.1<br>0.01<br>0.001 | 100<br>100<br>100 |
| 5-F₃C, 6-Cl, 2-CF₃, N-CH₂—O-n-C₃H₇ benzimidazole + 5-Cl, 6-F₃C, 2-CF₃, N-CH₂—O-n-C₃H₇ benzimidazole | (89) 0.1<br>0.01<br>0.001 | 100<br>100<br>100 |

TABLE A-continued
Phaedon Larvae Test
| Active compounds | Active compound concentration in % | Degree of destruction in % after 3 days |
|---|---|---|
| 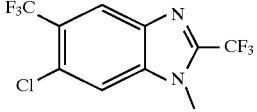 + 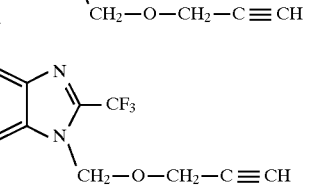 | (90) 0.1<br>0.01<br>0.001 | 100<br>100<br>100 |
| 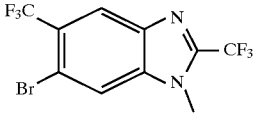 + 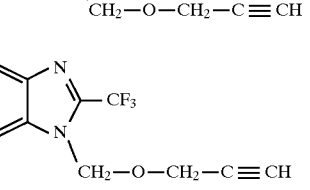 | (84) 0.1<br>0.01<br>0.001 | 100<br>100<br>100 |
| 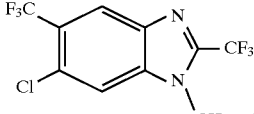 + 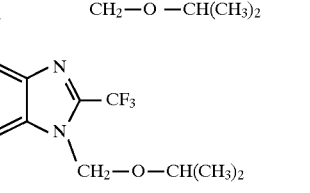 | (56) 0.1<br>0.01<br>0.001 | 100<br>100<br>100 |
| 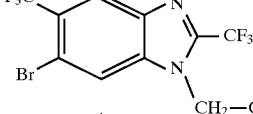 + 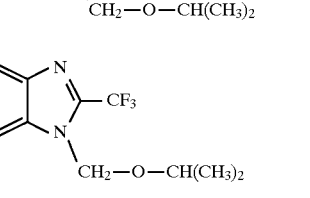 | (76) 0.1<br>0.01<br>0.001 | 100<br>100<br>100 |

TABLE A-continued

Phaedon Larvae Test

| Active compounds | Active compound concentration in % | Degree of destruction in % after 3 days |
|---|---|---|
| (13) 4-Br, 6-CF$_3$-benzimidazole, 2-CF$_3$, N-CH$_2$-O-CH(CH$_3$)$_2$ + 5-CF$_3$, 7-Br-benzimidazole, 2-CF$_3$, N-CH$_2$-O-CH(CH$_3$)$_2$ | 0.1<br>0.01<br>0.001 | 100<br>100<br>100 |
| (14) 4-Br, 6-CF$_3$-benzimidazole, 2-CF$_3$, N-CH$_2$-O-n-C$_3$H$_7$ + 5-CF$_3$, 7-Br-benzimidazole, 2-CF$_3$, N-CH$_2$-O-n-C$_3$H$_7$ | 0.1<br>0.01<br>0.001 | 100<br>100<br>100 |
| (16) 4-Br, 6-CF$_3$-benzimidazole, 2-CF$_3$, N-CH$_2$-O-CH$_2$-C≡CH | 0.1<br>0.01<br>0.001 | 100<br>100<br>100 |
| (18) 4-Br, 6-CF$_3$-benzimidazole, 2-CF$_3$, N-CH$_2$-O-CO-C(CH$_3$)$_3$ | 0.1<br>0.01<br>0.001 | 100<br>100<br>100 |
| (20) 4-Br, 6-CF$_3$-benzimidazole, 2-CF$_3$, N-CH$_2$-O-C$_2$H$_5$ + 5-CF$_3$, 7-Br-benzimidazole, 2-CF$_3$, N-CH$_2$-O-C$_2$H$_5$ | 0.1<br>0.01<br>0.001 | 100<br>100<br>100 |

TABLE A-continued

Phaedon Larvae Test

| Active compounds | Active compound concentration in % | Degree of destruction in % after 3 days |
|---|---|---|
| 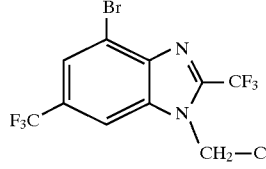 (22) | 0.1<br>0.01<br>0.001 | 100<br>100<br>100 |
| 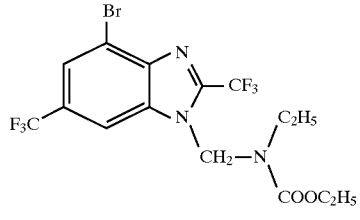 (28) | 0.1<br>0.01<br>0.001 | 100<br>100<br>100 |
| 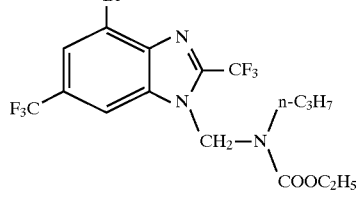 (29) | 0.1<br>0.01<br>0.001 | 100<br>100<br>100 |
| 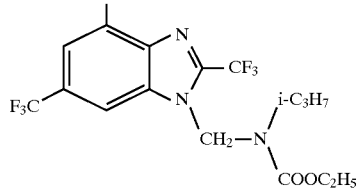 (30) | 0.1<br>0.01<br>0.001 | 100<br>100<br>100 |

Example B

Plutella test
Solvent: 7 parts by weight of diethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of this diamond-back moth (*Plutella maculipennis*) while the leaves are still moist.

After the specified period of time, the destruction in percent is determined. 100% means that all the caterpillars have been killed; 0% means that none of the caterpillars have been killed.

In this test, a superior activity compared with the prior art is shown, for example, by the following compounds of the Preparation Examples: 2, 3, 13, 14, 18, 20, 21, 28, 29, 30, 52, 56, 76, 80, 84, 85, 86, 103, 109 and 131.

TABLE B

Plutella Test

| Active compounds | Active compound concentration in % | Degree of destruction in % after 3 days |
|---|---|---|
| (A) 2-isopropoxyphenyl N-methylcarbamate (known) | 0.1<br>0.01<br>0.001 | 100<br>100<br>10 |
| (85) 5-CF$_3$-6-Cl-2-CF$_3$-1-(CH$_2$OC$_2$H$_5$)-benzimidazole + 5-Cl-6-CH$_3$-2-CF$_3$-1-(CH$_2$OC$_2$H$_5$)-benzimidazole | 0.1<br>0.01<br>0.001 | 100<br>100<br>100 |
| (86) 5-CF$_3$-6-Cl-2-CF$_3$-1-(CH$_2$OC$_2$H$_5$)-benzimidazole | 0.1<br>0.01<br>0.001 | 100<br>100<br>100 |
| (84) 5-CF$_3$-6-Br-2-CF$_3$-1-(CH$_2$-O-CH$_2$-C≡CH)-benzimidazole + 5-Br-6-CH$_3$-2-CF$_3$-1-(CH$_2$-O-CH$_2$-C≡CH)-benzimidazole | 0.1<br>0.01<br>0.001 | 100<br>100<br>100 |
| (80) 5-CF$_3$-6-Br-2-CF$_3$-1-(CH$_2$OC$_2$H$_5$)-benzimidazole + 5-Br-6-CH$_3$-2-CF$_3$-1-(CH$_2$OC$_2$H$_5$)-benzimidazole | 0.1<br>0.01<br>0.001 | 100<br>100<br>100 |
| (103) 5,6-(OCF$_2$CF$_2$O)-2-CF$_3$-1-(CH$_2$OC$_2$H$_5$)-benzimidazole | 0.1<br>0.01<br>0.001 | 100<br>100<br>100 |

TABLE B-continued

Plutella Test

| Active compounds | Active compound concentration in % | Degree of destruction in % after 3 days |
|---|---|---|
| (109) structure: F₂C-O / F₂C-O fused benzimidazole, 2-CF₃, N-CH₂—O—CH₂—C≡CH | 0.1<br>0.01<br>0.001 | 100<br>100<br>100 |
| (131) structure: CF₃-O, CF₃-O benzimidazole, 2-CF₃, N-CH₂—O—CH₂—C≡CH | 0.1<br>0.01<br>0.001 | 100<br>100<br>100 |
| (52) structure: Cl, CF₃ benzimidazole, 2-CF₃, N-CH₂—CN | 0.1<br>0.01<br>0.001 | 100<br>100<br>100 |
| (56) structure: F₃C, Cl benzimidazole, 2-CF₃, N-CH₂—O—CH(CH₃)₂<br>+<br>Cl, F₃C benzimidazole, 2-CF₃, N-CH₂—O—CH(CH₃)₂ | 0.1<br>0.01<br>0.001 | 100<br>100<br>100 |
| (76) structure: F₃C, Br benzimidazole, 2-CF₃, N-CH₂—O—CH(CH₃)₂<br>+<br>Br, F₃C benzimidazole, 2-CF₃, N-CH₂—O—CH(CH₃)₂ | 0.1<br>0.01<br>0.001 | 100<br>100<br>100 |
| (2) structure: Br, CF₃ benzimidazole, 2-CF₃, N-CH₂—N(CH₃)(COOCH₃) | 0.1<br>0.01<br>0.001 | 100<br>100<br>100 |
| (3) structure: Br, CF₃ benzimidazole, 2-CF₃, N-CH₂—N(C₂H₅)(COOCH₃) | 0.1<br>0.01<br>0.001 | 100<br>100<br>100 |

TABLE B-continued
Plutella Test
| Active compounds | Active compound concentration in % | Degree of destruction in % after 3 days |
|---|---|---|
| 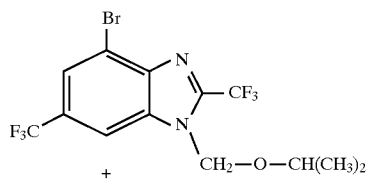 (13) | 0.1<br>0.01<br>0.001 | 100<br>100<br>100 |
| 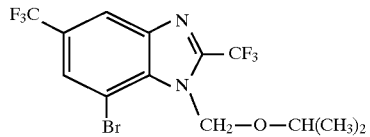 (14) | 0.1<br>0.01<br>0.001 | 100<br>100<br>100 |
| 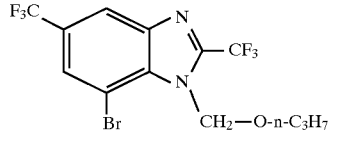 (18) | 0.1<br>0.01<br>0.001 | 100<br>100<br>100 |
| 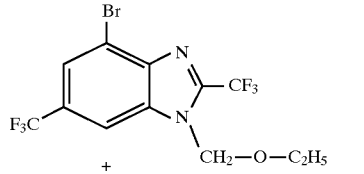 (20) | 0.1<br>0.01<br>0.001 | 100<br>100<br>100 |
| 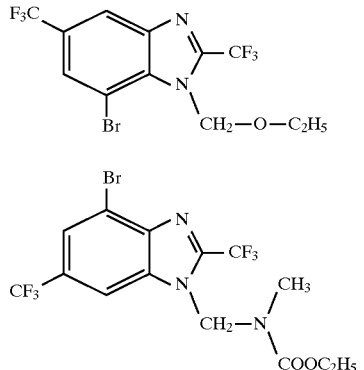 (21) | 0.1<br>0.01<br>0.001 | 100<br>100<br>100 |

TABLE B-continued

Plutella Test

| Active compounds | Active compound concentration in % | Degree of destruction in % after 3 days |
|---|---|---|
| (28) Br-benzimidazole with CF$_3$, F$_3$C, CH$_2$-N(C$_2$H$_5$)(COOC$_2$H$_5$) | 0.1<br>0.01<br>0.001 | 100<br>100<br>100 |
| (29) Br-benzimidazole with CF$_3$, F$_3$C, CH$_2$-N(n-C$_3$H$_7$)(COOC$_2$H$_5$) | 0.1<br>0.01<br>0.001 | 100<br>100<br>100 |
| (30) Br-benzimidazole with CF$_3$, F$_3$C, CH$_2$-N(i-C$_3$H$_7$)(COOC$_2$H$_5$) | 0.1<br>0.01<br>0.001 | 100<br>100<br>100 |

Example C

Heliothis virescens Test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soya shoots (*Glycine max*) are treated by being dipped into the preparation of active compound of the desired concentration and are infested with the tobacco budworm (*Heliothis virescens*) while the leaves are still moist.

After the specified period of time, the destruction in percent is determined. 100% means that all the worms have been killed; 0% means that none of the worms have been killed.

In this test, a superior activity compared with the prior art is shown, for example, by the following compounds of the Preparation Examples: 3, 13, 16, 18, 20, 52, 53, 56, 76, 80, 84, 85, 86, 89, 90, 103, 109 and 131.

TABLE C

Heliothis virescens Test

| Active compounds | Active compound concentration in % | Degree of destruction in % after 3 days |
|---|---|---|
| (A) Phenyl-O-C(=O)-NH-CH$_3$ with O-i-C$_3$H$_7$ (known) | 0.1 | 10 |

TABLE C-continued
Heliothis virescens Test
| Active compounds | Active compound concentration in % | Degree of destruction in % after 3 days |
|---|---|---|
| 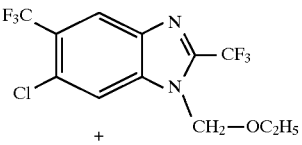 | (85) 0.1 | 100 |
| 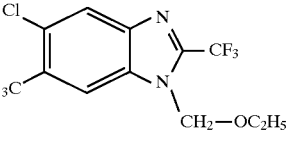 | (86) 0.1 | 100 |
| 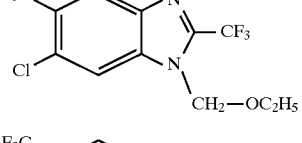 | (84) 0.1 | 100 |
| 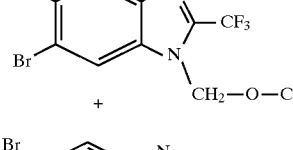 | (80) 0.1 | 100 |
| 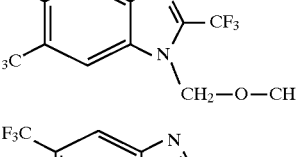 | (103) 0.1 | 100 |
| 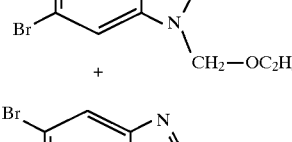 | (109) 0.1 | 100 |
| 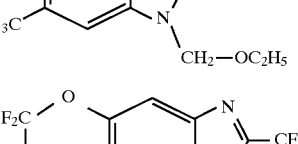 | (131) 0.1 | 100 |

TABLE C-continued

*Heliothis virescens* Test

| Active compounds | Active compound concentration in % | Degree of destruction in % after 3 days |
|---|---|---|
| (89) Structure: 5-CF$_3$, 6-Cl benzimidazole, 2-CF$_3$, N-CH$_2$-O-n-C$_3$H$_7$ + 5-Cl, 6-CF$_3$ benzimidazole, 2-CF$_3$, N-CH$_2$-O-n-C$_3$H$_7$ | 0.1 | 100 |
| (90) Structure: 5-CF$_3$, 6-Cl benzimidazole, 2-CF$_3$, N-CH$_2$-O-CH$_2$-C≡CH + 5-Cl, 6-CF$_3$ benzimidazole, 2-CF$_3$, N-CH$_2$-O-CH$_2$-C≡CH | 0.1 | 100 |
| (52) Structure: 5-Cl, 6-CF$_3$ benzimidazole, 2-CF$_3$, N-CH$_2$-CN | 0.1 | 100 |
| (53) Structure: 5-CF$_3$, 6-Cl benzimidazole, 2-CF$_3$, N-CH$_2$-CN | 0.1 | 100 |
| (56) Structure: 5-CF$_3$, 6-Cl benzimidazole, 2-CF$_3$, N-CH$_2$-O-CH(CH$_3$)$_2$ + 5-Cl, 6-CF$_3$ benzimidazole, 2-CF$_3$, N-CH$_2$-O-CH(CH$_3$)$_2$ | 0.1 | 100 |
| (76) Structure: 5-CF$_3$, 6-Br benzimidazole, 2-CF$_3$, N-CH$_2$-O-CH(CH$_3$)$_2$ + 5-Br, 6-CF$_3$ benzimidazole, 2-CF$_3$, N-CH$_2$-O-CH(CH$_3$)$_2$ | 0.1 | 100 |

TABLE C-continued

Heliothis virescens Test

| Active compounds | Active compound concentration in % | Degree of destruction in % after 3 days |
|---|---|---|
| (3) 4-Br, 6-CF₃, 2-CF₃-benzimidazole, N-CH₂-N(C₂H₅)(COOCH₃) | 0.1 | 100 |
| (13) 4-Br, 6-CF₃, 2-CF₃-benzimidazole, N-CH₂-O-CH(CH₃)₂ + 4-CF₃, 7-Br, 2-CF₃-benzimidazole, N-CH₂-O-CH(CH₃)₂ | 0.1 | 100 |
| (16) 4-Br, 6-CF₃, 2-CF₃-benzimidazole, N-CH₂-O-CH₂-C≡CH | 0.1 | 100 |
| (18) 4-Br, 6-CF₃, 2-CF₃-benzimidazole, N-CH₂-O-CO-C(CH₃)₃ | 0.1 | 100 |
| (20) 4-Br, 6-CF₃, 2-CF₃-benzimidazole, N-CH₂-O-C₂H₅ + 5-CF₃, 7-Br, 2-CF₃-benzimidazole, N-CH₂-O-C₂H₅ | 0.1 | 100 |

Example D

Tetranychus test (OP-resistant)
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water containing emulsifier to the desired concentrations.

Bean plants (*Phaseolus vulgaris*) which are heavily infested with all development stages of the greenhouse red spider mite (*Tetranychus urticae*) are dipped into a preparation of active compound of the desired concentration, After the specified period of time, the destruction in percent is determined. 100% means that all the spider mites have been killed; 0% means that none of the spider mites have been killed.

In this test, a superior activity compared with the prior art is shown, for example, by the following compounds of the Preparation Examples: 2, 3, 4, 16, 20, 83 and 84.

TABLE D

Tetranychus Test (OP-resistant)

| Active compounds | | Active compound concentration in % | Degree of destruction in % after 7 days |
|---|---|---|---|
| $CH_3O-\underset{\underset{SCH_3}{|}}{\overset{\overset{O}{\|}}{P}}-NH_2$ (Known) | (B) | 0.01<br>0.001 | 60<br>0 |
| [benzimidazole with F$_3$C, Br, CF$_3$, CH$_2$-O-CH$_2$-C≡CH] + [benzimidazole with Br, F$_3$C, CF$_3$, CH$_2$-O-CH$_2$-C≡CH] | (84) | 0.01<br>0.001 | 100<br>95 |
| [benzimidazole with Br, CF$_3$, CF$_3$, CH$_2$-N(CH$_3$)(COOCH$_3$)] | (2) | 0.01<br>0.001 | 100<br>45 |
| [benzimidazole with Br, CF$_3$, CF$_3$, CH$_2$-N(C$_2$H$_5$)(COOCH$_3$)] | (3) | 0.01<br>0.001 | 100<br>60 |
| [benzimidazole with Br, CF$_3$, CF$_3$, CH$_2$-N(n-C$_3$H$_7$)(COOCH$_3$)] | (4) | 0.01<br>0.001 | 100<br>60 |
| [benzimidazole with Br, CF$_3$, F$_3$C, CH$_2$-O-CH$_2$-C≡CH] | (16) | 0.01<br>0.001 | 100<br>60 |

TABLE D-continued

Tetranychus Test (OP-resistant)

| Active compounds | Active compound concentration in % | Degree of destruction in % after 7 days |
|---|---|---|
| (20) 4-Br, 6-CF$_3$-benzimidazole, 2-CF$_3$, N-CH$_2$-O-C$_2$H$_5$ + 5-CF$_3$, 7-Br-benzimidazole, 2-CF$_3$, N-CH$_2$-O-C$_2$H$_5$ | 0.01<br>0.001 | 98<br>80 |
| (83) 5-CF$_3$, 6-Br-benzimidazole, 2-CF$_3$, N-CH$_2$-O-n-C$_3$H$_7$ + 5-Br, 6-CF$_3$-benzimidazole, 2-CF$_3$, N-CH$_2$-O-n-C$_3$H$_7$ | 0.01<br>0.001 | 100<br>80 |

Example E

Plutella Test
Solvent: 31 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water containing emulsifier to the desired concentration.

Cabbage leaves (*Brassica oleracea*) are treated with the preparation of active compound of the desired concentration. A treated leaf is placed into a plastic dish and infested with larvae ($L_2$) of the diamond-back moth (*Plutella xylostella*). After three days, in each case one untreated leaf is used to continue the feeding of the larvae.

After the specified period of time, the destruction in percent is determined. 100% means that all the animals have been killed; 0% means that none of the spider mites have been killed.

In this test, a superior activity compared with the prior art is shown, for example, by the following compound of the Preparation Examples: 87.

TABLE 3

Plutella Test

| Active compounds | Active compound concentration in % | Degree of destruction in % after 7 days |
|---|---|---|
| (A) phenyl-O-C(=O)-NH-CH$_3$, O-i-C$_3$H$_7$ (known) | 0.01 | 0 |

TABLE 3-continued

Plutella Test

| Active compounds | Active compound concentration in % | Degree of destruction in % after 7 days |
|---|---|---|
| 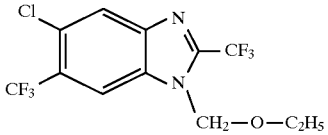 | (87) 0.01 | 100 |

Example F

Phaedon Test

Solvent: 31 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water containing emulsifier to the desired concentration.

Cabbage leaves (*Brassica oleracea*) are treated with the preparation of active compound of the desired concentration. A treated leaf is placed into a plastic dish and infested with larvae ($L_2$) of the mustard beetle (*Phaedon cochleariae*). After three days, in each case one untreated leaf is used to continue the feeding of the larvae.

After the specified period of time, the destruction in percent is determined. 100% means that all the animals have been killed; 0% means that none of the animals have been killed.

In this test, a superior activity compared with the prior art is shown, for example, by the following compound of the Preparation Examples: 87.

Example G

Critical concentration test/nematodes

Test nematode: *Globodera rostochiensis*
Solvent: 31 parts by weight of acetone
Emulsifier: 1 part by weight of alkylaryl polyglycol ether To produce a suitable preparation of active compound, 1 part by weight of active compound is mixed with the stated amount of solvent the stated amount of emulsifier is added and the concentrate is diluted with water to the desired concentration.

The preparation of active compound is intimately mixed with soil which is heavily infested with the test nematodes. The concentration of the active compound in the preparation is of practically no importance here, only the amount of active compound per unit volume of soil, which is given in ppm (=mg/l), being decisive. The treated soil is filled into pots, potatoes are planted therein, and the pots are kept at a greenhouse temperature of 20° C.

After six weeks, the potato roots are examined for cysts and the degree of effectiveness of the active compound is determined in %. The degree of effectiveness is 100% if infestation is avoided completely and 0% if the level of infestation is just as high as in the control plants in untreated, but equally infested, soil.

TABLE F

Phaedon Test

| Active compounds | Active compound concentration in % | Degree of destruction in % after 7 days |
|---|---|---|
| 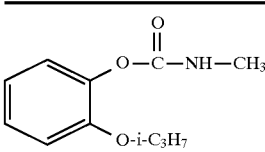<br>(known) | (A) 0.01 | 0 |
| 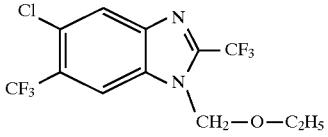 | (87) 0.01 | 100 |

In this test, a superior activity compared with the prior art is shown, for example, by the following compound of the Preparation Examples: 13, 20 and 85.

TABLE G

Nematode Test (*Globodera rostochiensis*)

| Active compounds | | Degree of destruction in % at an active compound concentration of 5 ppm |
|---|---|---|
| [structure: phenyl with O-C(=O)-NH-CH3 and O-i-C3H7] (known) | (A) | 0 |
| [benzimidazole structure: CF3, Cl, CF3, CH2-O-n-C3H7] + [benzimidazole structure: Cl, CF3, CF3, CH2-O-C2H5] | (85) | 100 |
| [benzimidazole structure: Br, CF3, CF3, CH2-O-i-C3H7] + [benzimidazole structure: CF3, CF3, Br, CH2-O-i-C3H7] | (13) | 100 |

TABLE G-continued

Nematode Test (*Globodera rostochiensis*)

| Active compounds | | Degree of destruction in % at an active compound concentration of 5 ppm |
|---|---|---|
| [benzimidazole structure: Br, CF3, CF3, CH2-O-C2H5] + [benzimidazole structure: CF3, CF3, Br, CH2-O-C2H5] | (20) | 100 |

Example H

*Psoroptes ovis* Test

Solvent: 35 parts by weight of ethylene glycol monomethyl ether

Emulsifier: 35 parts by weight of nonylphenol polyglycol ether

To produce a suitable preparation of active compound, 3 parts by weight of active compound are mixed with 7 parts of the solvent emulsified mixture indicated above, and the emulsion concentrate thus obtained is diluted with water to the desired concentration.

1 ml of this preparation of active compound is pipetted into PP blister films of a suitable size. Approximately 25 mites are then transferred into the preparation of active compound.

After 24 hours, the activity of the preparation of active compound is determined in %. 100% means that all mites have been killed, 0% means that no mites have been killed.

In this test, a superior activity compared with the prior art is shown, for example, by the following compounds of the Preparation Examples: 2, 3, 4, 6, 9, 10, 13, 14, 15, 16, 18, 19, 20, 43, 49, 51, 78 and 85.

TABLE H

Psoroptes ovis Test

| Active compounds | Active compound concentration in ppm of a.i. | Degree of destruction in % |
|---|---|---|
| 4-Br, 6-CF$_3$, 2-CF$_3$-benzimidazole-1-CH$_2$-N(CH$_3$)-COOCH$_3$ | (2) 10 | 100 |
| 4-Br, 6-CF$_3$, 2-CF$_3$-benzimidazole-1-CH$_2$-N(C$_2$H$_5$)-COOCH$_3$ | (3) 10 | 100 |
| 4-Br, 6-CF$_3$, 2-CF$_3$-benzimidazole-1-CH$_2$-N(n-C$_3$H$_7$)-COOCH$_3$ | (4) 10 | 100 |
| 4-Br, 6-CF$_3$, 2-CF$_3$-benzimidazole-1-CH$_2$-C(=O)-C(CH$_3$)$_3$ | (6) 10 | 100 |
| 4-Br, 6-CF$_3$, 2-CF$_3$-benzimidazole-1-CH$_2$-CH=CH-CH$_3$ + 5-CF$_3$, 7-Br, 2-CF$_3$-benzimidazole-1-CH$_2$-CH=CH-CH$_3$ | (9) 10 | 100 |
| 4-Br, 6-CF$_3$, 2-CF$_3$-benzimidazole-1-CH$_2$-CH=C(CH$_2$Cl)- | (10) 10<br>1 | 100<br>100 |

TABLE H-continued

*Psoroptes ovis* Test

| Active compounds | | Active compound concentration in ppm of a.i. | Degree of destruction in % |
|---|---|---|---|
| [Structure: 4-Br, 6-CF$_3$ benzimidazole with 2-CF$_3$, N-CH$_2$-O-i-C$_3$H$_7$] + [Structure: 5-CF$_3$, 7-Br benzimidazole with 2-CF$_3$, N-CH$_2$-O-i-C$_3$H$_7$] | (13) | 10<br>1 | 100<br>100 |
| [Structure: 4-Br, 6-CF$_3$ benzimidazole with 2-CF$_3$, N-CH$_2$-O-n-C$_3$H$_7$] + [Structure: 5-CF$_3$, 7-Br benzimidazole with 2-CF$_3$, N-CH$_2$-O-n-C$_3$H$_7$] | (14) | 10<br>1 | 100<br>100 |
| [Structure: 4-Br, 6-CF$_3$ benzimidazole with 2-CF$_3$, N-CH$_2$-O-(CH$_2$)$_3$-C$_6$H$_5$] + [Structure: 5-CF$_3$, 7-Br benzimidazole with 2-CF$_3$, N-CH$_2$-O-(CH$_2$)$_3$-C$_6$H$_5$] | (15) | 10<br>1 | 100<br>100 |
| [Structure: 4-Br, 6-CF$_3$ benzimidazole with 2-CF$_3$, N-CH$_2$-O-CH$_2$-C≡CH] | (16) | 10<br>1 | 100<br>100 |
| [Structure: 4-Br, 6-CF$_3$ benzimidazole with 2-CF$_3$, N-CH$_2$-C(=O)-C(CH$_3$)$_3$] | (18) | 10<br>1 | 100<br>100 |

TABLE H-continued

*Psoroptes ovis* Test

| Active compounds | Active compound concentration in ppm of a.i. | Degree of destruction in % |
|---|---|---|
| (structure 19): 4-Br, 6-CF₃ benzimidazole with 2-CF₃ and N-CH₂-O-CH₂-(3-chlorophenyl) + isomer with CF₃ and Br swapped | (19) 10<br>1 | 100<br>100 |
| (structure 20): 4-Br, 6-CF₃ benzimidazole with 2-CF₃ and N-CH₂-O-C₂H₅ + isomer | (20) 10 | 100 |
| (structure 78): 5-CF₃ benzimidazole with 2-CF₃ and N-CH₂-O-C₂H₅ + isomer | (78) 10 | 100 |
| (structure 85): 5-CF₃, 6-Cl benzimidazole with 2-CF₃ and N-CH₂-OC₂H₅ + isomer (5-Cl, 6-CF₃) | (85) 10 | 100 |

TABLE H-continued

Psoroptes ovis Test

| Active compounds | Active compound concentration in ppm of a.i. | Degree of destruction in % |
|---|---|---|
| 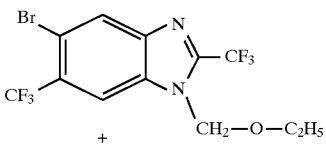 (80) | 10<br>1 | 100<br>100 |
| 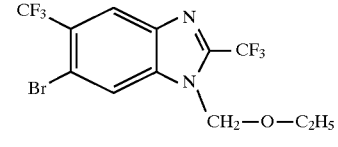 (43) | 10 | 100 |
| 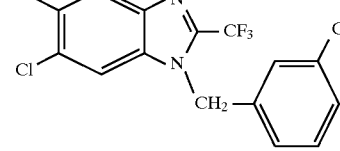 (49) | 10 | 100 |
| 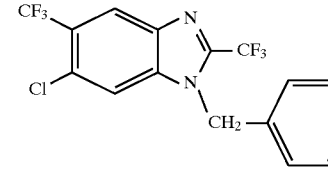 (51) | 10 | 100 |

Example I

*Periplaneta americana* Test:

Solvent: 35 parts by weight of ethylene glycol monomethyl ether

Emulsifier: 35 parts by weight of nonylphenol polyglycol ether

To produce a suitable preparation of active compound, 3 parts by weight of active compound are mixed with 7 parts of the solvent emulsified mixture indicated above, and the emulsion concentrate thus obtained is diluted with water to the desired concentration.

2 ml of this preparation of active compound are pipetted onto filter paper discs (diameter: 9.5 cm) located in suitably sized Petri dishes. After the filter discs have dried, five cockroaches (*Periplaneta americana*) are transferred into the Petri dishes and covered.

After 3 days, the activity of the preparation of active compound is determined in %. 100% means that all cockroaches have been killed, 0% means that no cockroaches have been killed.

In this test, a superior activity compared with the prior art is shown, for example, by the following compounds of the Preparation Examples: 3, 14, 16, 17, 18, 20, 22, 43, 53, 55, 56, 76, 79, 80, 83, 85, 87, 89, 90, 128, 129 and 131.
TABLE I
*Periplaneta americana* Test
| Active compounds | Active compound concentration in ppm of a.i. | Degree of destruction in % |
|---|---|---|
| 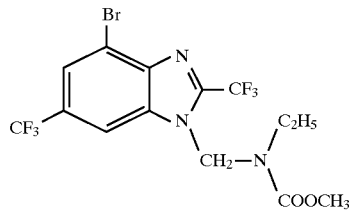 | (3) 1000<br>100 | 100<br>100 |
| 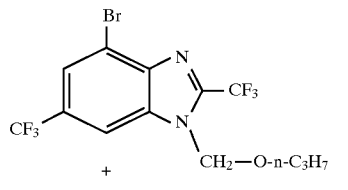 | (14) 1000 | 100 |
| 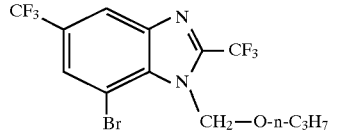 | (16) 1000<br>100 | 100<br>100 |
| 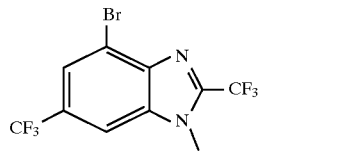 | (17) 1000 | 100 |
| 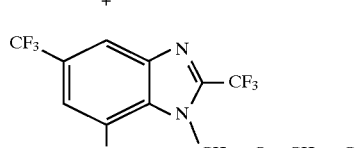 | (18) 1000 | 100 |

TABLE I-continued
*Periplaneta americana* Test
| Active compounds | Active compound concentration in ppm of a.i. | Degree of destruction in % |
|---|---|---|
| 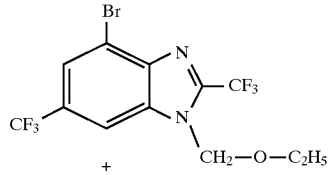 | (20) 1000<br>100 | 100<br>100 |
| 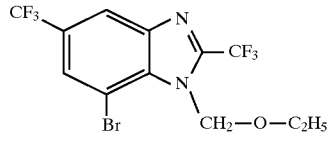 | (22) 1000<br>100 | 100<br>>50 |
| 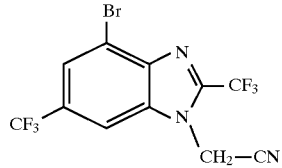 | (79) 1000<br>100 | 100<br>100 |
| 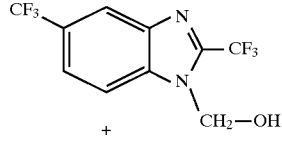 | (43) 1000 | 100 |
| 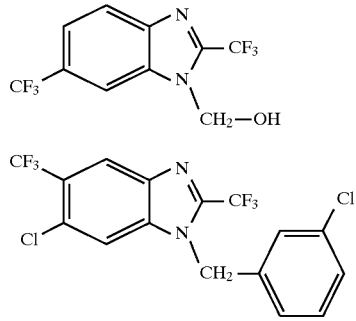 | (55) 1000 | 100 |
| 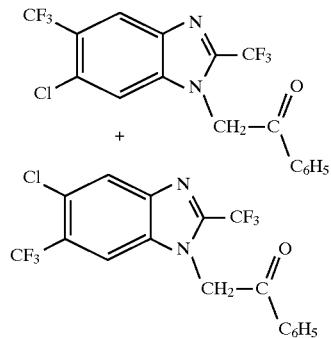 | (53) 1000 | 100 |

TABLE I-continued

*Periplaneta americana* Test

| Active compounds | Active compound concentration in ppm of a.i. | Degree of destruction in % |
|---|---|---|
| (56) 5-CF$_3$, 6-Cl-benzimidazole, 2-CF$_3$, 1-CH$_2$—O-i-C$_3$H$_7$ + 5-Cl, 6-CF$_3$-benzimidazole, 2-CF$_3$, 1-CH$_2$—O-i-C$_3$H$_7$ | 1000<br>100 | 100<br>100 |
| (76) 5-CF$_3$, 6-Br-benzimidazole, 2-CF$_3$, 1-CH$_2$—O-i-C$_3$H$_7$ + 5-Br, 6-CF$_3$-benzimidazole, 2-CF$_3$, 1-CH$_2$—O-i-C$_3$H$_7$ | 1000<br>100 | 100<br>100 |
| (128) 5-F$_3$O-benzimidazole, 2-CF$_3$, 1-CH$_2$—OC$_2$H$_5$ + 6-F$_3$O-benzimidazole, 2-CF$_3$, 1-CH$_2$—OC$_2$H$_5$ | 1000<br>100 | 100<br>>50 |
| (129) 5,6-bis(CF$_3$O)-benzimidazole, 2-CF$_3$, 1-CH$_2$—O—C$_2$H$_5$ | 1000<br>100 | 100<br>>50 |
| (131) 5,6-bis(CF$_3$O)-benzimidazole, 2-CF$_3$, 1-CH$_2$—O—CH$_2$—C≡CH | 1000 | 100 |
| (85) 5-CF$_3$, 6-Cl-benzimidazole, 2-CF$_3$, 1-CH$_2$—OC$_2$H$_5$ + 5-Cl, 6-CF$_3$-benzimidazole, 2-CF$_3$, 1-CH$_2$—OC$_2$H$_5$ | 1000<br>100 | 100<br>100 |

TABLE I-continued

*Periplaneta americana* Test

| Active compounds | Active compound concentration in ppm of a.i. | Degree of destruction in % |
|---|---|---|
| (87) 5-Cl, 6-CF₃ benzimidazole, 2-CF₃, N-CH₂—OC₂H₅ | 1000 | 100 |
| (80) 5-CF₃, 6-Br benzimidazole, 2-CF₃, N-CH₂—OC₂H₅ + 5-Br, 6-CF₃ benzimidazole, 2-CF₃, N-CH₂—OC₂H₅ | 1000 | 100 |
| (89) 5-CF₃, 6-Cl benzimidazole, 2-CF₃, N-CH₂—O-n-C₃H₇ + 5-Cl, 6-CF₃ benzimidazole, 2-CF₃, N-CH₂—O-n-C₃H₇ | 1000 | 100 |
| (90) 5-CF₃O, 6-Cl benzimidazole, 2-CF₃, N-CH₂—O—CH₂—C≡CH + 5-Cl, 6-CF₃O benzimidazole, 2-CF₃, N-CH₂—O—CH₂—C≡CH | 1000 / 100 | 100 / >50 |
| (83) 5-CF₃, 6-Br benzimidazole, 2-CF₃, N-CH₂—O-n-C₃H₇ + 5-Br, 6-CF₃ benzimidazole, 2-CF₃, N-CH₂—O-n-C₃H₇ | 1000 | 100 |

Example J

*Musca domestica* Test:

Solvent: 35 parts by weight of ethylene glycol monomethyl ether

Emulsifier: 35 parts by weight of nonylphenol polyglycol ether

To produce a suitable preparation of active compound, 3 parts by weight of active compound are mixed with 7 parts of the solvent emulsified mixture indicated above, and the emulsion concentrate thus obtained is diluted with water to the desired concentration 2 ml of this preparation of active compound are pipetted onto filter paper discs (diameter. 9.5 cm) located in suitably sized Petri dishes. After the filter discs have dried, 25 test animals (*Musca domestica*; strain WHO [N])) are transferred into the Petri dishes and covered.

After 3 days, the activity of the preparation of active compound is determined in %. 100% means at all flies have been killed, 0% means no flies have been killed.

In this test, a superior activity compared with the prior art is shown, for example, by the following compounds of the Preparation Examples: 16, 17, 18, 20, 56, 76, 80, 83, 87 and 89.

TABLE J

*Musca domestica* Test

| Active compounds | | Active compound concentration in ppm of a.i. | Degree of destruction in % |
|---|---|---|---|
| (structure with Br, CF$_3$, benzimidazole, CF$_3$, CH$_2$—O—CH$_2$—C≡CH) + (isomer) | (16) | 1000<br>100 | 100<br>100 |
| (structure with Br, CF$_3$, benzimidazole, CF$_3$, CH$_2$—O—C(=O)—NH—C(=O)—NH—C$_6$H$_4$—Cl) | (17) | 1000<br>100 | 100<br>100 |
| (structure with Br, CF$_3$, benzimidazole, CF$_3$, CH$_2$—C(=O)—C(CH$_3$)$_3$) | (18) | 1000 | 100 |
| (structure with Br, CF$_3$, benzimidazole, CF$_3$, CH$_2$—O—C$_2$H$_5$) + (isomer) | (20) | 1000<br>100 | 100<br>100 |

TABLE J-continued

*Musca domestica* Test

| Active compounds | | Active compound concentration in ppm of a.i. | Degree of destruction in % |
|---|---|---|---|
| [structure: 5-CF₃, 6-Br benzimidazole, 2-CF₃, N-CH₂-O-n-C₃H₇] + [structure: 5-Br, 6-CF₃ benzimidazole, 2-CF₃, N-CH₂-O-n-C₃H₇] | (83) | 1000 | 100 |
| [structure: 5-CF₃, 6-Cl benzimidazole, 2-CF₃, N-CH₂-O-n-C₃H₇] + [structure: 5-Cl, 6-CF₃ benzimidazole, 2-CF₃, N-CH₂-O-n-C₃H₇] | (89) | 1000 | 100 |
| [structure: 5-Cl, 6-CF₃ benzimidazole, 2-CF₃, N-CH₂-OC₂H₅] | (87) | 1000 | 100 |
| [structure: 5-CF₃, 6-Br benzimidazole, 2-CF₃, N-CH₂-OC₂H₅] + [structure: 5-Br, 6-CF₃ benzimidazole, 2-CF₃, N-CH₂-OC₂H₅] | (80) | 1000 | 100 |
| [structure: 5-CF₃, 6-Cl benzimidazole, 2-CF₃, N-CH₂-O-i-C₃H₇] + [structure: 5-Cl, 6-CF₃ benzimidazole, 2-CF₃, N-CH₂-O-i-C₃H₇] | (56) | 1000 | 100 |

TABLE J-continued

Musca domestica Test

| Active compounds | | Active compound concentration in ppm of a.i. | Degree of destruction in % |
|---|---|---|---|
| 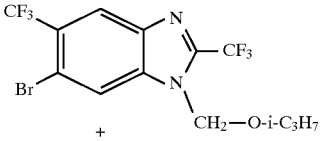 + 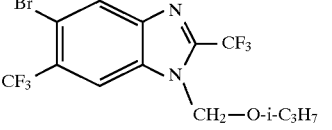 | (76) | 1000 | 100 |

Example K

Phytophthora Test (tomato)/protective

Solvent: 4.7 parts by weight of acetone
Emulsifier: 0.3 part by weight of alkyl-aryl polyglycol ether To produce a suitable preparation of active compound, one part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are then placed in an incubation cabin at 20° C. and about 100% relative atmospheric humidity.

The test is evaluated 3 days after inoculation.

In this test, a clearly superior activity compared with the prior art is shown, for example, by the compound of Preparation Example 48.

TABLE K

Phytophthora Test (tomato)/protective

| Active compound | | Degree of effectiveness in % of the untreated control at an active compound concentration of 10 ppm |
|---|---|---|
| 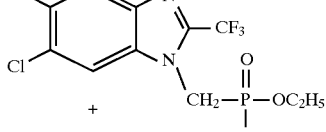 + 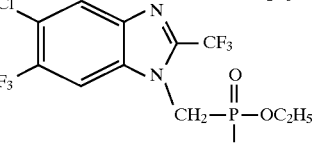 | (48) | 57 |

Example L

Plasmopara Test (vines)/protective
Solvent: 4.7 parts by weight of acetone
Emulsifier: 0.3 part by weight of alkyl-aryl polyglycol ether To produce a suitable preparation of active compound, one part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Plasmopara viticola* and then remain in a humidity chamber at 20° C. to 22° C. and 100% relative atmospheric humidity for one day. The plants are then placed in a greenhouse at 21° C. and 90% atmospheric humidity for 5 days. The plants are then moistened and placed in a humidity chamber for one day.

The test is evaluated 6 days after the inoculation.

In this test, a clearly superior activity compared with the prior art is shown, for example, by the compounds of the following Preparation Examples: 48, 53 and 130.

TABLE L

Plasmopara Test (vines)/protective

| Active compound | | Degree of effectiveness in % of the untreated control at an active compound concentration of 10 ppm |
|---|---|---|
| [structure: Cl, CF₃-substituted benzimidazole with CF₃ and CH₂—P(=O)(OC₂H₅)₂ group] + [structure: CF₃, Cl-substituted benzimidazole with CF₃ and CH₂—P(=O)(OC₂H₅)₂ group] | (48) | 60 |
| [structure: CF₃, Cl-substituted benzimidazole with CF₃ and CH₂—CN group] | (53) | 73 |
| [structure: CF₃O, CF₃O-substituted benzimidazole with CF₃ and CH₂—O-n-C₃H₇ group] | (130) | 74 |

Example M

Post-emergence Test
Solvent: 5 parts by weight of acetone
Emulsifier: 1 part by weight of alkylaryl polyglycol ether To produce a suitable preparation of active compound, one part by weight of active compound is mixed with the stated amount of solvent, the stated amount of emulsifier is added and the concentrate is diluted with water to the desired concentration.

Test plants which have a height of 5–15 cm are sprayed with the preparation of active compound in such a way as to apply the particular amounts of active compound desired per unit area After three weeks, the degree of damage to the plants is rated in % damage in comparison to the development of the untreated control.

The figures denote:

0%=no action (like untreated control)
100%=total destruction

In this test, a clearly superior activity compared with the prior art combined with a comparable crop plant selectivity is shown, for example, by the compound of Preparation Example 79.

TABLE M

| | | Post-emergence test (greenhouse) | | | | | | | | |
|---|---|---|---|---|---|---|---|---|---|---|
| Active compound | Application rate in g/ha | Wheat | Alopecurus | Lolium | Setaria | Amaranthus | Galium | Polygonum | Veronica | Viola |
| (79) | 2000 | 10 | 95 | 99 | 100 | 100 | 95 | 100 | 100 | 100 |

We claim:

1. A 1H-benzimidazole which has the formula

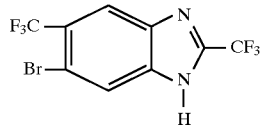

2. An anthropodicidal or nematicidal composition comprising an arthropodicidally or nematicidally effective compound according to claim 1 and an inert carrier.

3. A method of combatting arthropodes or nematodes which comprises applying to said arthropod or nematode or to a habitat of said arthropod or nematode an effective amount of a compound according to claim 1.

* * * * *